(12) United States Patent
Osaka et al.

(10) Patent No.: US 8,664,263 B2
(45) Date of Patent: Mar. 4, 2014

(54) STILBENE COMPOUND, LIGHT-EMITTING ELEMENT, LIGHT-EMITTING DEVICE, ELECTRONIC DEVICE, AND LIGHTING DEVICE

(75) Inventors: Harue Osaka, Kanagawa (JP); Nobuharu Ohsawa, Kanagawa (JP)

(73) Assignee: Semiconductor Energy Laboratory Co., Ltd. (JP)

( * ) Notice: Subject to any disclaimer, the term of this patent is extended or adjusted under 35 U.S.C. 154(b) by 218 days.

(21) Appl. No.: 13/348,939

(22) Filed: Jan. 12, 2012

(65) Prior Publication Data

US 2012/0184755 A1 Jul. 19, 2012

(30) Foreign Application Priority Data

Jan. 14, 2011 (JP) .................................. 2011-005447

(51) Int. Cl.
*A61K 31/381* (2006.01)
*C07D 333/76* (2006.01)

(52) U.S. Cl.
USPC .......................................... 514/443; 549/43

(58) Field of Classification Search
USPC ............................................ 514/443; 549/43
See application file for complete search history.

(56) References Cited

U.S. PATENT DOCUMENTS

| | | | |
|---|---|---|---|
| 5,085,946 A | 2/1992 | Saito et al. | |
| 6,468,675 B1 | 10/2002 | Ishikawa et al. | |
| 6,743,948 B1 | 6/2004 | Hosokawa et al. | |
| 6,951,693 B2 | 10/2005 | Hosokawa et al. | |
| 7,476,745 B2 | 1/2009 | Egawa et al. | |
| 7,732,619 B2 | 6/2010 | Egawa et al. | |
| 7,935,854 B2 | 5/2011 | Egawa | |
| 2003/0072966 A1 | 4/2003 | Hosokawa et al. | |
| 2006/0189828 A1 | 8/2006 | Hosokawa et al. | |
| 2007/0080630 A1 | 4/2007 | Egawa et al. | |
| 2007/0142671 A1 | 6/2007 | Hosokawa et al. | |
| 2008/0088229 A1 | 4/2008 | Egawa | |
| 2010/0301322 A1 | 12/2010 | Egawa et al. | |
| 2011/0204772 A1 | 8/2011 | Egawa | |

FOREIGN PATENT DOCUMENTS

| | | |
|---|---|---|
| JP | 2-291696 | 12/1990 |
| JP | 2004-75580 | 3/2004 |
| JP | 2004-196716 | 7/2004 |
| JP | 2009-221156 | 10/2009 |
| WO | WO 00/39247 A1 | 7/2000 |

OTHER PUBLICATIONS

Cha, S.W. et al, "Electroluminescence of LEDs Consisting Two Layers of Alq$_3$ and High T$_g$, Blue-Light Emitting Branched Compounds," Synthetic Metals, vol. 143, No. 1, 2004, pp. 97-101.

*Primary Examiner* — Taofiq A Solola
(74) *Attorney, Agent, or Firm* — Husch Blackwell LLP

(57) ABSTRACT

An object is to provide a novel stilbene compound suitable for an organic EL light-emitting material. Provided is a novel stilbene compound represented by a general formula (G1) below. In the formula, $Q^1$ and $Q^2$ separately represent an oxygen atom or a sulfur atom; $R^1$ to $R^9$ and $R^{11}$ to $R^{17}$ separately represent any one of a hydrogen atom, an alkyl group having 1 to 6 carbon atoms, a substituted or unsubstituted phenyl group, and a substituted or unsubstituted biphenyl group; $\alpha^1$ to $\alpha^6$ separately represent a substituted or unsubstituted phenylene group; $Ar^1$ and $Ar^2$ separately represent any one of a substituted or unsubstituted aryl group having 6 to 12 carbon atoms forming a ring, a substituted or unsubstituted dibenzothiophen-2-yl group, and a substituted or unsubstituted dibenzofuran-2-yl group; and j, k, m, n, p, and q separately represent 0 or 1.

(G1)

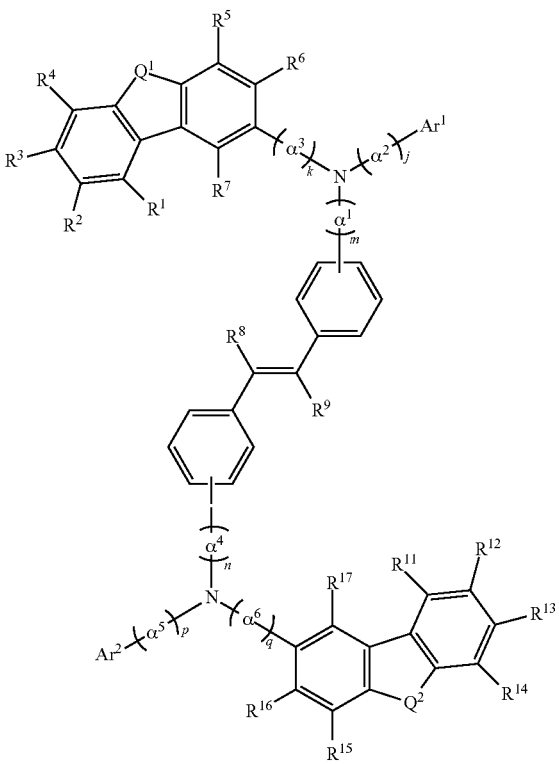

30 Claims, 18 Drawing Sheets

STILBENE COMPOUND, LIGHT-EMITTING ELEMENT, LIGHT-EMITTING DEVICE, ELECTRONIC DEVICE, AND LIGHTING DEVICE

BACKGROUND OF THE INVENTION

1. Field of the Invention

The present invention relates to a novel material that can be applied to a light-emitting element. In addition, the present invention relates to a light-emitting element, a light-emitting device, an electronic device, and a lighting device each using the material.

2. Description of the Related Art

In recent years, research and development have been extensively conducted on light-emitting elements using electroluminescence (EL). In the basic structure of light-emitting elements, a layer that includes a substance having a light-emitting property is interposed between a pair of electrodes. Voltage application to this element causes the substance having a light-emitting property to emit light.

Such light-emitting elements are self-luminous elements and have advantages over liquid crystal displays in having high pixel visibility and eliminating the need for backlights, for example; thus, light-emitting elements are thought to be suitable for flat panel display elements. Such light-emitting elements are also highly advantageous in that they can be thin and lightweight. Besides, very high speed response is also one of the features of such elements.

Furthermore, since such light-emitting elements can be formed in a film form, they make it possible to provide planar light emission easily; thus, planar light emission can be easily obtained with large-area elements using planar light emission. This is a difficult feature to obtain with point light sources typified by incandescent lamps and LEDs or linear light sources typified by fluorescent lamps. Thus, light-emitting elements using EL also have great potential as planar light sources applicable to lighting devices and the like.

Light-emitting elements using EL can be roughly classified according to whether the substance having a light-emitting property is an organic compound or an inorganic compound. In the case of an organic EL element in which an organic compound is used for the substance having a light-emitting property and a layer containing the organic compound having a light-emitting property is provided between a pair of electrodes, voltage application to the light-emitting element causes electrons and holes to be injected from a cathode and an anode, respectively, into the layer containing the organic compound, and current flows. The injection of both electrons and holes brings the organic compound having a light-emitting property into an excited state, and when the organic compound having a light-emitting property returns from the excited state to the ground state, light emission from the organic compound having a light-emitting property can be obtained.

Having such a mechanism, the above-described light-emitting element is referred to as a current-excitation light-emitting element. Note that an excited state formed by an organic compound can be a singlet excited state or a triplet excited state, and luminescence from the singlet excited state is referred to as fluorescence, and luminescence from the triplet excited state is referred to as phosphorescence.

There are many problems in the improvement of element characteristics of such light-emitting elements which depend on substances, and element structure improvement, substance development, etc. have been carried out in order to solve these problems. For example, Patent Document 1 discloses a light-emitting element in which a compound having a stilbene skeleton is used for a light-emitting material, but the light-emitting element cannot be said to have sufficiently high reliability.

In addition to the process of light emission due to carrier recombination through current excitation, there is another process of light emission in which the excitation energy of an organic compound excited with current is transferred to another organic compound and accordingly the latter organic compound is excited to emit light. This process is effective in the case where emission efficiency is reduced due to stacking interaction caused by the high concentration of organic molecules that are desired to emit light (concentration quenching), and the process is generally applied to organic EL elements with an element structure in which a light-emitting material is dispersed in a light-emitting layer (a light-emitting layer is doped with a light-emitting material). Doping a host material with organic molecules that are desired to emit light suppresses the stacking interaction, so that the light-emitting element can have higher efficiency. In such a light-emitting element, excitation energy is transferred from a host material excited current to a dopant material, making the dopant material emit light. Note that when a substance A is dispersed in a matrix formed of a substance B, the substance B forming the matrix is called a host material while the substance A dispersed in the matrix is called a dopant material.

Among these dopant materials, types of materials that emit blue light are fewer than those of materials that emit light of a color having a long wavelength (e.g., red, orange, yellow, or green). One reason for this is that there is considered to be a limited selection of skeletons because a material for blue light emission needs to have small conjugation. Another reason is that the dopant material becomes easy to degrade due to energy for blue light emission which is higher than energy for light emission of a color having a long wavelength.

Therefore, a light-emitting element material for blue light emission is desired in order to provide a highly reliable organic EL element that emits favorable blue light.

REFERENCE

Patent Document 1: Japanese Published Patent Application No. 2009-221156

SUMMARY OF THE INVENTION

In view of the above-described problems, an object of one embodiment of the present invention is to provide a novel light-emitting element material. Another object of one embodiment of the present invention is to provide a novel substance that emits blue light.

Another object is to provide a light-emitting element, a light-emitting device, a lighting device, and an electronic device using the novel substance.

One embodiment of the present invention is a stilbene compound represented by a general formula (G1) below.

(G1)

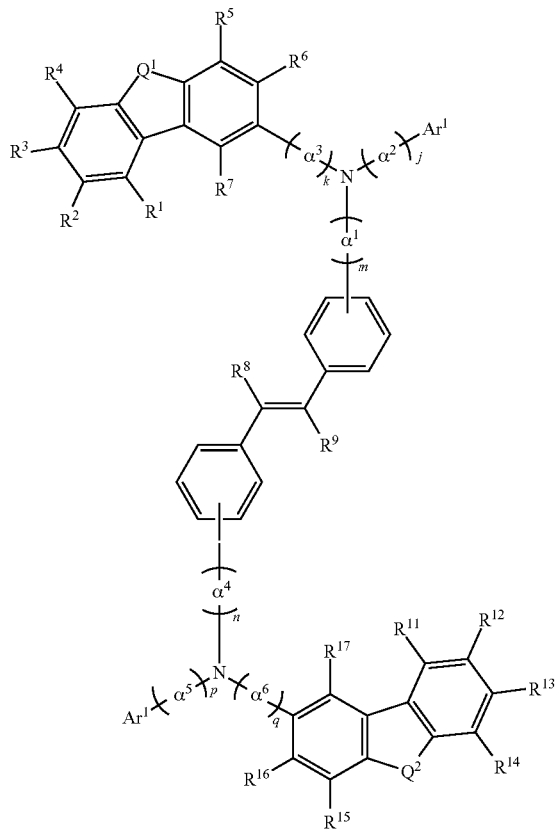

In the general formula (G1), $Q^1$ and $Q^2$ separately represent an oxygen atom or a sulfur atom, and $R^1$ to $R^9$ and $R^{11}$ to $R^{17}$ separately represent any one of a hydrogen atom, an alkyl group having 1 to 6 carbon atoms, a substituted or unsubstituted phenyl group, and a substituted or unsubstituted biphenyl group. Further, $\alpha^1$ to $\alpha^6$ separately represent a substituted or unsubstituted phenylene group. Furthermore, $Ar^1$ and $Ar^2$ separately represent any one of a substituted or unsubstituted aryl group having 6 to 12 carbon atoms forming a ring, a substituted or unsubstituted dibenzothiophen-2-yl group, and a substituted or unsubstituted dibenzofuran-2-yl group. In addition, j, k, m, n, p, and q separately represent 0 or 1.

Another embodiment of the present invention is a stilbene compound represented by a general formula (G2) below.

(G2)

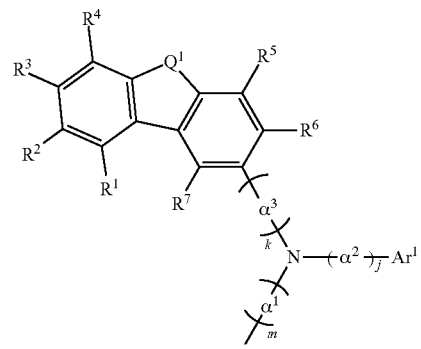

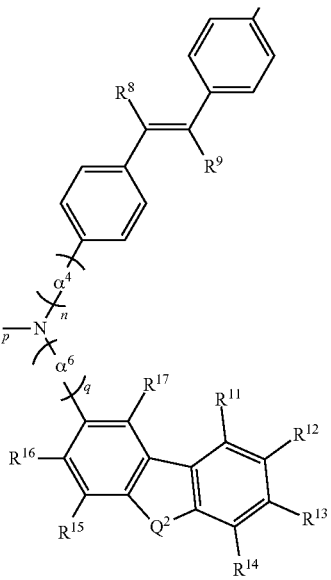

In the general formula (G2), $Q^1$ and $Q^2$ separately represent an oxygen atom or a sulfur atom, and $R^1$ to $R^9$ and $R^{11}$ to $R^{17}$ separately represent any one of a hydrogen atom, an alkyl group having 1 to 6 carbon atoms, a substituted or unsubstituted phenyl group, and a substituted or unsubstituted biphenyl group. Further, $\alpha^1$ to $\alpha^6$ separately represent a substituted or unsubstituted phenylene group. Furthermore, $Ar^1$ and $Ar^2$ separately represent any one of a substituted or unsubstituted aryl group having 6 to 12 carbon atoms forming a ring, a substituted or unsubstituted dibenzothiophen-2-yl group, and a substituted or unsubstituted dibenzofuran-2-yl group. In addition, j, k, m, n, p, and q separately represent 0 or 1.

In the general formulae (G1) and (G2), $\alpha^1$ to $\alpha^6$ may separately be a structure represented by any one of structural formulae ($\alpha$-1) to ($\alpha$-3) below.

(α-1)

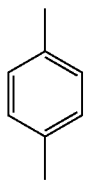

(α-2)

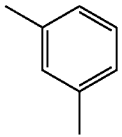

(α-3)

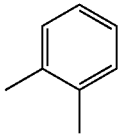

Another embodiment of the present invention is a stilbene compound represented by a general formula (G3) below.

(G3)

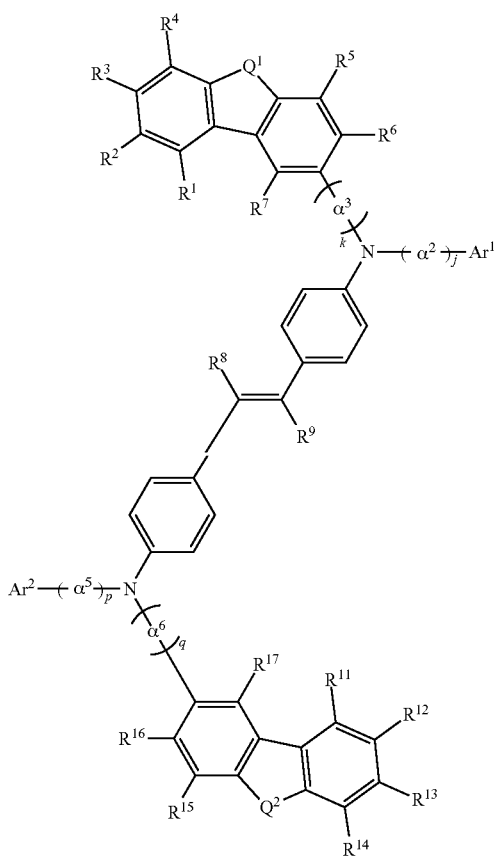

In the general formula (G3), $Q^1$ and $Q^2$ separately represent an oxygen atom or a sulfur atom, and $R^1$ to $R^9$ and $R^{11}$ to $R^{17}$ separately represent any one of a hydrogen atom, an alkyl group having 1 to 6 carbon atoms, a substituted or unsubstituted phenyl group, and a substituted or unsubstituted biphenyl group. Further, $\alpha^2$, $\alpha^3$, $\alpha^5$, and $\alpha^6$ separately represent a substituted or unsubstituted phenylene group. Furthermore, $Ar^1$ and $Ar^2$ separately represent any one of a substituted or unsubstituted aryl group having 6 to 12 carbon atoms forming a ring, a substituted or unsubstituted dibenzothiophen-2-yl group, and a substituted or unsubstituted dibenzofuran-2-yl group. In addition, j, k, p, and q separately represent 0 or 1.

Another embodiment of the present invention is a stilbene compound represented by a general formula (G4) below.

(G4)

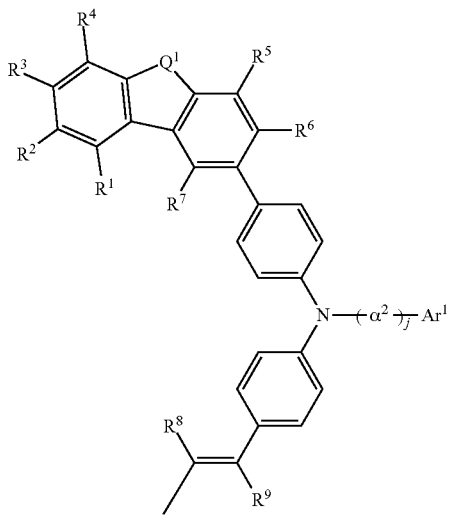

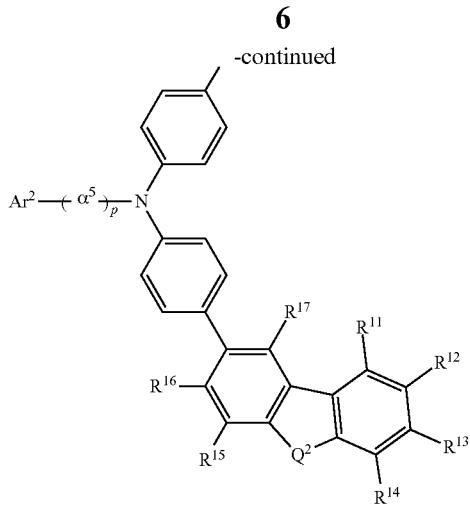

In the general formula (G4), $Q^1$ and $Q^2$ separately represent an oxygen atom or a sulfur atom, and $R^1$ to $R^9$ and $R^{11}$ to $R^{17}$ separately represent any one of a hydrogen atom, an alkyl group having 1 to 6 carbon atoms, a substituted or unsubstituted phenyl group, and a substituted or unsubstituted biphenyl group. Further, $\alpha^2$ and $\alpha^5$ separately represent a substituted or unsubstituted phenylene group. Furthermore, $Ar^1$ and $Ar^2$ separately represent any one of a substituted or unsubstituted aryl group having 6 to 12 carbon atoms forming a ring, a substituted or unsubstituted dibenzothiophen-2-yl group, and a substituted or unsubstituted dibenzofuran-2-yl group. In addition, j and p separately represent 0 or 1.

Further, $Ar^1$ and $Ar^2$ in the general formulae (G1) to (G4) may be a structure represented by a structural formula (Ar-1) or a general formula (Ar-2) below.

(Ar-1)

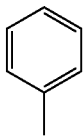

(Ar-2)

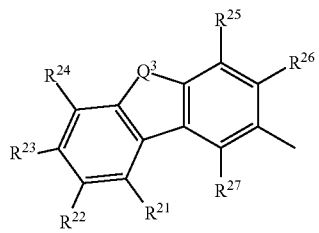

In the general formula (Ar-2), $Q^3$ represents an oxygen atom or a sulfur atom, and $R^{21}$ to $R^{27}$ separately represent any one of a hydrogen atom, an alkyl group having 1 to 6 carbon atoms, a substituted or unsubstituted phenyl group, and a substituted or unsubstituted biphenyl group.

Further, $R^1$ to $R^9$ and $R^{11}$ to $R^{17}$ in the general formulae (G1) to (G4) and $R^{21}$ to $R^{27}$ in the general formula (Ar-2) may be a structure represented by any one of structural formulae (R-1) to (R-9) below.

(R-1)

—H

(R-2)

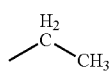
(R-3)

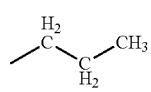
(R-4)

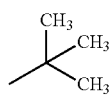
(R-5)

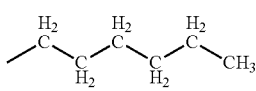
(R-6)

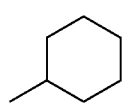
(R-7)

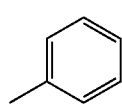
(R-8)

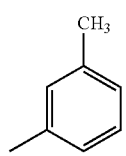
(R-9)

Another embodiment of the present invention is a light-emitting element using any of the above stilbene compounds.

Another embodiment of the present invention is a light-emitting device using the above light-emitting element.

Another embodiment of the present invention is a lighting device using the above light-emitting device.

Another embodiment of the present invention is an electronic device using the above light-emitting device.

Note that the light-emitting device in this specification includes an image display device, a light source, and an electronic device. In addition, the light-emitting device includes all the following modules: a module in which a connector, such as a flexible printed circuit (FPC), a tape automated bonding (TAB) tape, or a tape carrier package (TCP), is attached to a panel; a module in which a printed wiring board is provided at the end of a TAB tape or a TCP; and a module in which an integrated circuit (IC) is directly mounted on a light-emitting element by a chip-on-glass (COG) method.

A stilbene compound according to one embodiment of the present invention can emit visible light having a short wavelength, and can emit blue light with favorable color purity.

In addition, by use of any of the stilbene compounds according to one embodiment of the present invention, a light-emitting element having high emission efficiency and high reliability can be obtained.

Further, by use of this light-emitting element, a light-emitting device, an electronic device, and a lighting device each having high reliability can be obtained.

DETAILED DESCRIPTION OF THE INVENTION

Figure 1A:
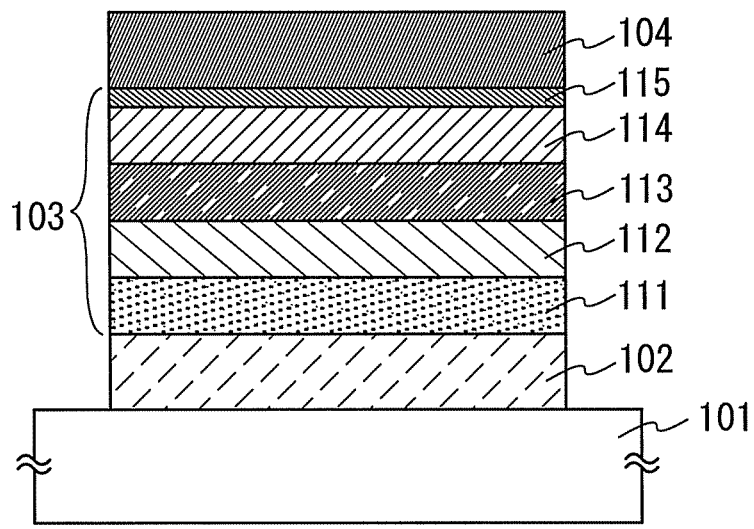
FIGS. 1A and 1B each illustrate a light-emitting element according to one embodiment of the present invention.

Hereinafter, embodiments of the present invention will be described in detail with reference to the accompanying drawings. However, the invention is not limited to the description, and those skilled in the art will appreciate that a variety of modifications can be made to the modes and details without departing from the spirit and scope of the invention. Therefore, the invention should not be construed as being limited to the description in the following embodiments.

Embodiment 1

In this embodiment, stilbene compounds according to one embodiment of the present invention are described.

A stilbene compound in this embodiment is represented by the general formula (G1) below.

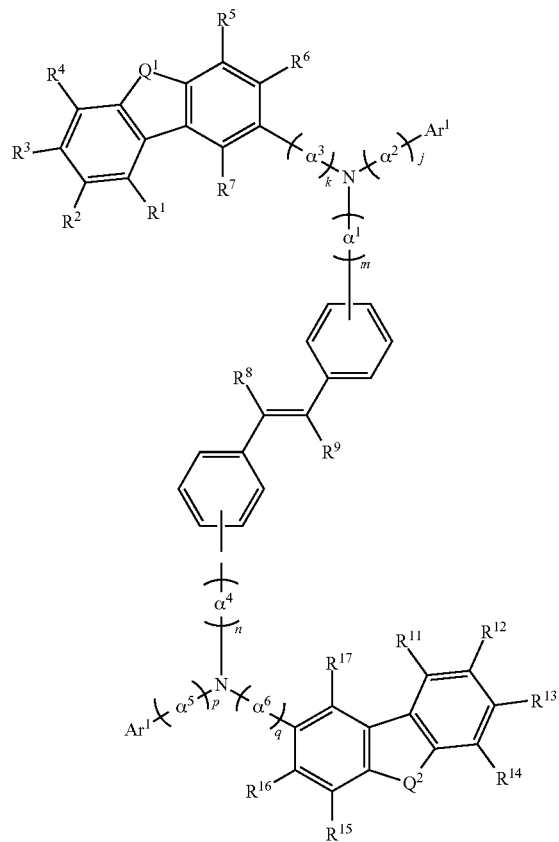

(G1)

In the general formula (G1), $Q^1$ and $Q^2$ separately represent an oxygen atom or a sulfur atom, and $R^1$ to $R^9$ and $R^{11}$ to $R^{17}$ separately represent any one of a hydrogen atom, an alkyl group having 1 to 6 carbon atoms, a substituted or unsubstituted phenyl group, and a substituted or unsubstituted biphenyl group. Further, $\alpha^1$ to $\alpha^6$ separately represent a substituted or unsubstituted phenylene group. Furthermore, $Ar^1$ and $Ar^2$ separately represent any one of a substituted or unsubstituted aryl group having 6 to 12 carbon atoms forming a ring, a substituted or unsubstituted dibenzothiophen-2-yl group, and a substituted or unsubstituted dibenzofuran-2-yl group. In addition, j, k, m, n, p, and q separately represent 0 or 1.

In this embodiment, either a trans form of stilbene or a cis form of stilbene may be possible. Use of a trans faun of stilbene is preferred because such use can achieve greater thermodynamic stability.

Further, a structure represented by the general formula (G2) below is preferred because its synthesis is easy.

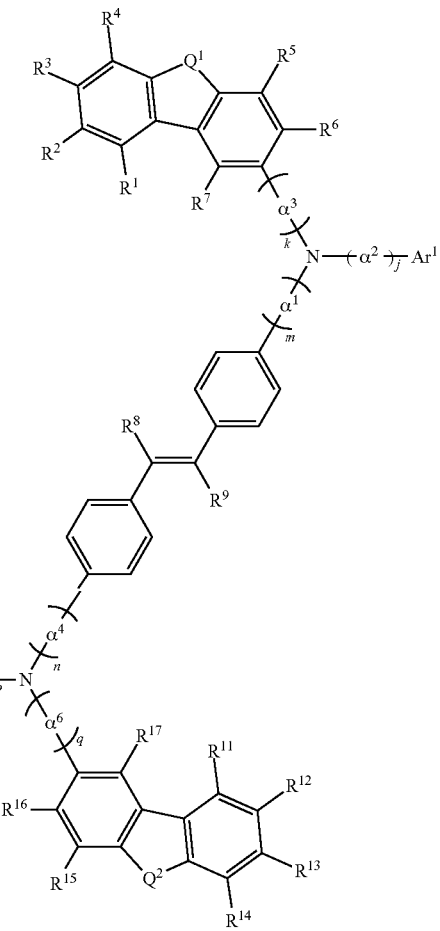

(G2)

In the general formula (G2), $Q^1$ and $Q^2$ separately represent an oxygen atom or a sulfur atom, and $R^1$ to $R^9$ and $R^{11}$ to $R^{17}$ separately represent any one of a hydrogen atom, an alkyl group having 1 to 6 carbon atoms, a substituted or unsubstituted phenyl group, and a substituted or unsubstituted biphenyl group. Further, $\alpha^1$ to $\alpha^6$ separately represent a substituted or unsubstituted phenylene group. Furthermore, $Ar^1$ and $Ar^2$ separately represent any one of a substituted or unsubstituted aryl group having 6 to 12 carbon atoms forming a ring, a substituted or unsubstituted dibenzothiophen-2-yl group, and a substituted or unsubstituted dibenzofuran-2-yl group. In addition, j, k, m, n, p, and q separately represent 0 or 1.

The case where any of $R^1$ to $R^9$ and $R^{11}$ to $R^{17}$ or either $Ar^1$ or $Ar^2$ in the general formulae (G1) and (G2) has an alkyl group as a substituent is preferred, because, in this case, solubility in an organic solvent is increased and purification is facilitated accordingly. Such a case is preferred also because the increase in solubility can increase the uniformity of a film in wet process manufacture of an organic EL element.

More preferably, $Ar^1$ or $Ar^2$ in the general formulae (G1) and (G2) is a substituted or unsubstituted aryl group.

The case where any of $R^1$ to $R^9$ and $R^{11}$ to $R^{17}$ in the general formulae (G1) and (G2) is hydrogen or either $Ar^1$ or $Ar^2$ in the general formulae (G1) and (G2) is unsubstituted is preferred, because synthesis is simplified in this case.

Since the stilbene compounds represented by the general formulae (G1) and (G2) have, in a molecule, a sterically bulky structure, such as a dibenzofuranyl group or a dibenzothiophenyl group, interaction between molecules is suppressed and morphology (the form of molecules) is improved. Accordingly, films using the stilbene compounds represented by the general formulae (G1) and (G2) have improved film quality; thus, in the case where such a film is used for a light-emitting layer, concentration quenching or excimer formation can be suppressed more easily.

Conjugation of a dibenzofuranyl group and that of a dibenzothiophenyl group are not large because their skeletons have low molecular weight. Therefore, even when either of these skeletons is included in a molecule, the conjugation is less likely to extend, so that emission color having a short wavelength can be obtained.

In the case where any of $R^1$ to $R^9$ and $R^{11}$ to $R^{17}$ in the general formulae (G1) and (G2) has an alkyl group or an aryl group such as a phenyl group or a biphenyl group as a substituent, a more sterical structure can be formed and interaction between molecules is suppressed. This is a preferred case because, in this case, the morphology (the form of molecules) can be improved. In a similar manner, the case where $Ar^1$ or $Ar^2$ in the general formulae (G1) and (G2) has an alkyl group or an aryl group such as a phenyl group or a biphenyl group as a substituent is preferred, because, in this case, a more sterical structure can be formed and interaction between molecules is suppressed.

Further, a dibenzofuranyl group or a dibenzothiophenyl group, the 2-position of which is bonded to a nitrogen atom of an amine, is a skeleton that is stable with respect to holes and has a high hole-injection property and a high hole-transport property. In addition, a stilbene skeleton is a skeleton that is stable with respect to carriers and has a high carrier-transport property. Therefore, like the stilbene compounds represented by the general formulae (G1) and (G2), a stilbene compound having a dibenzofuranyl group or a dibenzothiophenyl group in a molecule can be said to be a compound that can give high efficiency and a long lifetime when used for a light-emitting element; thus, such a stilbene compound is suitable as a light-emitting element material.

Furthermore, since a stilbene skeleton having high fluorescent quantum yield is used, high emission efficiency can be obtained.

Specific examples of substituents represented by $\alpha^1$ to $\alpha^6$ in the general formula (G1) include structural formulae (α-1) to (α-3) below.

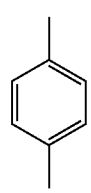
(α-1)

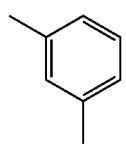
(α-2)

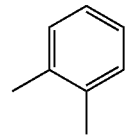
(α-3)

In addition, n and m in the general formula (G2) are preferably 0, as represented by the general formula (G3) below.

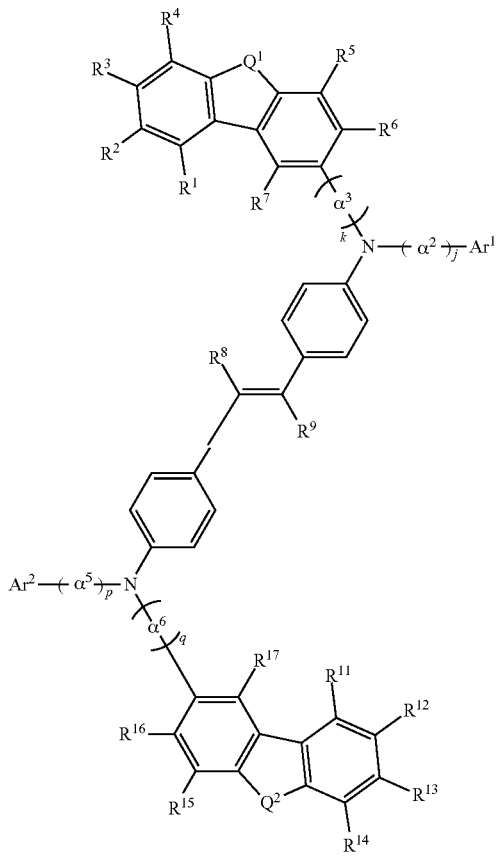
(G3)

In the general formula (G3), $Q^1$ and $Q^2$ separately represent an oxygen atom or a sulfur atom, and $R^1$ to $R^9$ and $R^{11}$ to $R^{17}$ separately represent any one of a hydrogen atom, an alkyl group having 1 to 6 carbon atoms, a substituted or unsubstituted phenyl group, and a substituted or unsubstituted biphenyl group. Further, $\alpha^2$, $\alpha^3$, $\alpha^5$, and $\alpha^6$ separately represent a substituted or unsubstituted phenylene group. Furthermore, $Ar^1$, and $Ar^2$ separately represent any one of a substituted or unsubstituted aryl group having 6 to 12 carbon atoms forming a ring, a substituted or unsubstituted dibenzothiophen-2-yl group, and a substituted or unsubstituted dibenzofuran-2-yl group. In addition, j, k, p, and q separately represent 0 or 1.

Specific examples of substituents represented by $\alpha^2$, $\alpha^3$, $\alpha^5$, and $\alpha^6$ in the general formula (G3) include the structural formulae (α-1) to (α-3).

In this case, a paraphenylene group like that represented by the structural formula (α-1) is preferably used as $\alpha^1$ because such use enables the excited state to be more stable.

As represented by the general formula (G4) below, a more preferred stilbene compound has a substituent represented by the structural formula (α-1), as $α^3$ and $α^6$ in the general formula (G3).

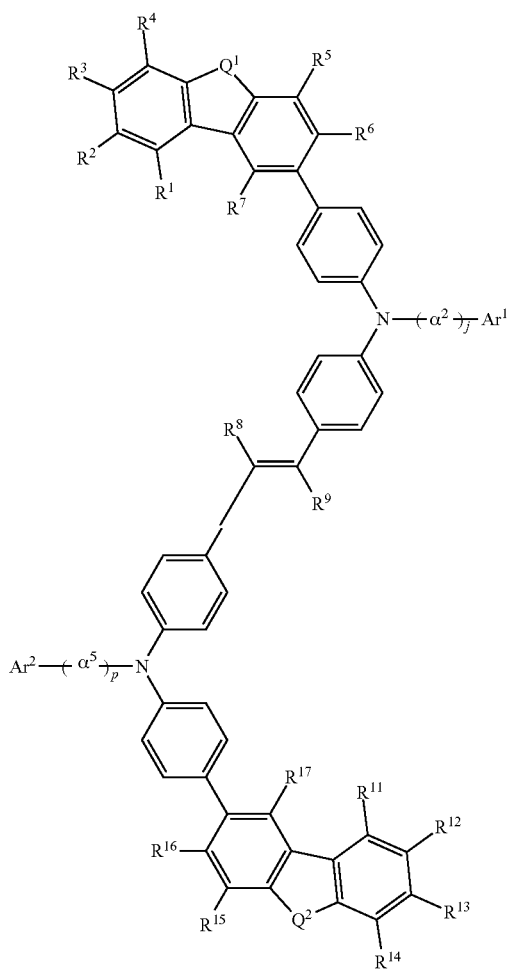

(G4)

In the general formula (G4), $Q^1$ and $Q^2$ separately represent an oxygen atom or a sulfur atom, and $R^1$ to $R^9$ and $R^{11}$ to $R^{17}$ separately represent any one of a hydrogen atom, an alkyl group having 1 to 6 carbon atoms, a substituted or unsubstituted phenyl group, and a substituted or unsubstituted biphenyl group. Further, $α^2$ and $α^5$ separately represent a substituted or unsubstituted phenylene group. Furthermore, $Ar^1$ and $Ar^2$ separately represent any one of a substituted or unsubstituted aryl group having 6 to 12 carbon atoms forming a ring, a substituted or unsubstituted dibenzothiophen-2-yl group, and a substituted or unsubstituted dibenzofuran-2-yl group. In addition, j and p separately represent 0 or 1.

Specific examples of substituents represented by $α^2$ and $α^5$ in the general formula (G4) include the structural formulae (α-1) to (α-3) illustrated above.

Specific examples of substituents represented by $Ar^1$ and $Ar^2$ in the general formulae (G1) to (G4) are the structural formula (Ar-1) and the general formula (Ar-2) below, and the like.

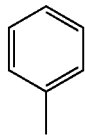

(Ar-1)

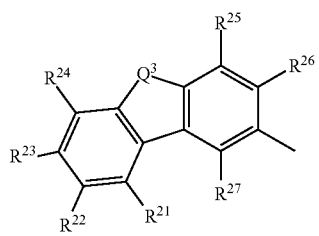

(Ar-2)

In the general formula (Ar-2), $Q^3$ represents an oxygen atom or a sulfur atom, and $R^{21}$ to $R^{27}$ separately represent any one of a hydrogen atom, an alkyl group having 1 to 6 carbon atoms, a substituted or unsubstituted phenyl group, and a substituted or unsubstituted biphenyl group.

When a substituent represented by $Ar^2$ is the above general formula (Ar-2), it is more preferable that j and p in the general formula (G4) each be 1 and $α^2$ and $α^5$ be each a paraphenylene group like that represented by the structural formula (α-1). In addition, it is preferable that $Q^1$ and $Q^2$ in the general formulae (G1) to (G4) and $Q^3$ in the general formula (Ar-2) be the same elements. When such heterocycles have substituents, it is more preferable that the heterocycle including $Q^1$, the heterocycle including $Q^2$, and the heterocycle including $Q^3$ have the same substituents at the same positions (e.g., $R^5$, $R^{15}$ and $R^{25}$, or $R^6$, $R^{16}$ and $R^{26}$).

It is even more preferable that the heterocycle including $Q^1$, the heterocycle including $Q^2$, and the heterocycle including $Q^3$ be unsubstituted, because the synthesis is simplified in this case.

Specific examples of substituents represented by $R^1$ to $R^9$ and $R^{11}$ to $R^{17}$ in the general formulae (G1) to (G4) and $R^{21}$ to $R^{27}$ in the general formula (Ar-2) are the structural formulae (R-1) to (R-9) below, and the like.

(R-1)

(R-2)

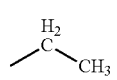

(R-3)

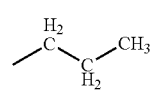

(R-4)

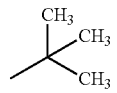

(R-5)

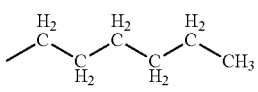

(R-6)

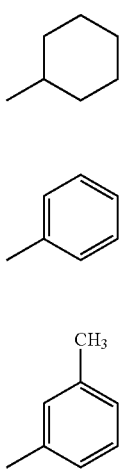
(R-7)
(R-8)
(R-9)
Specific examples of the stilbene compounds represented by the general formulae (G1) to (G4) are, but not limited to, stilbene compounds represented by structural formulae (100) to (110).
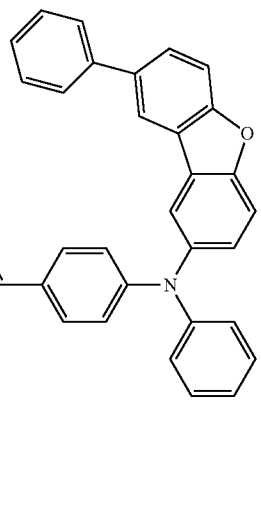
(102)
(100)
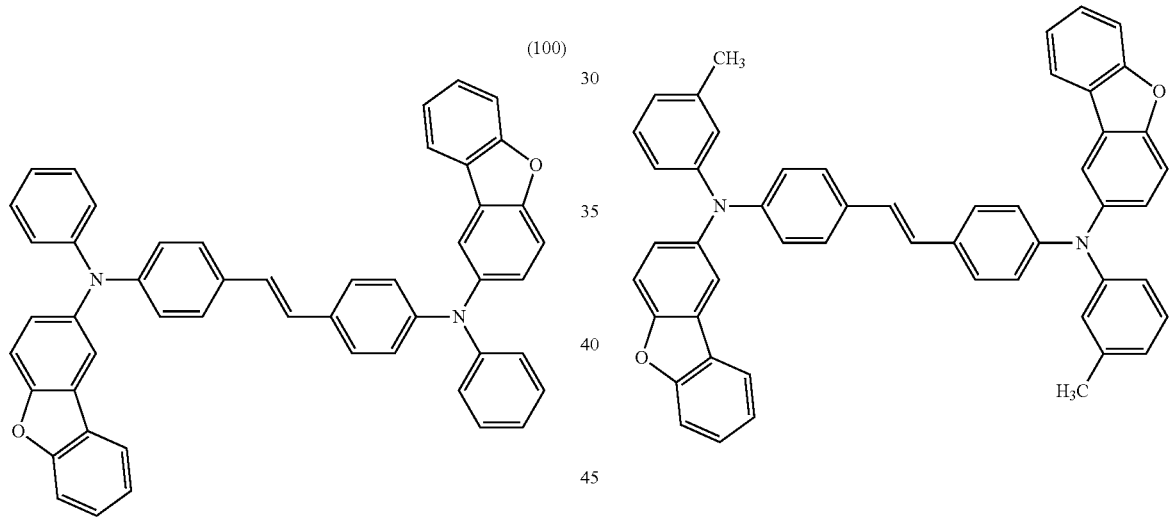
(103)
(101)
(104)
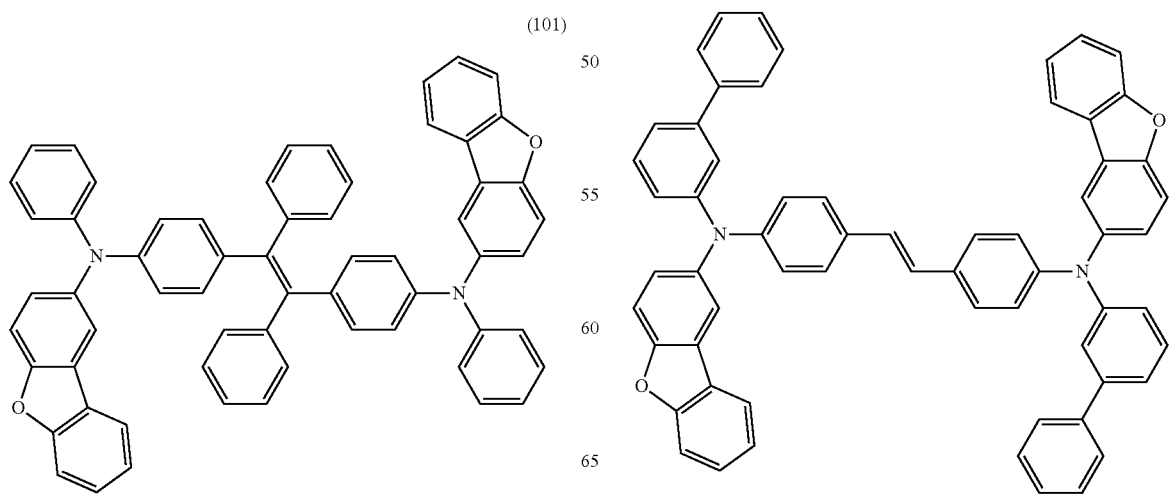

(105)
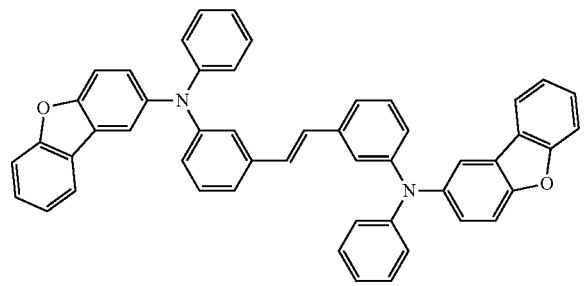

(108)
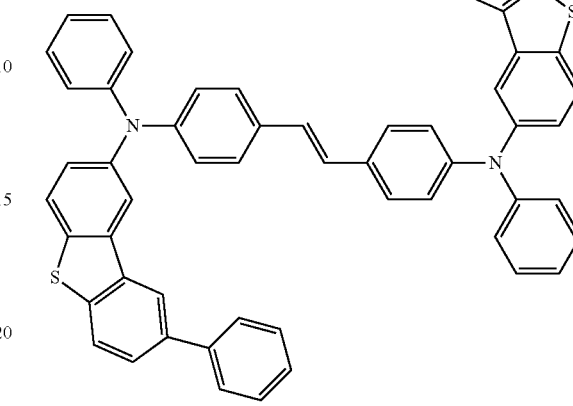

(106)

(109)

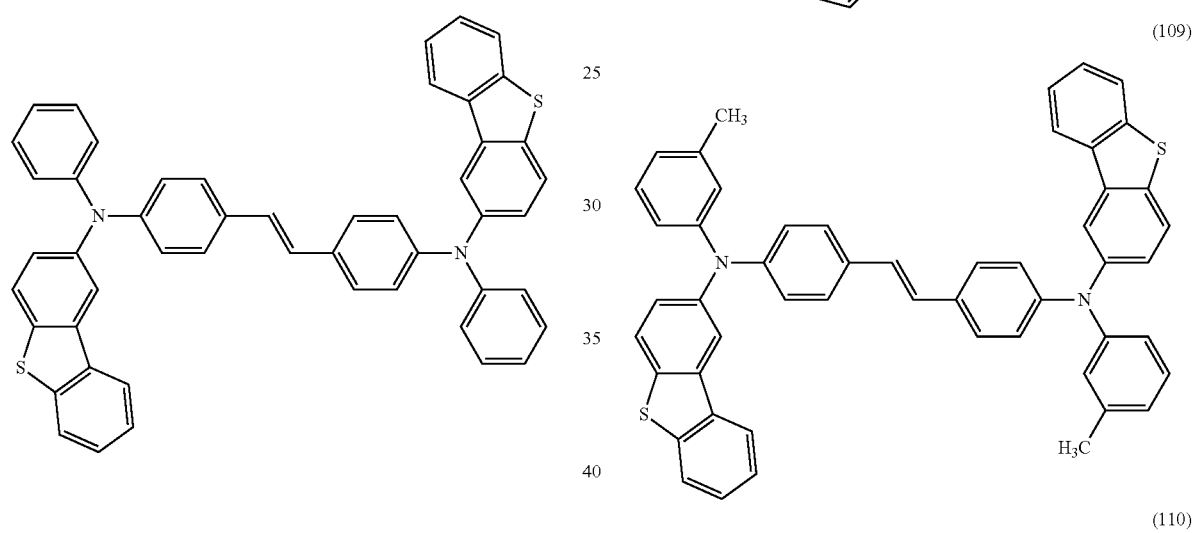

(107)

(110)

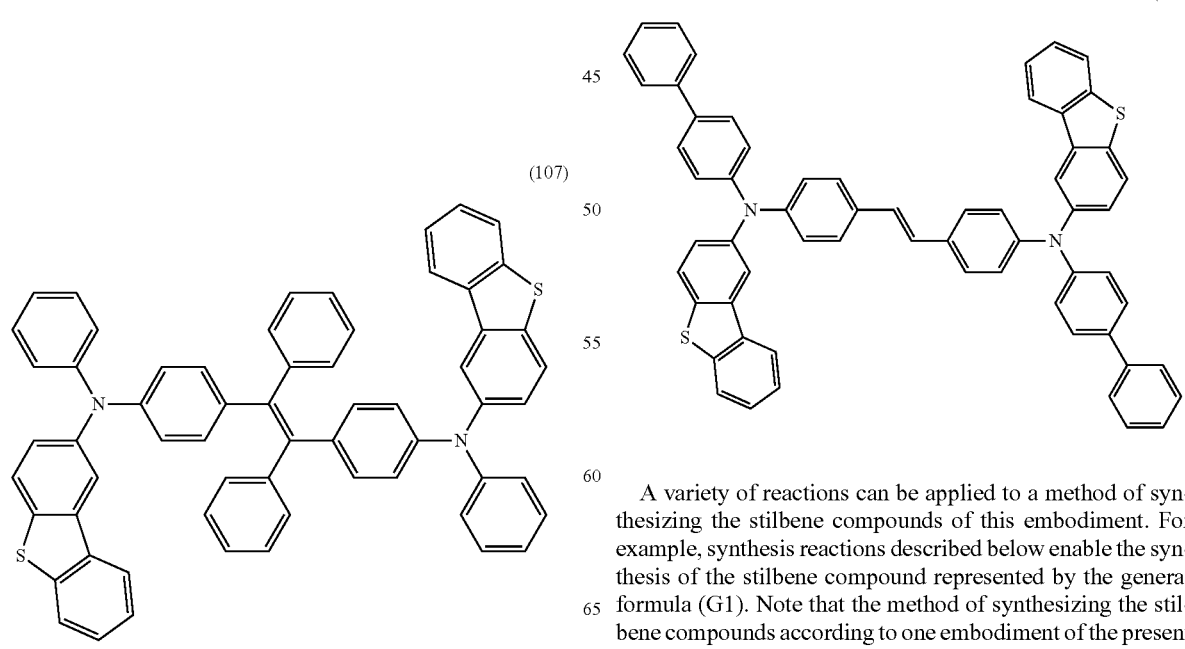

A variety of reactions can be applied to a method of synthesizing the stilbene compounds of this embodiment. For example, synthesis reactions described below enable the synthesis of the stilbene compound represented by the general formula (G1). Note that the method of synthesizing the stilbene compounds according to one embodiment of the present invention is not limited to the following synthesis methods.

[Method of Synthesizing Stilbene Compound Represented by General Formula (G1)]

First, as illustrated in a synthesis scheme (A-1), a dibenzofuran compound or a dibenzothiophene compound (a1) is halogenated, so that a halogenated dibenzofuran compound or a halogenated dibenzothiophene compound (a2) can be obtained.

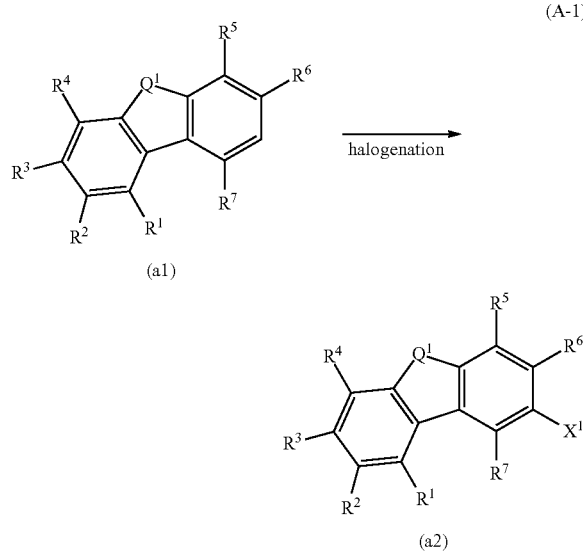

In the synthesis scheme (A-1), $Q^1$ represents an oxygen atom or a sulfur atom, and $R^1$ to $R^7$ separately represent any one of a hydrogen atom, an alkyl group having 1 to 6 carbon atoms, a substituted or unsubstituted phenyl group, and a substituted or unsubstituted biphenyl group.

In addition, $X^1$ represents a halogen, and as the halogen, it is preferable to use chlorine, bromine, or iodine. In order that the synthesis be inexpensive, it is preferable to use bromine or even more preferable to use chlorine. Further, in order that a halogen group of the generated halogenated dibenzofuran compound or halogenated dibenzothiophene compound (a2) has high activity, it is preferable to use bromine or even more preferable to use iodine. The halogen group of the halogenated dibenzofuran compound or halogenated dibenzothiophene compound (a2) preferably has high activity because, in such a case, the reactivity is increased in the subsequent reactions.

Examples of a halogenating agent that can be used include a mixture of iodine and orthoperiodic acid, and bromine. When a mixture of iodine and orthoperiodic acid is used, sulfuric acid can be used as a reaction accelerator, and glacial acetic acid can be given as a solvent that can be used. When bromine is used, chloroform, dichloromethane, carbon tetrachloride, or the like can be given as a solvent that can be used.

Next, as illustrated in a synthesis scheme (A-2), after the halogenated dibenzofuran compound or halogenated dibenzothiophene compound (a2) is lithiated or after a Grignard reagent is prepared from the halogenated dibenzofuran compound or halogenated dibenzothiophene compound (a2), a reaction with borate ester is caused, so that a 2-boron compound of dibenzofuran or a 2-boron compound of dibenzothiophene (a3) can be obtained.

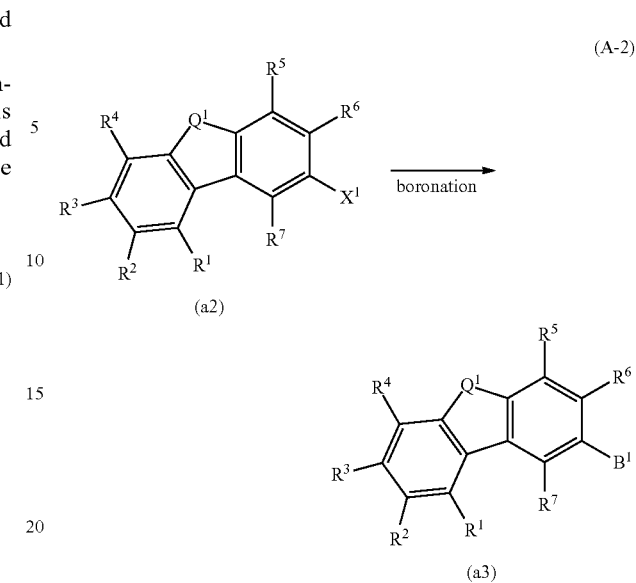

Note that in the synthesis scheme (A-2), $Q^1$ represents an oxygen atom or a sulfur atom, and $R^1$ to $R^7$ separately represent any one of a hydrogen atom, an alkyl group having 1 to 6 carbon atoms, a substituted or unsubstituted phenyl group, and a substituted or unsubstituted biphenyl group. In addition, $X^1$ represents a halogen, and as the halogen, chlorine, bromine, or iodine is preferably used. Further, $B^1$ represents boronic acid or dialkoxyboron.

Examples of a reagent that can be used as a lithiating agent include alkyllithium reagents such as n-butyllithium, tert-butyllithium, and methyllithium. Examples of the Grignard reagent include magnesium that is activated by ethylene bromide or the like. Examples of a solvent include a dehydrating solvent, like an ether such as diethyl ether or tetrahydrofuran (THF).

Next, as illustrated in a synthesis scheme (A-3), the 2-boron compound of dibenzofuran or the 2-boron compound of dibenzothiophene (a3) and a dihalogenated arene (a4) undergo a coupling reaction using a metal catalyst in the presence of a base, so that a halogenated dibenzofuran boron compound or a halogenated dibenzothiophene boron compound (a5) can be obtained.

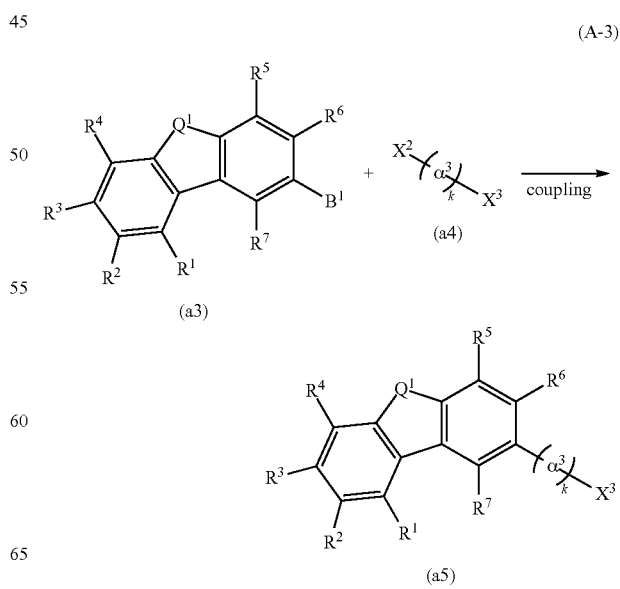

Note that in the synthesis scheme (A-3), $Q^1$ represents an oxygen atom or a sulfur atom, and $R^1$ to $R^7$ separately represent any one of a hydrogen atom, an alkyl group having 1 to 6 carbon atoms, a substituted or unsubstituted phenyl group, and a substituted or unsubstituted biphenyl group. In addition, $\alpha^3$ represents a substituted or unsubstituted phenylene group.

In the synthesis scheme (A-3), $X^2$ and $X^3$ of the dihalogenated arene (a4) separately represent a halogen, and as the halogen, it is preferable to use chlorine, bromine, or iodine. In terms of higher reactivity, it is preferable to use bromine or even more preferable to use iodine.

In order that $B^1$ of the 2-boron compound of dibenzofuran or of the 2-boron compound of dibenzothiophene (a3) and $X^2$ of the dihalogenated arene (a4) be reacted more selectively, $X^2$ is preferably a halogen having higher reactivity than $X^3$. For example, when $X^3$ is a chlorine atom, $X^2$ is preferably a bromine atom or an iodine atom; when $X^3$ is a bromine atom, $X^2$ is preferably an iodine atom. Accordingly, it is possible to reduce by-product generation due to the case where $B^1$ of the 2-boron compound of dibenzofuran or of the 2-boron compound of dibenzothiophene (a3) reacts with both $X^2$ and $X^3$.

When the Suzuki-Miyaura reaction is performed in the synthetic scheme (A-3), examples of the palladium catalyst that can be used are palladium(II)acetate, tetrakis(triphenylphosphine)palladium(0), bis(triphenylphosphine)palladium(II)dichloride, and the like. Examples of a ligand of the palladium catalyst which can be used are tri(ortho-tolyl)phosphine, triphenylphosphine, tricyclohexylphosphine, and the like. In addition, examples of the base that can be used are organic bases such as sodium tert-butoxide (abbreviation: tert-BuONa), inorganic bases such as potassium carbonate and sodium carbonate, and the like. Examples of the solvent that can be used are the following: a mixed solvent of toluene and water; a mixed solvent of toluene, alcohol such as ethanol, and water; a mixed solvent of xylene and water; a mixed solvent of xylene, alcohol such as ethanol, and water; a mixed solvent of benzene and water; a mixed solvent of benzene, alcohol such as ethanol, and water; a mixed solvent of an ether such as ethylene glycol dimethyl ether and water; and the like. More preferred examples are the following: a mixed solvent of toluene and water; a mixed solvent of toluene, ethanol, and water; or a mixed solvent of ether such as ethylene glycol dimethyl ether and water.

As the reaction illustrated in the synthesis scheme (A-3), cross coupling reactions which employ an organoaluminum compound, an organozirconium compound, an organozinc compound, an organotin compound, or the like, in addition to the boron compound, may be used. Furthermore, in this coupling, a triflate group or the like may be used besides a halogen.

A by-product generated by reaction of two 2-boron compounds of dibenzofuran or two 2-boron compounds of dibenzothiophene (a3) with one dihalogenated arene (a4) has a sufficiently higher molecular weight than the halogenated dibenzofuran boron compound or halogenated dibenzothiophene boron compound (a5), which is the object of the synthesis; therefore, the by-product can be easily separated from the object of the synthesis by column purification. In addition, this by-product has no active site, and thus will not react with other compounds in the subsequent reactions and will not produce any further by-products. Therefore, it is also possible to remove this by-product from a compound in which this by-product is mixed, after the subsequent reactions.

Next, as illustrated in a synthesis scheme (A-4), the halogenated dibenzofuran boron compound or halogenated dibenzothiophene boron compound (a5) and an arylamine compound (a6) undergo a coupling reaction, so that a diarylamine compound (a7) can be obtained.

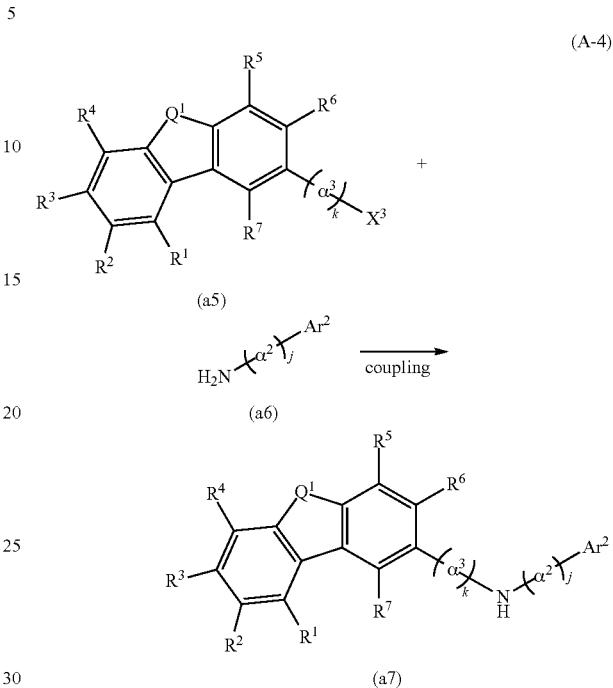

In the synthesis scheme (A-4), $Q^1$ represents an oxygen atom or a sulfur atom, and $R^1$ to $R^7$ separately represent any one of a hydrogen atom, an alkyl group having 1 to 6 carbon atoms, a substituted or unsubstituted phenyl group, and a substituted or unsubstituted biphenyl group. In addition, $\alpha^2$ and $\alpha^3$ separately represent a substituted or unsubstituted phenylene group. Furthermore, $Ar^2$ represents any one of a substituted or unsubstituted aryl group having 6 to 12 carbon atoms forming a ring, a substituted or unsubstituted dibenzothiophen-2-yl group, and a substituted or unsubstituted dibenzofuran-2-yl group. Further, j and k are separately 0 or 1. In addition, $X^3$ represents a halogen, and as the halogen, it is preferable to use chlorine, bromine, or iodine. In terms of higher reactivity, it is preferable to use bromine or even more preferable to use iodine.

When a substituent represented by $Ar^2$ is the above general formula (Ar-2), it is more preferable that j in the diarylamine compound (a7) be 1 and $\alpha^2$ be a paraphenylene group like that represented by the structural formula ($\alpha$-1). In addition, it is preferable that $Q^1$ in the general formula (G1) and $Q^3$ in the general formula (Ar-2) be the same elements, and when these heterocycles have substituent, it is more preferable that the heterocycle including $Q^1$ and the heterocycle including $Q^3$ have the same substituent at the same position (e.g., $R^5$ and $R^{25}$, or $R^6$ and $R^{26}$). Such a structure is preferred because, in this case, a heterocycle including $Q^1$ (a dibenzofuranyl group or a dibenzothiophenyl group) and a heterocycle including $Q^3$ can undergo coupling in one step so as to form a diphenylamine compound and thus the synthesis is simplified.

It is even more preferable that the heterocycle including $Q^1$ and the heterocycle including $Q^3$ be unsubstituted, because the synthesis is simplified in this case.

In the synthesis scheme (A-4), there are a variety of reaction conditions for the coupling reaction of an aryl compound having a halogen group and an aryl compound having amine (primary arylamine compound); for example, a synthesis method using a metal catalyst in the presence of a base can be applied.

The case where a Hartwig-Buchwald reaction is used in the synthesis scheme (A-4) is described. A palladium catalyst can be used as the metal catalyst, and a mixture of a palladium complex and a ligand thereof can be used as the palladium catalyst. Examples of the palladium catalyst are bis(dibenzylideneacetone)palladium(0), palladium(II)acetate, and the like. Examples of the ligand are tri(tert-butyl)phosphine, tri(n-hexyl)phosphine, tricyclohexylphosphine, 1,1-bis(diphenylphosphino)ferrocene (abbreviation: DPPF), and the like. Examples of a substance which can be used as the base are organic bases such as sodium-tert-butoxide (abbreviation: tert-BuONa), inorganic bases such as potassium carbonate, and the like. The reaction is preferably performed in a solution, and toluene, xylene, benzene, and the like are given as a solvent that can be used in the reaction. However, the catalyst, ligand, base, and solvent which can be used are not limited to these examples. In addition, the reaction is more preferably performed under an inert atmosphere of nitrogen, argon, or the like.

The case where an Ullmann reaction is used in the synthesis scheme (A-4) is described. As the metal catalyst, a copper catalyst can be used, examples of which include copper(I) iodide and copper(II)acetate. Examples of a substance that can be used as the base include inorganic bases such as potassium carbonate. The reaction is preferably performed in a solution, and examples of the solvent that can be used are 1,3-dimethyl-3,4,5,6-tetrahydro-2(1H)-pyrimidinone (abbreviation: DMPU), toluene, xylene, benzene, and the like. However, the catalyst, ligand, base, and solvent which can be used are not limited to these examples. In addition, the reaction is preferably performed under an inert atmosphere of nitrogen, argon, or the like.

In an Ullmann reaction, because the object of the synthesis can be obtained in a shorter time and a higher yield at a reaction temperature of 100° C. or more, a solvent having a high boiling point such as DMPU or xylene is preferably used. Because the reaction temperature of 150° C. or more is further preferred, DMPU is more preferably used.

Next, as illustrated in a synthesis scheme (A-5), a halogenated stilbene compound (a8), the diarylamine compound (a7), and the diarylamine compound (a7') undergo coupling, so that the stilbene compound represented by the above general formula (G1) can be obtained.

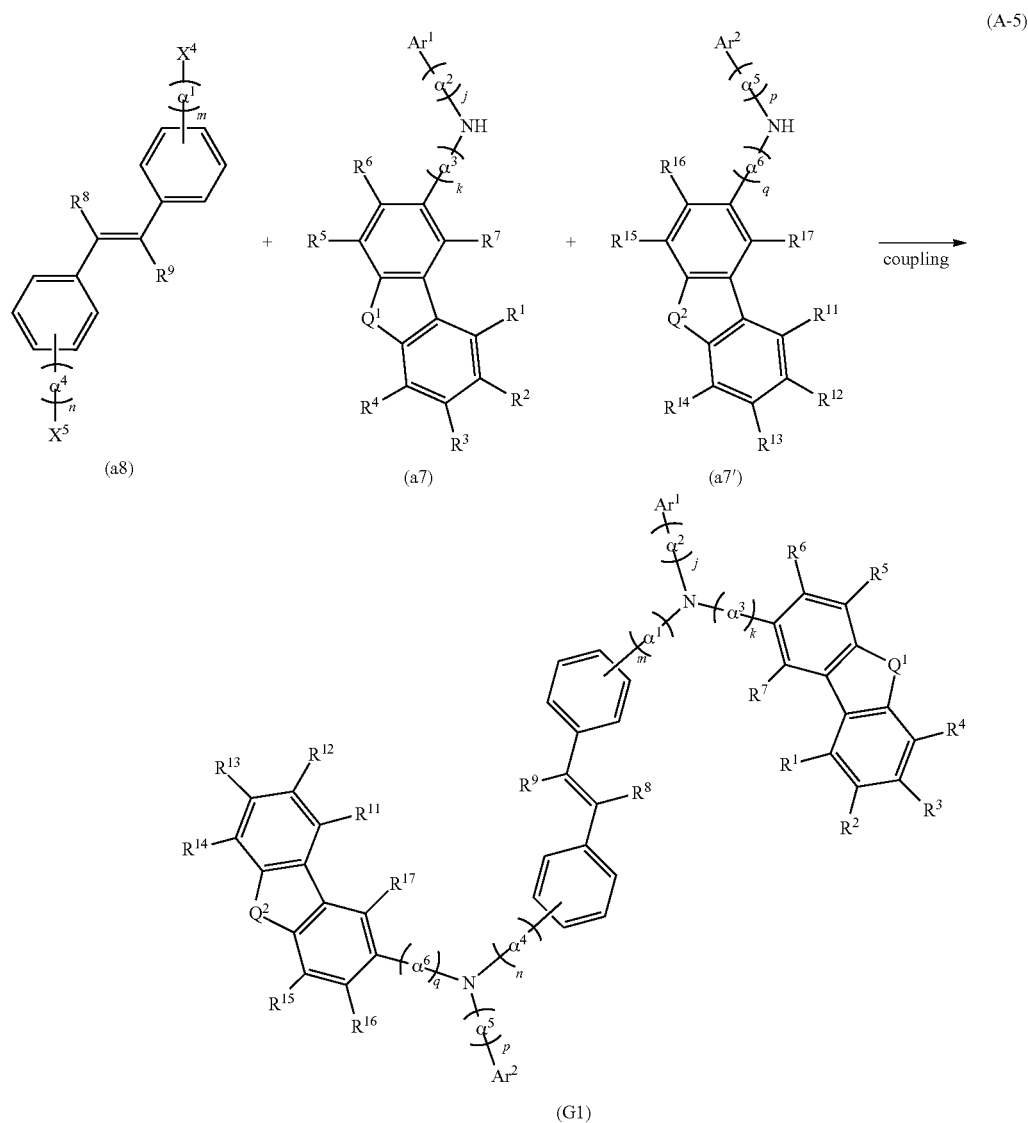

In the synthesis scheme (A-5), $Q^1$ and $Q^2$ separately represent an oxygen atom or a sulfur atom, and $R^1$ to $R^9$ and $R^{11}$ to $R^{17}$ separately represent any one of a hydrogen atom, an alkyl group having 1 to 6 carbon atoms, a substituted or unsubstituted phenyl group, and a substituted or unsubstituted biphenyl group. Further, $\alpha^1$ to $\alpha^6$ separately represent a substituted or unsubstituted phenylene group. Further $Ar^1$ and $Ar^2$ separately represent any one of a substituted or unsubstituted aryl group having 6 to 12 carbon atoms forming a ring, a substituted or unsubstituted dibenzothiophen-2-yl group, and a substituted or unsubstituted dibenzofuran-2-yl group. In addition, j, k, m, n, p, and q separately represent 0 or 1. In addition, $X^4$ and $X^5$ separately represent a halogen, and as the halogen, it is preferable to use chlorine, bromine, or iodine; in terms of higher reactivity, it is preferable to use bromine or even more preferable to use iodine.

In the synthesis scheme (A-5), there are a variety of reaction conditions for the coupling reaction of an aryl compound having a halogen group and an aryl compound having amine (secondary arylamine compound); for example, a synthesis method using a metal catalyst in the presence of a base can be applied. The conditions can be similar to those in the synthesis scheme (A-4), and therefore the synthesis scheme (A-4) is referred to for the details.

In this case, the diarylamine compound (a7) preferably has the same structure as the diarylamine compound (a7') because such a structure can simplify the synthesis and enables the object of the synthesis to be obtained in a high yield.

In the synthesis scheme (A-5), the diarylamine compound (a7) and the diarylamine compound (a7') are reacted with the halogenated stilbene compound (a8) at the same time. However, in the case where the diarylamine compound (a7) and the diarylamine compound (a7') differ in structure, the reaction is preferably caused step by step at different positions because such a reaction results in a higher yield; in this case, one of $X^4$ and $X^5$ in the halogenated stilbene compound (a8) preferably has higher activity than the other of the halogens. For example, when $X^4$ is iodine and $X^5$ is bromine, it is preferable that the diarylamine compound (a7) be selectively reacted with $X^4$ and then the diarylamine compound (a7') and $X^5$ be reacted, because the object of the synthesis can be obtained in a high yield through such a reaction.

In the above synthesis scheme (A-5), the stilbene compound represented by the general formula (G1), which is the object of the synthesis, is synthesized in such a way that the halogenated stilbene compound (a8), the diarylamine compound (a7), and the diarylamine compound (a7') undergo coupling; but this embodiment is not limited to this scheme.

The stilbene compounds of this embodiment exhibit fluorescence and can emit light having a short wavelength. Thus, with the use of the stilbene compounds of this embodiment as a light-emitting material, blue light can be emitted.

The stilbene compounds of this embodiment are also suitable for a host material in a light-emitting layer of a light-emitting element. In other words, a layer is formed including any of the stilbene compounds of this embodiment, and a light-emitting substance (also referred to as a dopant material) having a smaller band gap than the stilbene compound is added to the layer, so that light emission from the dopant material can be obtained. In this case, since the stilbene compound of this embodiment has a wide band gap, it can be used at least for a host material of a fluorescent compound that emits visible light having a wavelength longer than that of green light.

The stilbene compounds of this embodiment have a hole-transport property and therefore can be suitably used for a material of a hole-injection layer or a hole-transport layer of a light-emitting element. Further, a composite material in which any of the stilbene compounds of this embodiment (electron donor) and an electron acceptor (acceptor) are mixed can be used for a hole-injection layer of a light-emitting element. The electron acceptor or the electron donor at least receives or releases electrons with the assistance of an electric field.

Note that this embodiment can be implemented in free combination with any of the other embodiments.

Embodiment 2

In Embodiment 2, a light-emitting element formed using any of the stilbene compounds described in Embodiment 1 is described.

The light-emitting element in Embodiment 2 includes a first electrode which functions as an anode, a second electrode which functions as a cathode, and an EL layer interposed between the first electrode and the second electrode. Note that light emission can be obtained from the light-emitting element in Embodiment 2 when a voltage is applied between the electrodes so that the potential of the first electrode is higher than that of the second electrode.

Figure 1B:
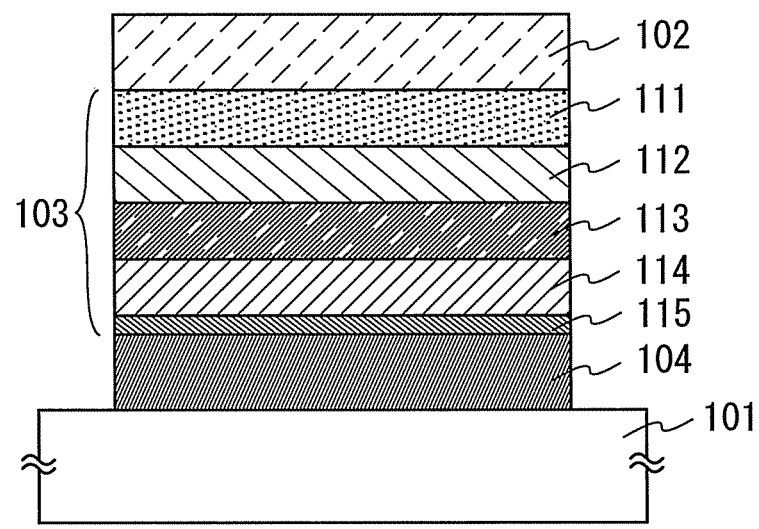

A structure of the light-emitting element in Embodiment 2 is described using FIGS. 1A and 1B. A substrate 101 is used as a support of the light-emitting element. For the substrate 101, glass, quartz, plastics, or the like can be used, for example. Further, a flexible substrate may be used. The flexible substrate is a substrate that can be bent, such as a plastic substrate made of polycarbonate, polyarylate, or polyether sulfone, for example. A film (made of polypropylene, polyester, polyvinyl fluoride, polyvinyl chloride, or the like), an inorganic film formed by evaporation, or the like can also be used.

Although the above substrate 101 may remain in a light-emitting device which is a product utilizing the light-emitting element of Embodiment 2, the substrate is not necessarily remain in an end product and may have a function only as a substrate in a fabrication process of the light-emitting element.

For the first electrode 102 formed over the substrate 101, any of metals, alloys, or electrically conductive compounds, mixtures thereof, and the like which has a high work function (specifically, a work function of 4.0 eV or more) is preferably used. Specific examples are indium oxide-tin oxide (ITO: indium tin oxide), indium oxide-tin oxide containing silicon or silicon oxide, indium oxide-zinc oxide, indium oxide containing tungsten oxide and zinc oxide, graphene, and the like. Other than these, gold (Au), platinum (Pt), nickel (Ni), tungsten (W), chromium (Cr), molybdenum (Mo), iron (Fe), cobalt (Co), copper (Cu), palladium (Pd), titanium (Ti), nitrides of metal materials (e.g., titanium nitride), and the like can be given.

Films of these materials are usually formed by a sputtering method. For example, by a sputtering method, a film of indium oxide-zinc oxide can be formed using a target in which 1 wt % to 10 wt % zinc oxide is added to indium oxide, and a film of indium oxide containing tungsten oxide and zinc oxide can be formed using a target in which 0.5 wt % to 5 wt % tungsten oxide and 0.1 wt % to 1 wt % zinc oxide are added to indium oxide. Alternatively, a vacuum evaporation method, a coating method, an inkjet method, a spin coating method, or the like may be used.

Further, in an EL layer 103 formed over the first electrode 102, a first layer (hole-injection layer) 111 formed in contact with the first electrode 102 is formed using a composite material that facilitates hole injection regardless of work function of the first electrode 102. Therefore, any of a variety of known materials can be used as far as it can serve as an electrode material (e.g., a metal, an alloy, an electrically conductive compound, a mixture thereof, or an element that belongs to Group 1 or Group 2 of the periodic table).

When a layer containing a composite material described later is used, as a material used for the first electrode 102, any of a variety of metals, alloys, electrically conductive compounds, or a mixture thereof can be used regardless of work function. For example, aluminum (Al), silver (Ag), an alloy containing aluminum (e.g., Al—Si), or the like can be used.

Alternatively, it is possible to use any of elements that belong to Group 1 or Group 2 of the periodic table, that is, alkali metals such as lithium (Li) and cesium (Cs), alkaline earth metals such as calcium (Ca) and strontium (Sr), magnesium (Mg), alloys thereof (e.g., Mg—Ag and Al—Li), rare earth metals such as europium (Eu) and ytterbium (Yb), alloys thereof, and the like which are materials having a low work function.

When the first electrode 102 is formed using an alkali metal, an alkaline earth metal, or an alloy thereof, a vacuum evaporation method or a sputtering method can be used. When a silver paste or the like is used, a coating method, an inkjet method, or the like can be used.

In the EL layer 103 formed over the first electrode 102, at least any of the stilbene compounds described in Embodiment 1 is included, and in addition, a known material can be used. As the known material, either a low molecular compound or a high molecular compound can be used. Note that a substance included in the EL layer 103 is not limited to an organic compound, and may be a structure in which an inorganic compound is included as a part.

The EL layer 103 is formed in such a way that a hole-injection layer that includes a substance having a high hole-injection property, a hole-transport layer that includes a substance having a high hole-transport property, a light-emitting layer that includes a light-emitting substance, an electron-transport layer that includes a substance having a high electron-transport property, an electron-injection layer that includes a substance having a high electron-injection property, and the like are combined and stacked as appropriate. Note that the EL layer 103 at least includes a light-emitting layer.

Note that the EL layer 103 illustrated in FIG. 1A includes the first layer (hole-injection layer) 111, a second layer (hole-transport layer) 112, a third layer (light-emitting layer) 113, a fourth layer (electron-transport layer) 114, and a fifth layer (electron-injection layer) 115 which are stacked in that order from the first electrode 102 side.

The first layer (hole-injection layer) 111 which is a hole-injection layer is a layer that includes a substance having a high hole-injection property. Examples of the substance having a high hole-injection property are molybdenum oxide, titanium oxide, vanadium oxide, rhenium oxide, ruthenium oxide, chromium oxide, zirconium oxide, hafnium oxide, tantalum oxide, silver oxide, tungsten oxide, manganese oxide, and the like. Other than these, low molecular organic compounds, for example, phthalocyanine-based compounds such as phthalocyanine (abbreviation: $H_2Pc$) and copper(II) phthalocyanine (abbreviation: CuPc) can be given.

Further, examples of the substance that can be used are aromatic amine compounds which are low molecular organic compounds, such as 4,4',4''-tris(N,N-diphenylamino)triphenylamine (abbreviation: TDATA), 4,4',4''-tris[N-(3-methylphenyl)-N-phenylamino]triphenylamine (abbreviation: MTDATA), 4,4'-bis[N-(4-diphenylaminophenyl)-N-phenylamino]biphenyl (abbreviation: DPAB), 4,4'-bis(N-{4-[N'-(3-methylphenyl)-N'-phenylamino]phenyl}-N-phenylamino)biphenyl (abbreviation: DNTPD), 1,3,5-tris[N-(4-diphenylaminophenyl)-N-phenylamino]benzene (abbreviation: DPA3B), 3-[N-(9-phenylcarbazol-3-yl)-N-phenylamino]-9-phenylcarbazole (abbreviation: 3,6-bis[N-(9-phenylcarbazol-3-yl)-N-phenylamino]-9-phenylcarbazole (abbreviation: PCzPCA2), and 3-[N-(1-naphthyl)-N-(9-phenylcarbazol-3-yl)amino]-9-phenylcarbazole (abbreviation: PCzPCN1). In addition, the stilbene compounds described in Embodiment 1 can also be used.

Other examples of the substance that can be used are high molecular compounds (e.g., oligomers, dendrimers, and polymers), such as poly(N-vinylcarbazole) (abbreviation: PVK), poly(4-vinyltriphenylamine) (abbreviation: PVTPA), poly[N-(4-{N'-[4-(4-diphenylamino)phenyl]phenyl-N'-phenylamino}phenyl)methacrylamide] (abbreviation: PTPDMA), and poly[N,N'-bis(4-butylphenyl)-N,N'-bis(phenyl)benzidine] (abbreviation: Poly-TPD), and high molecular compounds to which acid is added, such as poly(3,4-ethylenedioxythiophene)/poly(styrenesulfonic acid) (PEDOT/PSS), and polyaniline/poly(styrenesulfonic acid) (PAni/PSS).

Alternatively, a composite material in which a substance having a high hole-transport property contains a substance having an acceptor property can be used for the first layer (hole-injecting layer) 111. Note that with use of such a material in which a substance having a high hole-transport property contains a substance having an acceptor property, a material used to form an electrode can be selected regardless of work function. That is, besides a material having a high work function, a material having a low work function can also be used for the first electrode 102. Such a composite material can be formed by co-evaporation of a substance having a high hole-transport property and a substance having an acceptor property. In this specification, the composite material refers to not a material in which two materials are simply mixed but a material in the state where charge transfer between the materials can be caused by a mixture of a plurality of materials.

As the organic compound used for the composite material, any of a variety of compounds, such as aromatic amine compounds, carbazole derivatives, aromatic hydrocarbons, and high molecular compounds (e.g., oligomers, dendrimers, and polymers) can be used. Note that the organic compound used for the composite material is preferably an organic compound having a high hole-transport property. Specifically, a substance having a hole mobility of $10^{-6}$ $cm^2/Vs$ or more is preferably used. Further, other than these substances, a substance that has a property of transporting more holes than electrons may be used. Organic compounds that can be used for the composite material are specifically given below.

Examples of the organic compound that can be used for the composite material are aromatic amine compounds, such as MTDATA, TDATA, DPAB, DNTPD, DPA3B, PCzPCA1, PCzPCA2, PCzPCN1, 4,4'-bis[N-(1-naphthyl)-N-phenylamino]biphenyl (abbreviation: NPB), N,N'-bis(3-methylphenyl)-N,N'-diphenyl-[1,1'-biphenyl]-4,4'-diamine (abbreviation: TPD), and 4-phenyl-4'-(9-phenylfluoren-9-yl)triphenylamine (abbreviation: BPAFLP), and carbazole derivatives, such as 4,4'-di(N-carbazolyl)biphenyl (abbreviation: CBP), 1,3,5-tris[4-(N-carbazolyl)phenyl]benzene (abbreviation: TCPB), 9-[4-(N-carbazolyl)phenyl]-10-phenylanthracene (abbreviation: CzPA), 9-phenyl-3-[4-(10-phenyl-9-anthryl)phenyl]-9H-carbazole (abbreviation: PCzPA), and 1,4-bis[4-(N-carbazolyl)phenyl]-2,3,5,6-tetraphenylbenzene.

Other examples include aromatic hydrocarbon compounds such as 2-tert-butyl-9,10-di(2-naphthyl)anthracene (abbreviation: t-BuDNA), 2-tert-butyl-9,10-di(1-naphthyl)anthracene, 9,10-bis(3,5-diphenylphenyl)anthracene (abbreviation: DPPA), 2-tert-butyl-9,10-bis(4-phenylphenyl) anthracene (abbreviation: t-BuDBA), 9,10-di(2-naphthyl) anthracene (abbreviation: DNA), 9,10-diphenylanthracene (abbreviation: DPAnth), 2-tert-butylanthracene (abbreviation: t-BuAnth), 9,10-bis(4-methyl-1-naphthyl)anthracene (abbreviation: DMNA), 9,10-bis[2-(1-naphthyl)phenyl]-2-tert-butylanthracene, 9,10-bis[2-(1-naphthyl)phenyl]anthracene, and 2,3,6,7-tetramethyl-9,10-di(1-naphthyl)anthracene.

Other examples include aromatic hydrocarbon compounds such as 2,3,6,7-tetramethyl-9,10-di(2-naphthyl)anthracene, 9,9'-bianthryl, 10,10'-diphenyl-9,9'-bianthryl, 10,10'-bis(2-phenylphenyl)-9,9'-bianthryl, 10,10'-bis[(2,3,4,5,6-pentaphenyl)phenyl]-9,9'-bianthryl, anthracene, tetracene, rubrene, perylene, 2,5,8,11-tetra(tert-butyl)perylene, pentacene and coronene, and aromatic hydrocarbon compound having a vinyl group such as 4,4'-bis(2,2-diphenylvinyl)biphenyl (abbreviation: DPVBi) and 9,10-bis[4-(2,2-diphenylvinyl)phenyl]anthracene (abbreviation: DPVPA). In addition, any of the stilbene compounds described in Embodiment 1 can be used.

Further, examples of the substance having an acceptor property which can be used for the composite material are organic compounds, such as 7,7,8,8-tetracyano-2,3,5,6-tetrafluoroquinodimethane (abbreviation: $F_4$-TCNQ) and chloranil, oxides of transition metals, and oxides of metals that belong to any of Groups 4 to 8 in the periodic table, and the like. Specific preferred examples include vanadium oxide, niobium oxide, tantalum oxide, chromium oxide, molybdenum oxide, tungsten oxide, manganese oxide, and rhenium oxide because their electron-acceptor properties are high. Among these, molybdenum oxide is especially preferable since it is stable in the air, has a low hygroscopic property, and is easily treated.

The composite material may be formed using the above-described high molecular compound, such as PVK, PVTPA, PTPDMA, or Poly-TPD, and the above-described substance having an acceptor property, and used for the first layer (hole-injection layer) 111.

The second layer (hole-transport layer) 112 is a layer that includes a substance having a high hole-transport property. Examples of the substance having a high hole-transport property are aromatic amine compounds such as 4,4'-bis[N-(1-naphthyl)-N-phenylamino]biphenyl (abbreviation: NPB), N,N-bis(3-methylphenyl)-N,N-diphenyl-[1,1'-biphenyl]-4,4'-diamine (abbreviation: TPD), 4-phenyl-4'-(9-phenylfluoren-9-yl)triphenylamine (abbreviation: BPAFLP), 4,4'-bis [N-(9,9-dimethylfluoren-2-yl)-N-phenylamino]biphenyl (abbreviation: DFLDPBi), 4,4',4"-tris(N,N-diphenylamino) triphenylamine (abbreviation: TDATA), 4,4',4"-tris[N-(3-methylphenyl)-N-phenylamino]triphenylamine (abbreviation: MTDATA), and 4,4'-bis[N-(spiro-9,9'-bifluoren-2-yl)-N-phenylamino]biphenyl (abbreviation: BSPB), and the like. The substances mentioned here are mainly ones that have a hole mobility of $10^{-6}$ cm$^2$/Vs or more. However, other than these substances, a substance that has a property of transporting more holes than electrons may be used. Any of the stilbene compounds described in Embodiment 1 can also be used. Further, the layer that includes a substance having a high hole-transport property is not limited to a single layer, and may be a stack of two or more layers including any of the above substances.

For the second layer (hole-transport layer) 112, a carbazole derivative such as CBP, CzPA, or PCzPA or an anthracene derivative such as t-BuDNA, DNA, or DPAnth may also be used.

For the second layer (hole-transport layer) 112, a high molecular compound such as poly(N-vinylcarbazole) (abbreviation: PVK) or poly(4-vinyltriphenylamine) (abbreviation: PVTPA) can also be used.

The third layer (light-emitting layer) 113 is a layer that includes a substance having a high light-emitting property. In Embodiment 2, the third layer (light-emitting layer) 113 includes any of the stilbene compounds described in Embodiment 1 as a light-emitting substance.

The third layer (light-emitting layer) 113 may have a structure in which any of the stilbene compounds described in Embodiment 1 is contained as a main component, or dispersed as a dopant material in another substance (host material). Note that in the case where any of the stilbene compounds described in Embodiment 1 is dispersed, the concentration of the stilbene compound is preferably 10% or less of the total in mass ratio. In addition, for the host material, although a known substance can be used, a substance whose lowest unoccupied molecular orbital level (LUMO level) is shallower (the absolute value is smaller) and highest occupied molecular orbital level (HOMO level) is deeper (the absolute value is larger) than those of the stilbene compound described in Embodiment 1 is preferably used. Further, the host material preferably has a higher S1 level than the stilbene compound described in Embodiment 1.

For the host material, any of the following heterocyclic compounds can be used: 2-(4-biphenylyl)-5-(4-tert-butylphenyl)-1,3,4-oxadiazole (abbreviation: PBD), 1,3-bis[5-(p-tert-butylphenyl)-1,3,4-oxadiazol-2-yl]benzene (abbreviation: OXD-7), 3-(biphenyl-4-yl)-4-phenyl-5-(4-tert-butylphenyl)-1,2,4-triazole (abbreviation: TAZ), 2,2',2"-(1,3,5-benzenetriyl)tris(1-phenyl-1H-benzimidazole) (abbreviation: TPBI), bathophenanthroline (abbreviation: BPhen), and bathocuproine (abbreviation: BCP).

Other examples of the substances that can be used include condensed aromatic compounds such as 9-[4-(N-carbazolyl) phenyl]-10-phenylanthracene (abbreviation: CzPA), 9-[4-(3,6-diphenyl-N-carbazolyl)phenyl]-10-phenylanthracene (abbreviation: DPCzPA), 9,10-bis(3,5-diphenylphenyl) anthracene (abbreviation: DPPA), 9,10-di(2-naphthyl) anthracene (abbreviation: DNA), 2-tert-butyl-9,10-di(2-naphthyl)anthracene (abbreviation: t-BuDNA), 9,9'-bianthryl (abbreviation: BANT), 9,9'-(stilbene-3,3'-diyl) diphenanthrene (abbreviation: DPNS), 9,9'-(stilbene-4,4'-diyl)diphenanthrene (abbreviation: DPNS2), and 3,3',3"-(benzene-1,3,5-triyl)tripyrene (abbreviation: TPB3).

As a substance (a host material) in which the light-emitting substance is dispersed, a plurality of kinds of substances can be used. For example, in order to suppress crystallization, a substance such as rubrene which suppresses crystallization, may be further added. In addition, a substance having a high hole-transport property, a substance having a high electron-transport property, or the like can be further added in order to efficiently transfer energy to the light-emitting substance. With a structure in which a substance having a light-emitting property is thus dispersed in another substance, crystallization of the third layer (light-emitting layer) 113 can be suppressed. Further, concentration quenching due to the high concentration of the substrate having a high light-emitting property can also be suppressed.

Among the above-described substances, a substance having an electron-transport property is preferably used so that any of the stilbene compounds described in Embodiment 1 is dispersed therein to form the third layer (light-emitting layer) 113. Specifically, it is also possible to use CzPA, DNA, and t-BuDNA among the above-described metal complexes, heterocyclic compounds, and condensed aromatic compounds, and furthermore, high molecular compounds to be given as a substance which can be used for the fourth layer (electron-transport layer) 114.

An example in which any of the stilbene compounds described in Embodiment 1 is used for a light-emitting substance is described in Embodiment 2, but this does not limit embodiments the present invention. Since the stilbene compounds described in Embodiment 1 have a wide band gap, they can be used at least as a host material for a fluorescent compound that emits visible light having a wavelength longer than that of green light.

Specifically, examples of materials that emit green light are such as N-(9,10-diphenyl-2-anthryl)-N,9-diphenyl-9H-carbazol-3-amine (abbreviation: 2PCAPA), N-[9,10-bis(1,1'-biphenyl-2-yl)-2-anthryl]-N,9-diphenyl-9H-carbazol-3-amine (abbreviation: 2PCABPhA), N-(9,10-diphenyl-2-anthryl)-N,N',N'-triphenyl-1,4-phenylenediamine (abbreviation: 2DPAPA), N-[9,10-bis(1,1'-biphenyl-2-yl)-2-anthryl]-N,N',N'-triphenyl-1,4-phenylenediamine (abbreviation: 2DPABPhA), N-[9,10-bis(1,1'-biphenyl-2-yl)]-N-[4-(9H-carbazol-9-yl)phenyl]-N-phenylanthracen-2-amine (abbreviation: 2YGABPhA), N,N,9-triphenylanthracen-9-amine (abbreviation: DPhAPhA), and the like. Further, examples of materials that emit yellow light are rubrene and 5,12-bis(1,1'-biphenyl-4-yl)-6,11-diphenyltetracene (abbreviation: BPT), and the like. Furthermore, examples of materials that emit red light are N,N,N',N'-tetrakis(4-methylphenyl)tetracene-5,11-diamine (abbreviation: p-mPhTD), 7,14-diphenyl-methylphenyl)acenaphtho[1,2-a]fluoranthene-3,10-diamine (abbreviation: p-mPhAFD), and the like.

Note that the third layer (light-emitting layer) 113 may be formed with a plurality of layers. For example, in the case where a first light-emitting layer and a second light-emitting layer are stacked in this order from the hole-transport layer side to form the third layer (light-emitting layer) 113, it is possible to use a substance having a hole-transport property for a host material of the first light-emitting layer and to use a substance having an electron-transport property for a host material of the second light-emitting layer. It is more preferable to use a material in which the hole-transport property is higher than the electron-transport property for a host material of the first light-emitting layer and to use a material in which the electron-transport property is higher than the hole-transport property for a host material of the second light-emitting layer. With the above structure, a light-emitting region is formed between the first light-emitting layer and the second light-emitting layer, and accordingly an element having higher efficiency can be obtained.

When the light-emitting layer having the structure described above is formed using a plurality of materials, co-evaporation by a vacuum evaporation method can be used, or alternatively an inkjet method, a spin coating method, a dip coating method, or the like with a solution of the materials can be used.

The fourth layer (electron-transport layer) 114 is a layer that includes a substance having a high electron-transport property. For the fourth layer (electron-transport layer) 114, a metal complex such as $Alq_3$, $Almq_3$, $BeBq_2$, BAlq, Znq, ZnPBO, or ZnBTZ, or the like can be used as a low molecular organic compound, for example. In addition to the metal complex, a heterocyclic compound such as PBD, OXD-7, TAZ, TPBI, BPhen, or BCP can be used. The substances mentioned here are mainly substances that have a hole mobility of $10^{-6}$ $cm^2/Vs$ or more. Note that other than the above substances, a substance that has a property of transporting more electrons than holes may be used. Furthermore, the electron-transport layer is not limited to a single layer and may be a stack of two or more layers including any of the above substances.

For the fourth layer (electron-transport layer) 114, a high molecular compound can also be used. For example, poly[(9,9-dihexylfluorene-2,7-diyl)-co-(pyridine-3,5-diyl)] (abbreviation: PF-Py), poly[(9,9-dioctylfluorene-2,7-diyl)-co-(2,2'-bipyridine-6,6'-diyl)] (abbreviation: PF-BPy), or the like can be used.

The fifth layer (electron-injection layer) 115 is a layer that includes a substance having a high electron-injection property. For the fifth layer (electron-injection layer) 115, an alkali metal, an alkaline earth metal, or a compound thereof, such as lithium fluoride (LiF), cesium fluoride (CsF), or calcium fluoride ($CaF_2$), can be used. Alternatively, a layer in which an alkali metal, an alkaline earth metal, magnesium (Mg) or a compound thereof is contained in a substance having an electron-transport property, specifically, a layer in which magnesium (Mg) is contained in $Alq_3$, or the like may be used. Note that in this case, electrons can be more efficiently injected from a second electrode 104.

For the second electrode 104, any of metals, alloys, electrically conductive compounds, and mixtures thereof which have a low work function (specifically, a work function of 3.8 eV or less) or the like is preferably used. Specific examples of such a cathode material are elements that belong to Groups 1 and 2 in the periodic table, i.e., alkali metals such as lithium (Li) and cesium (Cs), and alkaline earth metals such as calcium (Ca) and strontium (Sr), magnesium (Mg), alloys thereof (e.g., Mg—Ag or Al—Li), rare earth metals such as europium (Eu) and ytterbium (Yb), alloys thereof, and the like.

Note that in the case where the second electrode 104 is formed using an alkali metal, an alkaline-earth metal, or an alloy thereof, a vacuum evaporation method or a sputtering method can be used. In the case where a silver paste or the like is used, a coating method, an inkjet method, or the like can be used.

Note that with the fifth layer (electron-injection layer) 115, the second electrode 104 can be formed using any of a variety of electrically conductive materials such as Al, Ag, ITO, graphene, and indium oxide-tin oxide containing silicon or silicon oxide regardless of their work functions. Such a film of a conductive material can be formed by a sputtering method, an inkjet method, a spin coating method, or the like.

Further, as a method of forming the EL layer 103 in which the first layer (hole-injection layer) 111, the second layer (hole-transport layer) 112, the third layer (light-emitting layer) 113, the fourth layer (electron-transport layer) 114, and the fifth layer (electron-injection layer) 115 are stacked in that order, any of a variety of methods can be used regardless of whether the method is a dry process or a wet process. For example, a vacuum evaporation method, an inkjet method, a spin coating method, or the like can be used. Note that different formation methods may be used for the layers.

The second electrode 104 can also be formed by a wet process using a paste of a metal material, in addition to a dry process such as a sputtering method or a vacuum evaporation method.

Since holes mainly flow through the first electrode 102, the first layer (hole-injection layer) 111, the second layer (hole-transport layer) 112, and the third layer (light-emitting layer) 113, each HOMO level (work function for metal) is preferably the same or almost the same in order to reduce the carrier injection barrier between the adjacent layers. Similarly, since electrons mainly flow through the third layer (light-emitting layer) 113, the fourth layer (electron-transport layer) 114, the fifth layer (electron-injection layer) 115, and the second electrode 104, each LUMO level (work function for metal) is preferably the same or almost the same to reduce the carrier injection barrier between the adjacent layers. Each difference is preferably less than or equal to 0.2 eV, more preferably less than or equal to 0.1 eV.

Further, the difference in HOMO level between the second layer (hole-transport layer) 112 and the third layer (light-emitting layer) 113 or the difference in LUMO level between the third layer (light-emitting layer) 113 and the fourth layer (electron-transport layer) 114 are preferably purposely large so that carriers can be confined in the light-emitting layer and thus the light-emitting element has higher efficiency. Note that in this case, if the barrier is too large, the driving voltage increases to be a burden on the element. Therefore, each difference is preferably less than or equal to 0.4 eV, more preferably less than or equal to 0.2 eV.

In the above light-emitting element of this embodiment, current flows due to a potential difference between the first electrode 102 and the second electrode 104, holes and electrons recombine in the EL layer 103, an organic compound having a light-emitting property is brought into an excited state, and when the excited state relaxes to a ground state, the relaxation energy is released as light emission. Then, this light emission is extracted out through one or both of the first electrode 102 and the second electrode 104. Therefore, one or both of the first electrode 102 and the second electrode 104 is/are an electrode having a light-transmitting property.

Figure 2A:
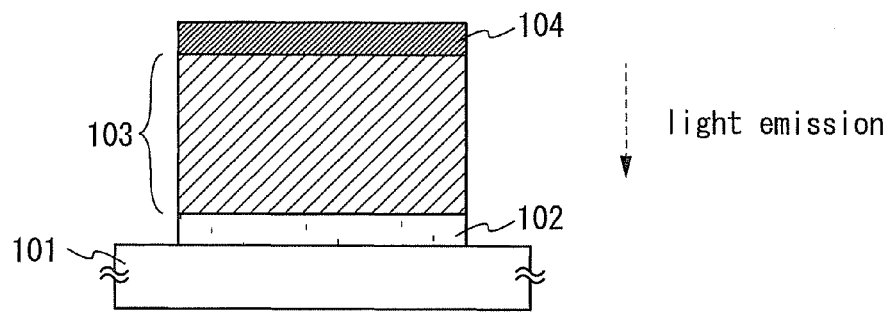
FIGS. 2A to 2C each illustrate a light-emitting element according to one embodiment of the present invention.
Figure 2B:
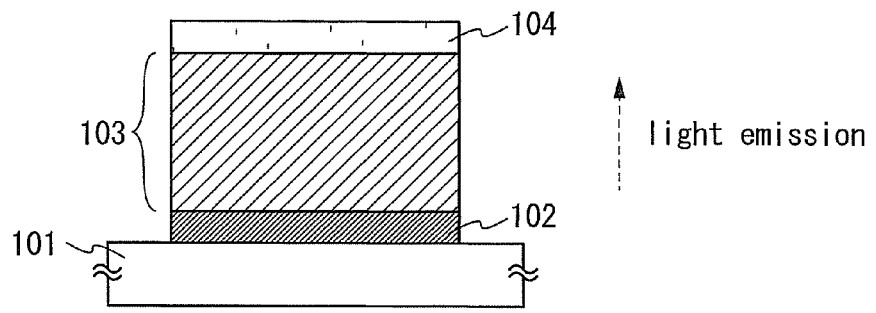
Figure 2C:
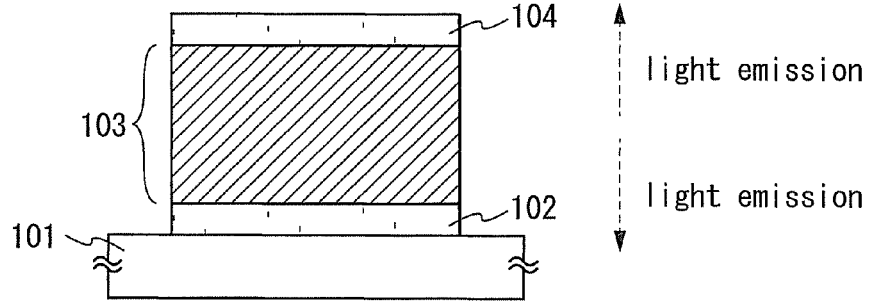

When only the first electrode 102 has a light-transmitting property, as illustrated in FIG. 2A, light generated in the EL layer 103 is extracted from the substrate 101 side through the first electrode 102. When only the second electrode 104 has a light-transmitting property, as illustrated in FIG. 2B, light generated in the EL layer 103 is extracted from the side opposite to the substrate 101 through the second electrode 104. Further, when each of, the first electrode 102 and the second electrode 104 has a light-transmitting property, as illustrated in FIG. 2C, light generated in the EL layer 103 is extracted from both the substrate 101 side and the side opposite to the substrate 101 side through the first electrode 102 and the second electrode 104.

The structure of the layers provided between the first electrode 102 and the second electrode 104 is not limited to the above-described one and may be a structure other than the above as far as at least the third layer (light-emitting layer) 113 which is a light-emitting layer is included.

As illustrated in FIG. 1B, a structure in which the second electrode 104 functioning as a cathode, the EL layer 103, and the first electrode 102 functioning as an anode are stacked in that order over the substrate 101 may be possible. Note that in this case, the EL layer 103 has a structure in which the fifth layer (electron-injection layer) 115, the fourth layer (electron-transport layer) 114, the third layer (light-emitting layer) 113, the second layer (hole-transport layer) 112, the first layer (hole-injection layer) 111, and the first electrode 102 are stacked in that order over the second electrode 104.

Note that by use of the light-emitting element of this embodiment, a passive matrix light-emitting device or an active matrix light-emitting device in which drive of the light-emitting element is controlled by a thin film transistor (TFT) can be fabricated.

In fabrication of an active matrix light-emitting device, there is no particular limitation on the structure of the TFT; for example, a staggered TFT or an inverted staggered TFT can be used as appropriate. Further, a driver circuit formed over a TFT substrate may be formed with both of an n-channel TFT and a p-channel TFT or only either an n-channel TFT or a p-channel TFT. Furthermore, there is no particular limitation on the crystallinity of a semiconductor film used for the TFT; an amorphous semiconductor film may be used, or a crystalline semiconductor film may be used.

As described above, since the light-emitting element described in Embodiment 2 is forted including any of the stilbene compounds of Embodiment 1, element efficiency can be improved and the light-emitting element can be a light-emitting element having a long lifetime.

Embodiment 3

In this embodiment, one mode of a light-emitting element having a structure in which a plurality of light-emitting units (also referred to as EL layers) is stacked (hereinafter, referred to as a stacked-type element) is described with reference to FIGS. 3A and 3B. This light-emitting element is a stacked-type light-emitting element including a plurality of light-emitting units between a first electrode and a second electrode. Each light-emitting unit can have the same structure as the EL layer described in Embodiment 2. In other words, the light-emitting element described in Embodiment 2 is a light-emitting element having one light-emitting unit. In Embodiment 3, a light-emitting element having a plurality of light-emitting units is described.

Figure 3A:
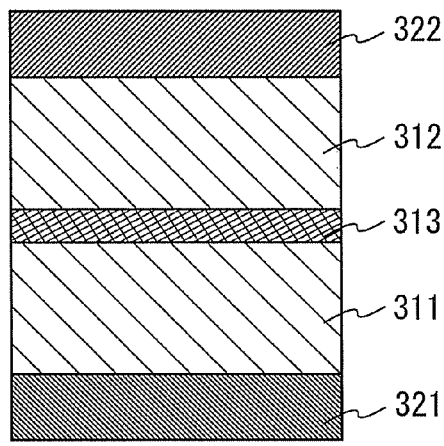
FIGS. 3A and 3B each illustrate a light-emitting element according to one embodiment of the present invention.

In FIG. 3A, a first light-emitting unit 311 and a second light-emitting unit 312 are stacked between a first electrode 321 and a second electrode 322. The first electrode 321 and the second electrode 322 can be the same as those of Embodiment 2. The structures of the first light-emitting unit 311 and the second light-emitting unit 312 may be the same as or different from each other and can be the same as those of Embodiment 2.

A charge generation layer 313 is a layer which injects electrons into one light-emitting unit and injects holes into the other light-emitting unit when a voltage is applied between the first electrode 321 and the second electrode 322. In other words, the charge generation layer 313 may have a structure in which an organic compound having a high hole-transport property and an electron acceptor (acceptor) are included, a structure in which an organic compound having a high electron-transport property and an electron donor (donor) are included, a single layer structure, or a structure in which a plurality of layers is stacked. The structure in which a plurality of layers is stacked is preferably a structure in which a layer that injects holes and a layer that injects electrons are stacked.

For the hole-injection layer, a semiconductor or an insulator, such as molybdenum oxide, vanadium oxide, rhenium oxide, or ruthenium oxide, can be used. Alternatively, a structure in which a substance having an acceptor property is added to a substance having a high hole-transport property may be used. A layer that includes a substance having a high hole-transport property and a substance having an acceptor property includes, as the substance having an acceptor property, 7,7,8,8-tetracyano-2,3,5,6-tetrafluoroquinodimethane (abbreviation: $F_4$-TCNQ) or metal oxide such as vanadium oxide, molybdenum oxide, or tungsten oxide. As the substance having a high hole-transport property, any of a variety of compounds such as aromatic amine compounds, carbazole derivatives, aromatic hydrocarbons, high molecular compounds, oligomers, dendrimers, polymers, and the like can be used. Note that any of the stilbene compounds described in Embodiment 1 can also be used similarly. Note that as the substance having a high hole-transport property, the one having a hole mobility of $10^{-6}$ cm$^2$/Vs or more is preferably used. Further, other than these substances, a substance that has a property of transporting more holes than electrons may be used. Since the composite material including the substance having a high hole-transport property and the substance having an acceptor property is excellent in carrier-injection property and carrier-transport property, low voltage driving and low current driving can be realized.

For the layer that injects electrons, a semiconductor or an insulator, such as lithium oxide, lithium fluoride, or cesium carbonate, can be used. A structure in which the substance having a donor property is added to the substance having a high electron-transport property may be used. As the substance having a donor property, any of alkali metals, alkaline-earth metals, rare-earth metals, metals that belong to Groups 2 and 13 in the periodic table and oxides or carbonates thereof can be used. Specifically, lithium (Li), cesium (Cs), magnesium (Mg), calcium (Ca), ytterbium (Yb), indium (In), lithium oxide, cesium carbonate, or the like is preferably used. An organic compound such as tetrathianaphthacene may be used as the substance having a donor property. As the substance having a high electron-transport property, the one having an electron mobility of $10^{-6}$ cm$^2$/Vs or more is preferably used. Further, other than these substances, a substance that has a property of transporting more electrons than holes may be used. Since the composite material including the substance having a high electron-transport property and the substance having a donor property is excellent in carrier-injection property and carrier-transport property, low-voltage driving and low-current driving can be realized.

Further, the electrode materials described in Embodiment 2 can be used for the charge generation layer 313. For example, a layer that includes a substance having a high hole-transport property and metal oxide and a transparent conductive film may be combined to form the charge-generating layer 313. Note that in view of light extraction efficiency, the charge-generating layer is preferably a layer that has a high light-transmitting property.

In any case, the charge generation layer 313 interposed between the first light-emitting unit 311 and the second light-emitting unit 312 may have any structure as fax as electrons are injected into one of the light-emitting units and holes are injected into the other of the light-emitting units when a voltage is applied between the first electrode 321 and the second electrode 322. For example, the charge generation layer 313 may have any structure as far as electrons are injected into the first light-emitting unit 311 and holes are injected into the second light-emitting unit 312 when a voltage is applied so that the potential of the first electrode is higher than that of the second electrode.

Figure 3B:
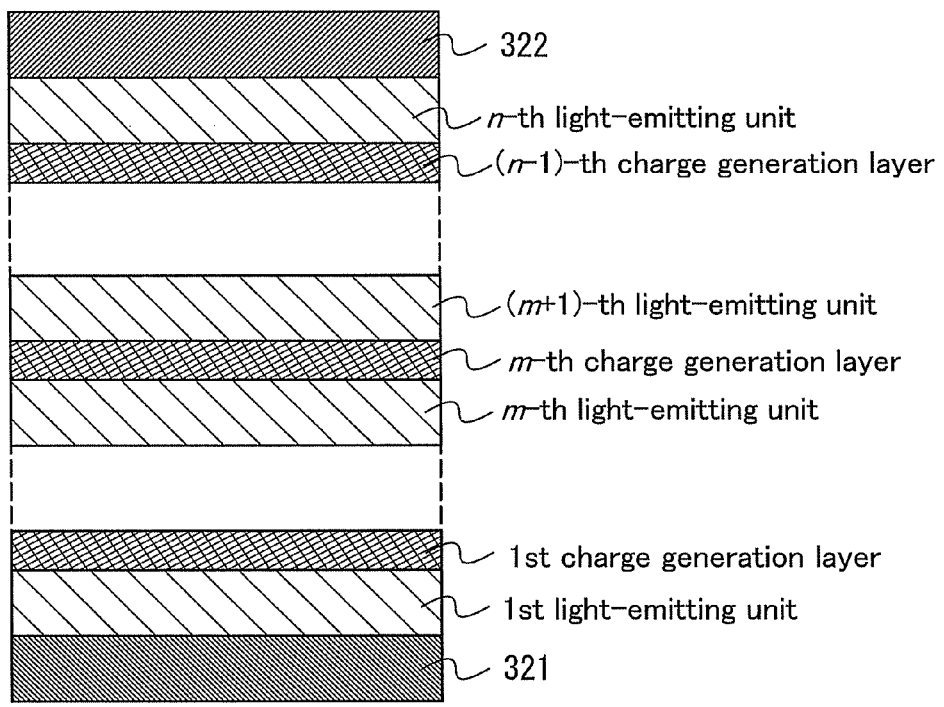

Although the light-emitting element having two light-emitting units is described in this embodiment, the embodiment can similarly be applied to a light-emitting element in which three or more light-emitting units (n light-emitting units) are stacked as illustrated in FIG. 3B. With a plurality of light-emitting units partitioned by the charge-generation layer between a pair of electrodes, as in the light-emitting element according to this embodiment, light emission in a high luminance region can be obtained while current density is kept low; thus, alight-emitting element having a long lifetime can be realized. Further, when the light-emitting element is applied for illumination, since voltage drop due to resistance of an electrode material can be reduced, uniform light emission in a large area can be obtained. Moreover, a light-emitting device that is capable of low-voltage driving and has low power consumption can be realized.

Furthermore, different emission colors of the light-emitting units enable light emission having a desired color to be obtained from the light-emitting element as a whole. For example, the emission colors of first and second light-emitting units are complementary in a light-emitting element having the two light-emitting units, so that the light-emitting element can be made to emit white light as a whole. Note that the term "complementary" means color relationship in which an achromatic color is obtained when colors are mixed. That is, white light emission can be obtained by mixture of light from substances whose emission colors are complementary colors. The same can be applied to a light-emitting element including three light-emitting units. For example, when the emission color of the first light-emitting unit is red, the emission color of the second light-emitting unit is green, and the emission color of the third light-emitting unit is blue, white light emission can be obtained from the light-emitting element as a whole.

Note that this embodiment can be implemented in appropriate combination with any of the other embodiments.

Embodiment 4

In this embodiment, a light-emitting device having a light-emitting element according to Embodiment 2 or Embodiment 3 in a pixel portion is described with reference to FIGS. 4A and 4B. Note that FIG. 4A is a top view illustrating the light-emitting device while FIG. 4B is a cross-sectional view taken along lines A-B and C-D in FIG. 4A.

Figure 4A:
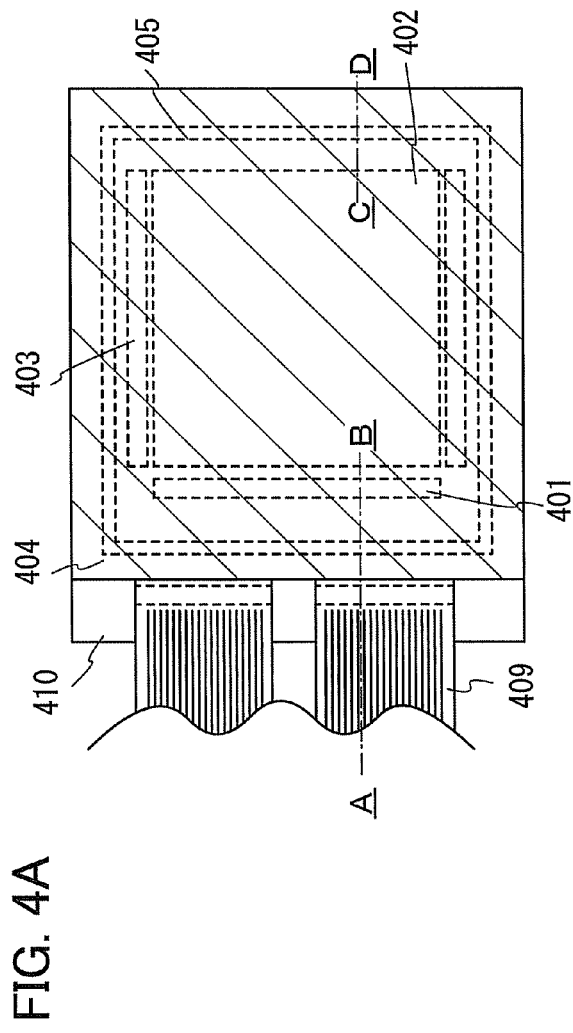
FIGS. 4A and 4B illustrate a light-emitting device according to one embodiment of the present invention.
Figure 4B:
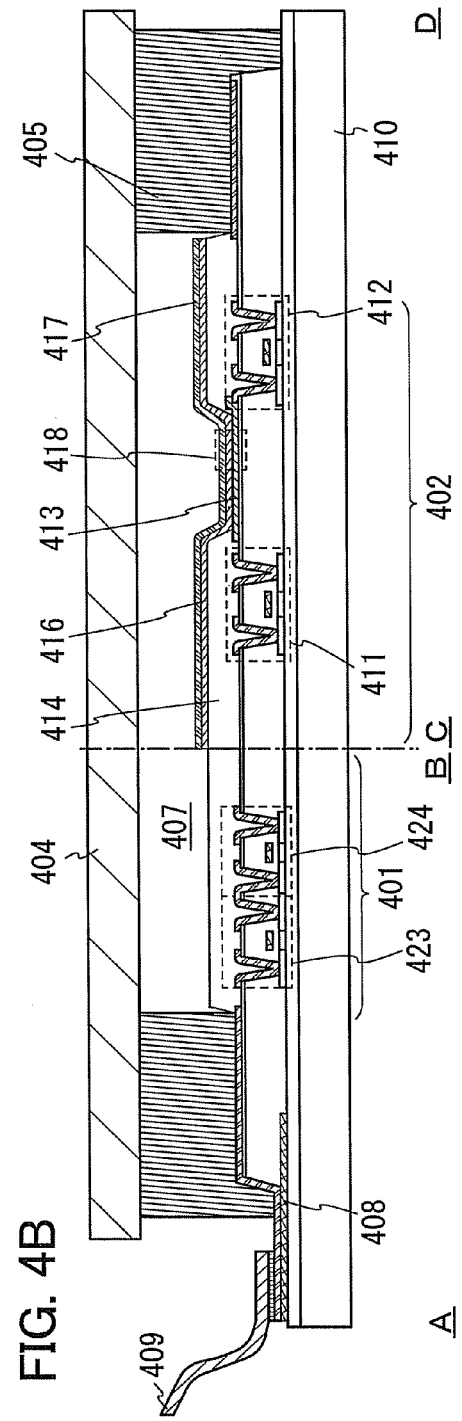

The light-emitting device illustrated in FIG. 4A has a driver circuit portion (source driver circuit 401), a pixel portion 402, a driver circuit portion (gate driver circuit 403), a sealing substrate 404, and a sealing material 405; and a portion surrounded by the sealing material 405 is a space 407.

A lead wiring 408 is a wiring for transmitting signals that are to be input to the source driver circuit 401 and the gate driver circuit 403, and receives a video signal, a clock signal, a start signal, a reset signal, and the like from a flexible printed circuit (FPC) 409 which serves as an external input terminal. Although only the FPC is illustrated here, a printed wiring board (PWB) may be attached to this FPC. The light-emitting device in this specification includes not only a light-emitting device itself but also a light-emitting device to which an FPC or a PWB is attached.

Next, a cross-sectional structure is described with reference to FIG. 4B. The driver circuit portion and the pixel portion are formed over an element substrate 410, and the source driver circuit 401 which is a driver circuit portion and one pixel in the pixel portion 402 are here illustrated. Note that as the source driver circuit 401, a CMOS circuit which includes an n-channel TFT 423 and a p-channel TFT 424 in combination is formed. Further, the driver circuit may be formed with any of a variety of circuits, such as a CMOS circuit, a PMOS circuit, or an NMOS circuit. Although a driver-integrated type in which the driver circuit is formed over the substrate is described in this embodiment, the present invention is not limited to this type and the driver circuit can be funned outside the substrate.

Further, the pixel portion 402 includes a plurality of pixels having a switching TFT 411, a current control TFT 412, and a first electrode 413 electrically connected to a drain of the current control TFT 412. Note that an insulator 414 is formed to cover an end portion of the first electrode 413.

In order to improve coverage, the insulator 414 is preferably formed such that either an upper end portion or a lower end portion of the insulator 414 has a curved surface with a curvature. For example, when positive photosensitive acrylic is used as a material for the insulator 414, only an upper end portion of the insulator 414 can have a curved surface with a radius of curvature (0.2 μm to 3 μm). For the insulator 414, it is also possible to use a negative type photosensitive material that is made insoluble in an etchant by light irradiation or a positive type one that is made soluble in an etchant by light irradiation.

Over the first electrode 413, an EL layer 416 and a second electrode 417 are formed. In this case, as a material used for the first electrode 413, any of a variety of materials such as metals, alloys, and electrically conductive compounds or a mixture thereof can be used. Note that as specific materials, the materials described in Embodiment 2 as a material that can be used for the first electrode can be used.

The EL layer 416 is foamed by any of a variety of methods such as an evaporation method using an evaporation mask, an inkjet method, and a spin coating method. The EL layer 416 has the structure described in Embodiment 2 or Embodiment 3. Further, for another material included in the EL layer 416, any of low molecular compounds and high molecular compounds (including oligomers and dendrimers) may be used. For a material used for the EL layer, an inorganic compound may be used without being limited to an organic compound.

Further, for a material used for the second electrode 417, any of a variety of metals, alloys, and electrically conductive compounds, or a mixture thereof can be used. Among them, any of metals, alloys, electrically conductive compounds, and mixtures thereof which have a low work function (a work function of 3.8 eV or less) or the like is preferably used when the second electrode 417 is used as a cathode. Examples are elements that belong to Group 1 or Group 2 of the periodic table, that is, alkali metals such as lithium (Li) and cesium (Cs), alkaline earth metals such as calcium (Ca) and strontium (Sr), magnesium (Mg), alloys thereof (e.g., Mg—Ag and Al—Li), and the like.

Note that in the case where light generated in the EL layer 416 is transmitted through the second electrode 417, a stack of a metal thin film having a reduced thickness and a transparent conductive film (e.g., indium oxide-tin oxide (ITO), indium oxide-tin oxide containing silicon or silicon oxide, indium oxide-zinc oxide (IZO), indium oxide containing tungsten oxide and zinc oxide, or graphene) can also be used for the second electrode 417.

Further, the sealing substrate 404 is attached to the element substrate 410 with the sealing material 405, so that a light-emitting element 418 is provided in the space 407 enclosed by the element substrate 410, the sealing substrate 404, and the sealing material 405. Note that the space 407 is filled with a filler, and may be filled with an inert gas (such as nitrogen or argon) or the sealing material 405.

Further, an epoxy-based resin is preferably used as the sealing material 405. Preferably, as little moisture and oxygen as possible penetrate such a material. As a material used for the sealing substrate 404, a plastic substrate formed of fiberglass-reinforced plastics (FRP), polyvinyl fluoride (PVF), polyester, acrylic, or the like can be used other than a glass substrate or a quartz substrate.

As described above, the active matrix light-emitting device having the light-emitting element according to Embodiment 2 or Embodiment 3 can be obtained.

Figure 5A:
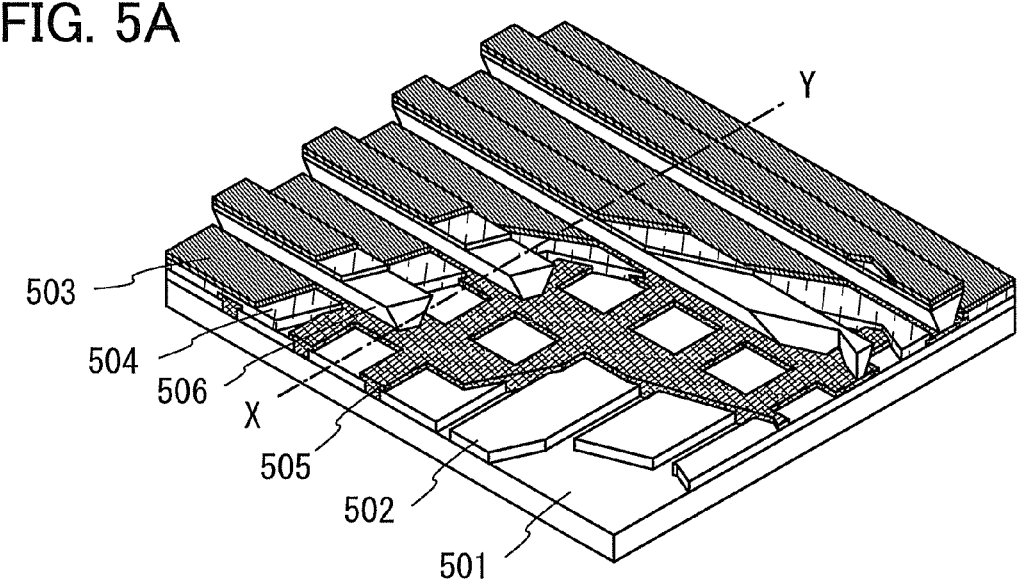
FIGS. 5A and 5B illustrate a light-emitting device according to one embodiment of the present invention.
Figure 5B:
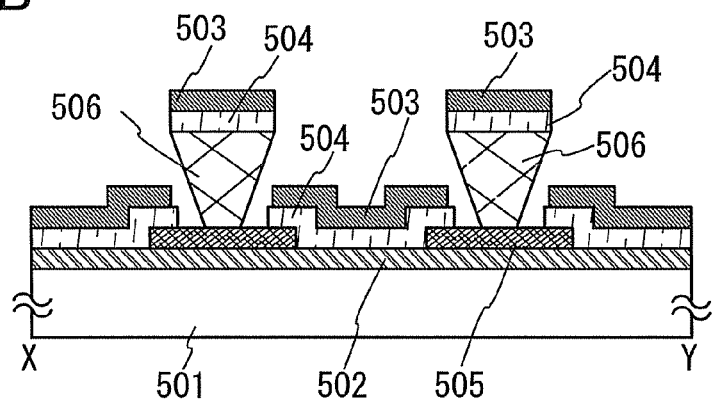

Further, the light-emitting element according to Embodiment 2 or Embodiment 3 can be used not only for the above active matrix light-emitting device but also for a passive matrix light-emitting device. A perspective and cross-sectional views of a passive matrix light-emitting device using the light-emitting element described in the above embodiments are illustrated in FIGS. 5A and 5B. Note that FIG. 5A is the perspective view of the light-emitting device, and FIG. 5B is the cross-sectional view taken along line X-Y of FIG. 5A.

In FIGS. 5A and 5B, an EL layer 504 is provided between a first electrode 502 and a second electrode 503 over a substrate 501. An end portion of the first electrode 502 is covered with an insulating layer 505. In addition, a partition layer 506 is provided over the insulating layer 505. The sidewalls of the partition layer 506 slope so that a distance between both the sidewalls is gradually narrowed toward the surface of the substrate. In other words, a cross section taken along the direction of the short side of the partition layer 506 is trapezoidal, and the base (a side which is in the same direction as a plane direction of the insulating layer 505 and in contact with the insulating layer 505) is shorter than the upper side (a side which is in the same direction as the plane direction of the insulating layer 505 and not in contact with the insulating layer 505). With the partition layer 506 provided in such a way, a defect of a light-emitting element due to static electricity or the like can be prevented.

Thus, the passive matrix light-emitting device having the light-emitting element according to Embodiment 2 or Embodiment 3 can be obtained.

Note that the light-emitting devices described in Embodiment 4 (the active matrix light-emitting device and the passive matrix light-emitting device) are fanned using the light-emitting element described in any of the above embodiments, which has high emission efficiency and a long lifetime, and accordingly a light-emitting device with low power consumption and high reliability can be obtained.

Note that this embodiment can be implemented in appropriate combination with the structure described in any of the other embodiments.

Embodiment 5

Figure 6A:
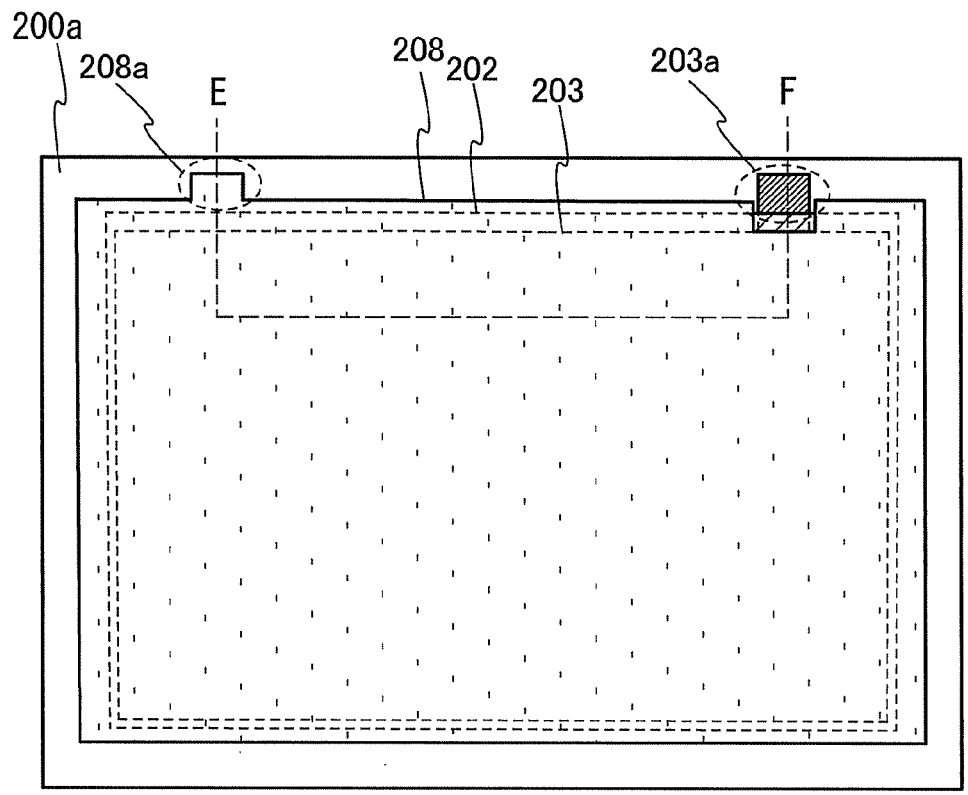
FIGS. 6A and 6B illustrate a light-emitting device according to one embodiment of the present invention.
Figure 6B:
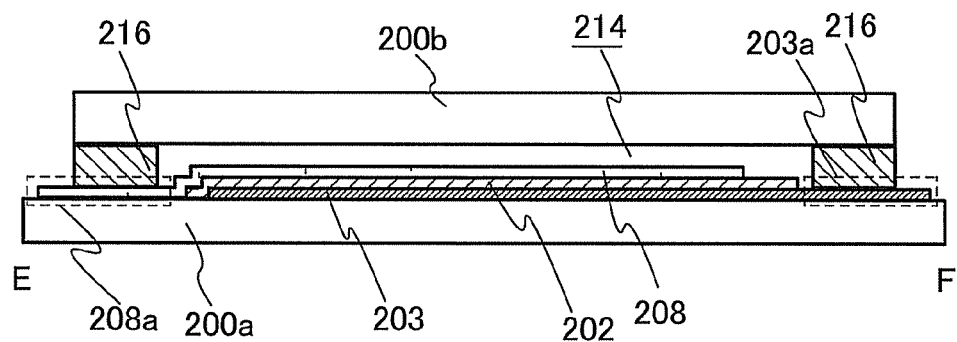

In this embodiment, a light-emitting device including a light-emitting element of Embodiment 2 or Embodiment 3 in a pixel portion is described with reference to FIGS. 6A and 6B. Note that FIG. 6A is a top view illustrating the light-emitting device, and FIG. 6B is a cross-sectional view taken along a line E-F in FIG. 6A. Note also that in FIG. 6A, a second substrate 200b and a sealing material 216 in FIG. 6B are not illustrated.

The light-emitting device illustrated in FIGS. 6A and 6B includes a first substrate 200a, a first electrode 203, an EL layer 202, a second electrode 208, the sealing material 216, and the second substrate 200b. Specifically, the light-emitting device includes the following: the first electrode 203 over the first substrate 200a; the EL layer 202, which covers the first electrode 203 except a connection terminal portion 203a which is part of the first electrode 203; and the second electrode 208, which covers the EL layer 202 without being in contact with the first electrode 203. The first substrate 200a and the second substrate 200b are bonded with the sealing material 216. A portion enclosed by the first substrate 200a, the second substrate 200b, and the sealing material 216 is a space 214. In addition, the connection terminal portion 203a, which is part of the first electrode 203, and a connection terminal portion 208a, which is part of the second electrode 208, are each connected to a connection electrode.

In the light-emitting device illustrated in FIGS. 6A and 6B, the first electrode 203, the EL layer 202, and the second electrode 208 can be based on, respectively, the first electrode 413, the EL layer 416, and the second electrode 417 according to the above embodiment. In addition, the sealing material 216 can also be based on the sealing material 405 according to the above embodiment.

Like the space 407 in the above embodiment, the space 214 is also filled with a filler, which may be an inert gas (e.g., nitrogen or argon), the sealing material 216, a sealing material whose material is different from that of the sealing material 216, or vacuum.

At least either the first substrate 200a or the second substrate 200b has a property of transmitting visible light (hereinafter referred to as a light-transmitting property). As a material of the first substrate 200a and the second substrate 200b, for example, glass, quartz, plastic, or the like can be used. A flexible substrate may be used. As a material of the flexible substrate, a polyester resin such as polyethylene terephthalate (PET) or polyethylene naphthalate (PEN), a polyacrylonitrile resin, a polyimide resin, a polymethyl methacrylate resin, a polycarbonate (PC) resin, a polyethersulfone (PES) resin, a polyamide resin, a cycloolefin resin, a polystyrene resin, a polyamide imide resin, or a polyvinylchloride resin can be used. A substrate in which a glass fiber is impregnated with a resin or a substrate in which an inorganic filler is mixed with an organic resin can be used.

In this embodiment, each of the first substrate 200a and the second substrate 200b has a quadrilateral shape, but there is no limitation to a quadrilateral shape; the first substrate 200a and the second substrate 200b may have a round shape or an elliptical shape, for example. Similarly, a light-emitting surface of the light-emitting element has a quadrilateral shape, but there is no limitation to a quadrilateral shape; the light-emitting element may have a round shape or an elliptical shape, for example.

For a material of the connection electrode, a conductive material can be used; for example, any of a variety of metals, alloys, electrically conductive compounds, and mixtures thereof can be used.

Further, an inorganic insulating layer covering the light-emitting element (a portion where the first electrode 203, the EL layer 202, and the second electrode 208 overlap) may be provided. An inorganic insulating layer may be provided between the first substrate 200a and the light-emitting element. As a material of the inorganic insulating layer, for example, silicon nitride, silicon oxide, alumina, or the like can be used. With the inorganic insulating layer, moisture, impurities, or the like can be prevented from entering the organic compound or metal material included in the light-emitting element from the outside of the light-emitting element.

In the case where the inorganic insulating layer is provided, the second substrate 200b and the sealing material 216 are not necessarily provided, but if the second substrate 200b and the sealing material 216 are provided, moisture, impurities, or the like can be further prevented from entering the organic compound or metal material included in the light-emitting element from the outside of the light-emitting element.

In this embodiment, when light is extracted from the first substrate 200a side, a material having a light-transmitting property is used for the first electrode 203 and the first substrate 200a; when light is extracted from the second substrate 200b side, a material having a light-transmitting property is used for each of the second electrode 208 and the second substrate 200b; or when light is extracted from the first substrate 200a side and the second substrate 200b side, a material having a light-transmitting property is used for each of the first electrode 203, the first substrate 200a, the second electrode 208, and the second substrate 200b.

Note that in this embodiment, an appropriate combination of the structures described in any of the other embodiments can be used.

Embodiment 6

In this embodiment, electronic devices including the light-emitting device described in either of Embodiments 4 and 5 as a part are described. Since a light-emitting element including any of the stilbene compounds described in Embodiment 1 is used for the light-emitting device described in either of Embodiments 4 and 5, the light-emitting device is a light-emitting device having reduced power consumption, and accordingly, electronic devices described in Embodiment 6 can be electronic devices having a display portion having low power consumption, can be electronic devices having low driving voltage, or can be electronic devices having high reliability.

Examples of the electronic devices to which the light-emitting device is applied are television devices (also referred to as TV or television receivers), monitors for computers and the like, cameras such as digital cameras and digital video cameras, digital photo frames, cellular phones (also referred to as portable telephone devices), portable game machines, portable information terminals, audio playback devices, large game machines such as pachinko machines, and the like. Specific examples of these electronic devices and a lighting device are illustrated below.

Figure 7A:
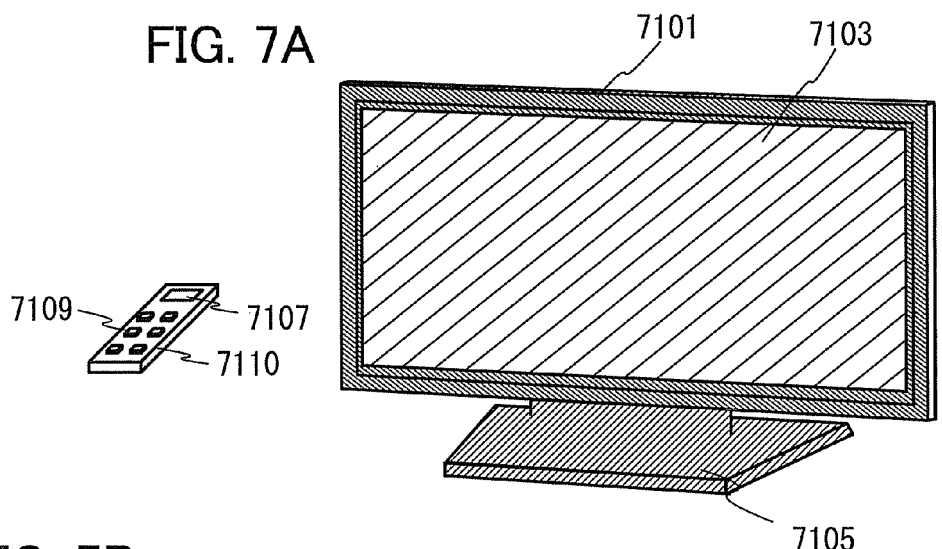
FIGS. 7A to 7D each illustrate an electronic device according to one embodiment of the present invention.

In FIG. 7A, an example of a television device is illustrated. In the television device, a display portion 7103 is incorporated in a housing 7101. In addition, here, the housing 7101 is supported by a stand 7105. The display portion 7103 enables display of images and includes light-emitting elements which are the same as that described in Embodiment 2 or 3 and arranged in a matrix. Since each light-emitting element includes any of the stilbene compounds described in Embodiment 1, the light-emitting elements can be light-emitting elements having high emission efficiency, can be light-emitting elements having low driving voltage, or can be light-emitting elements having high reliability. Accordingly, the television device that has the display portion 7103 including the light-emitting elements can be a television device having reduced power consumption, can be a television device having low driving voltage, or can be a television device having high reliability.

The television device can be operated by an operation switch of the housing 7101 or a separate remote controller 7110. With operation keys 7109 of the remote controller 7110, channels and volume can be controlled and images displayed on the display portion 7103 can be controlled. Furthermore, the remote controller 7110 may be provided with a display portion 7107 for displaying data output from the remote controller 7110.

Note that the television device is provided with a receiver, a modem, and the like. With the receiver, general television broadcasting can be received. Furthermore, when the television device is connected to a communication network by wired or wireless connection via the modem, one-way (from a transmitter to a receiver) or two-way (between a transmitter and a receiver, between receivers, or the like) data communication can be performed.

Figure 7B:
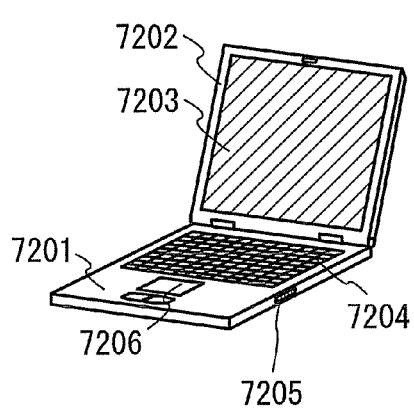

In FIG. 7B, a computer is illustrated, which has a main body 7201, a housing 7202, a display portion 7203, a keyboard 7204, an external connecting port 7205, a pointing device 7206, and the like. Note that this computer is manufactured by using light-emitting elements arranged in a matrix in the display portion 7203, which are the same as that described in Embodiment 2 or 3. Since each light-emitting element includes any of the stilbene compounds described in Embodiment 1, the light-emitting elements can be light-emitting elements having high emission efficiency, can be light-emitting elements having low driving voltage, or can be light-emitting elements having high reliability. Accordingly, the computer that has the display portion 7203 including the light-emitting elements can be a computer having reduced power consumption, can be a computer having low driving voltage, or can be a computer having high reliability.

Figure 7C:
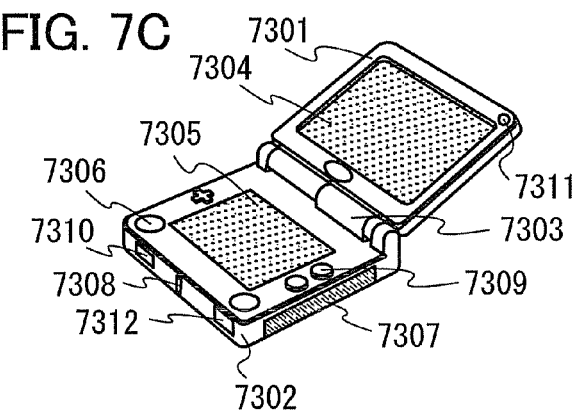

In FIG. 7C, a portable amusement machine is illustrated, which has two housings, a housing 7301 and a housing 7302 connected with a joint portion 7303 so that the portable amusement machine can be opened or folded. A display portion 7304 including light-emitting elements which are the same as that described in Embodiment 2 or 3 and arranged in a matrix is incorporated in the housing 7301, and a display portion 7305 is incorporated in the housing 7302. In addition, the portable amusement machine illustrated in FIG. 7C includes a speaker portion 7306, a recording medium insertion portion 7307, an LED lamp 7308, an input unit (an operation key 7309, a connection terminal 7310, a sensor 7311 (a sensor having a function of measuring force, displacement, position, speed, acceleration, angular velocity, rotational frequency, distance, light, liquid, magnetism, temperature, chemical substance, sound, time, hardness, electric field, current, voltage, electric power, radiation, flow rate, humidity, gradient, oscillation, odor, or infrared rays), or a microphone 7312), and the like. It is needless to say that the structure of the portable amusement machine is not limited to the above as far as the display portion including light-emitting elements which are the same as that described in Embodiment 2 or 3 and arranged in a matrix is used as at least either the display portion 7304 or the display portion 7305, or both, and the structure can include other accessories as appropriate. The portable amusement machine illustrated in FIG. 7C has a function of reading out a program or data stored in a storage medium to display it on the display portion, and a function of sharing information with another portable amusement machine by wireless communication. Note that the portable amusement machine illustrated in FIG. 7C can have a variety of functions without limitation to the above. The portable amusement machine including the above-described display portion 7304 can be a portable amusement machine having reduced power consumption because the light-emitting elements used in the display portion 7304 have high emission efficiency by including any of the stilbene compounds described in Embodiment 1. Further, the portable amusement machine can also be a portable amusement machine having low driving voltage because the light-emitting elements used in the display portion 7304 have low driving voltage by including any of the stilbene compounds described in Embodiment 1. Furthermore, the portable amusement machine can also be a portable amusement machine having high reliability because the light-emitting elements used in the display portion 7304 have high reliability by including any of the stilbene compounds described in Embodiment 1.

Figure 7D:
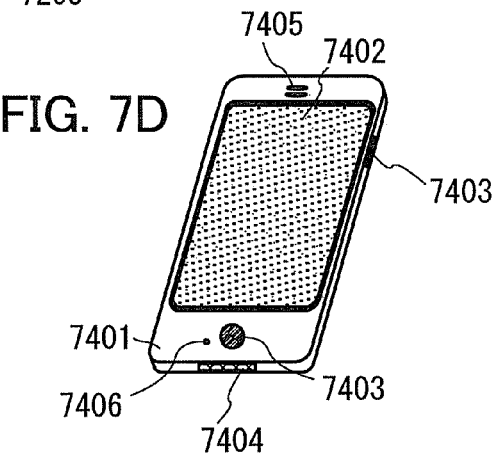

In FIG. 7D, an example of a cellular phone is illustrated. The cellular phone 7400 is provided with operation buttons 7403, an external connection port 7404, a speaker 7405, a microphone 7406, and the like, in addition to a display portion 7402 incorporated in a housing 7401. Note that the cellular phone has the display portion 7402 including light-emitting elements which are the same as that described in Embodiment 2 or 3 and arranged in a matrix. Since each light-emitting element includes any of the stilbene compounds described in Embodiment 1, the light-emitting elements can be light-emitting elements having high emission efficiency, can be light-emitting elements having low driving voltage, or can be light-emitting elements having high reliability. Accordingly, the cellular phone that has the display portion 7402 including the light-emitting elements can be a cellular phone having reduced power consumption, can be a cellular phone having low driving voltage, or can be a cellular phone having high reliability.

When the display portion 7402 of the cellular phone illustrated in FIG. 7D is touched with a finger or the like, data can be input into the cellular phone. In this case, operations such as making a phone call and writing e-mail can be performed by touch on the display portion 7402 with a finger or the like.

There are mainly three screen modes of the display portion 7402. The first mode is a display mode mainly for displaying an image. The second mode is an input mode mainly for inputting information such as a character. The third mode is a display-and-input mode in which two modes of the display mode and the input mode are mixed.

For example, in the case where a phone call is made or e-mail is written, the character input mode mainly for inputting a character is selected for the display portion 7402 so that a character displayed on a screen can be input. In this case, it is preferable to display a keyboard or number buttons on almost the entire screen of the display portion 7402.

When a detection device including a sensor for detecting inclination, such as a gyroscope or an acceleration sensor, is provided inside the cellular phone, display on the screen of the display portion 7402 can be automatically changed by determining the orientation of the cellular phone (whether the cellular phone is placed horizontally or vertically for a landscape mode or a portrait mode).

The screen modes are switched by touch on the display portion 7402 or operation with the operation buttons 7403 of the housing 7401. The screen modes can also be switched depending on the kinds of images displayed on the display portion 7402. For example, when a signal for an image displayed on the display portion is data of moving images, the screen mode is switched to the display mode; when the signal is text data, the screen mode is switched to the input mode.

Moreover, in the input mode, if a signal detected by an optical sensor in the display portion 7402 is detected and the input by touch on the display portion 7402 is not performed during a certain period, the screen mode may be controlled so as to be switched from the input mode to the display mode.

The display portion 7402 can function as an image sensor. For example, an image of a palm print, a fingerprint, or the like is taken by touch on the display portion 7402 with the palm or the finger, so that personal authentication can be performed. Furthermore, by use of a backlight or a sensing light source that emits a near-infrared light for the display portion, an image of a finger vein, a palm vein, or the like can also be taken.

As described above, the application range of the light-emitting device having the light-emitting element according to Embodiment 2 or 3 which includes any of the stilbene compounds described in Embodiment 1 is extremely wide, and this light-emitting device can be applied to electronic devices in a variety of fields. By use of any of the stilbene compounds described in Embodiment 1, it is possible to obtain an electronic device having reduced power consumption, an electronic device having low driving voltage, or an electronic device having high reliability.

Moreover, the light-emitting device described in Embodiment 5 can also be used for a lighting device. One mode of application of the light-emitting device described in Embodiment 5 to a lighting device is described with reference to FIG. 8.

Figure 8:
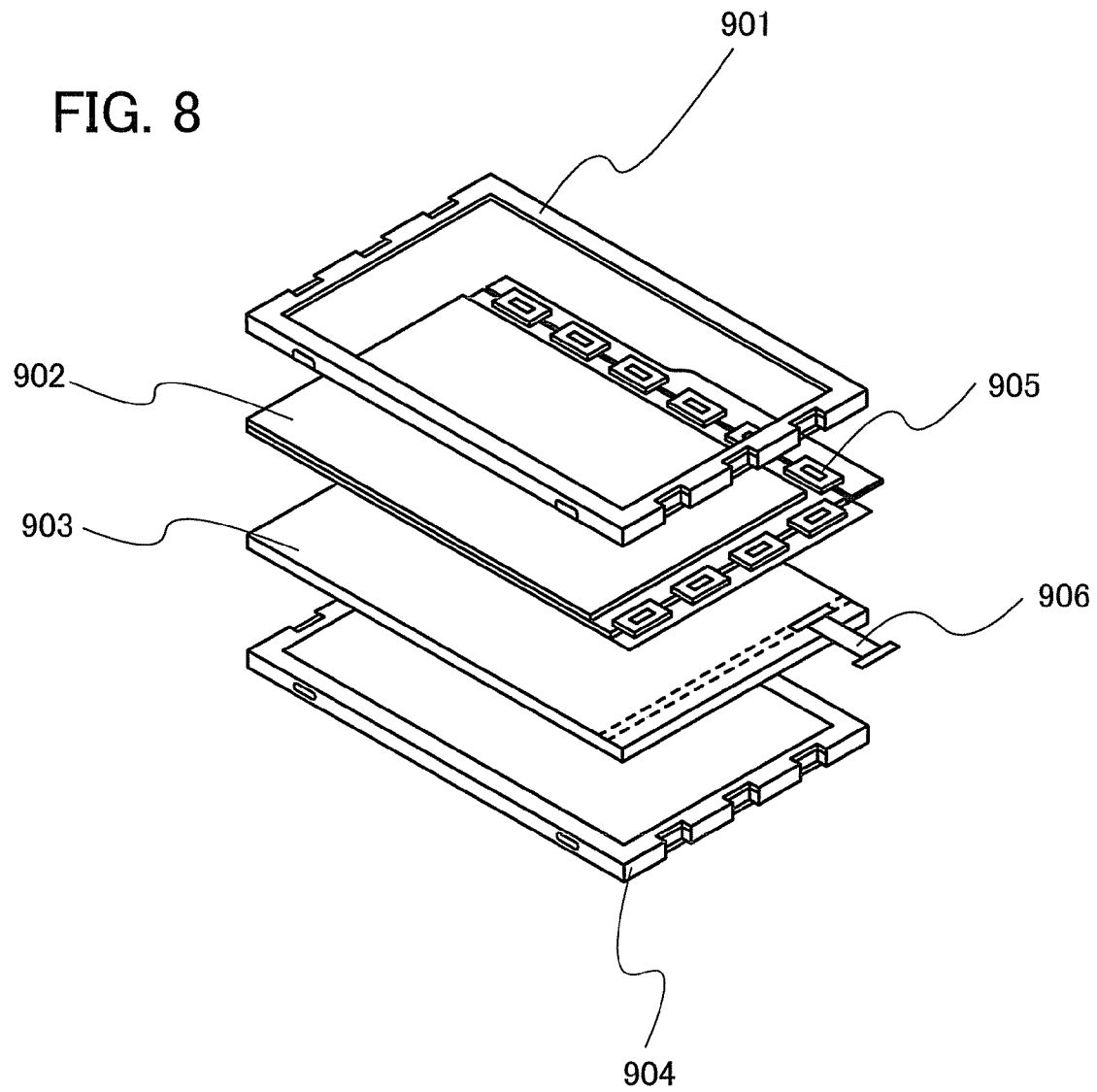
FIG. 8 illustrates an electronic device according to one embodiment of the present invention.

In FIG. 8, an example of a liquid crystal display device using the light-emitting device described in Embodiment 5 for a backlight is illustrated. The liquid crystal display device illustrated in FIG. 8 includes a housing 901, a liquid crystal layer 902, a backlight 903, and a housing 904. The liquid crystal layer 902 is connected to a driver IC 905. The light-emitting device described in Embodiment 5 is used in the backlight 903, to which a current is supplied through a terminal 906.

The light-emitting device described in Embodiment 5 is used for the backlight of the liquid crystal, display device, and thus a backlight having reduced power consumption can be obtained. In addition, the light-emitting device described in Embodiment 5 is a planar-emission lighting device and can be a larger-area device; therefore, the backlight can be a larger-area backlight, and the liquid crystal display device can also be a larger-area device. Furthermore, the light-emitting device described in Embodiment 5 is thin; accordingly, the display device can also be thinner.

Figure 9:
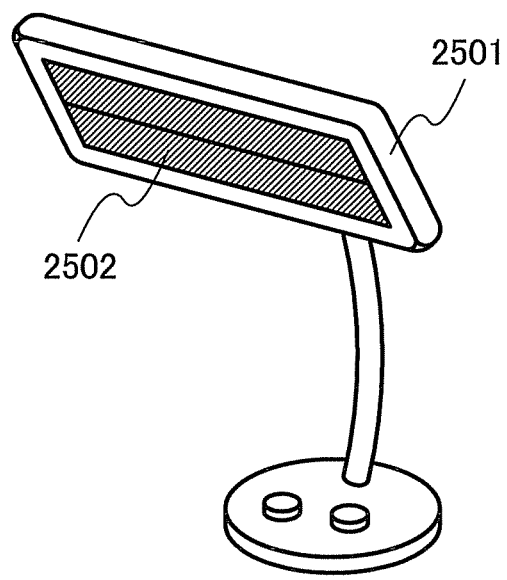
FIG. 9 illustrates a lighting device according to one embodiment of the present invention.

In FIG. 9, an example in which the light-emitting device described in Embodiment 5 is used for a table lamp which is a lighting device is illustrated. The table lamp illustrated in FIG. 9 includes a housing 2501 and a light source 2502, and the light-emitting device described in Embodiment 5 is used for the light source 2502.

Figure 10:
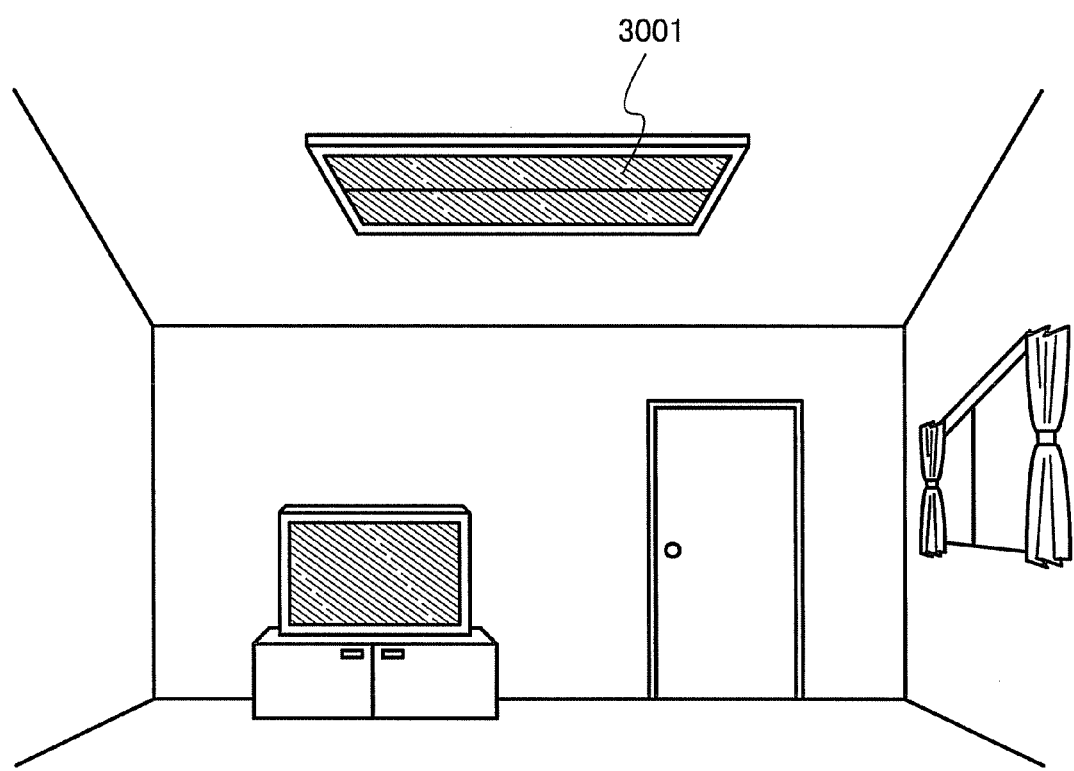
FIG. 10 illustrates a lighting device according to one embodiment of the present invention.

In FIG. 10, an example in which the light-emitting device described in Embodiment 5 is used for an indoor lighting device 3001 is illustrated. Since the light-emitting device described in Embodiment 5 has reduced power consumption, a lighting device that has reduced power consumption can be obtained. Further, since the light-emitting device described in Embodiment 5 can have a large area, the light-emitting element can be used for a large-area lighting device. Furthermore, the light-emitting device described in Embodiment 5 is thin, and accordingly, can be used for a lighting device having a reduced thickness.

Figure 11:
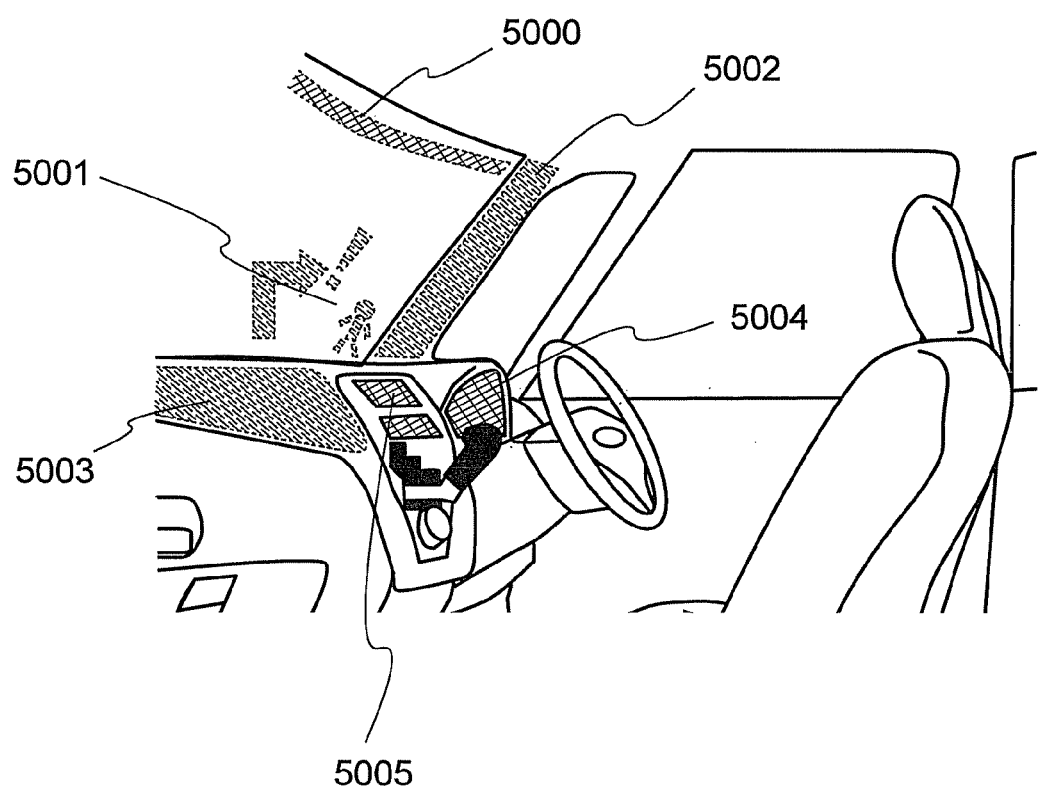
FIG. 11 illustrates in-vehicle display devices.

The light-emitting device described in Embodiment 5 can also be used for an automobile windshield or dashboard. One mode in which the light-emitting device described in Embodiment 5 are used for an automobile windshield and an automobile dashboard is illustrated in FIG. 11. Displays 5000 to 5005 each include the light-emitting device described in Embodiment 5.

The display 5000 and the display 5001 are display devices which are provided in the automobile windshield and in which the light-emitting device described in Embodiment 5 are incorporated. The light-emitting device described in Embodiment 5 can be formed into so-called see-through display devices, through which the opposite side can be seen, by including a first electrode and a second electrode formed with electrodes having a light-transmitting property. Such see-through display devices can be provided even in the automobile windshield, without hindering the vision. Note that in the case where a transistor for driving the light-emitting element is provided, a transistor having a light-transmitting property, such as an organic transistor using an organic semiconductor material or a transistor using an oxide semiconductor, is preferably used.

The display 5002 is a display device provided in a pillar portion. The display 5002 can compensate for the view hindered by the pillar portion by showing an image taken by an imaging element provided in the automobile body. Similarly, the display 5003 provided in the dashboard can compensate for the view hindered by the automobile body by showing an image taken by an imaging element provided in the outside of the automobile body, which leads to elimination of blind areas and enhancement of safety. Showing an image so as to compensate for the area which a driver cannot see, makes it possible for the driver to confirm safety easily and comfortably.

The display 5004 and the display 5005 can provide a variety of kinds of information such as information of navigation, speedometer, tachometer, mileage (travel distance), fuel meter, gearshift indicator, and air condition. The content or layout of the display can be changed freely by a user as appropriate. Further, such information can also be shown in the displays 5000 to 5003.

By including any of the stilbene compounds described in Embodiment 1, the light-emitting device described in Embodiment 5 has low driving voltage or low power consumption, and even when many large screens are provided, load on a battery can be reduced, which provides comfortable use.

EXAMPLE 1

This example illustrates an example of a method of synthesizing 4,4'-bis[N-(dibenzofuran-2-yl)-N-phenylamino] stilbene (abbreviation: FrA2S) represented by the structural formula (100) in Embodiment 1.

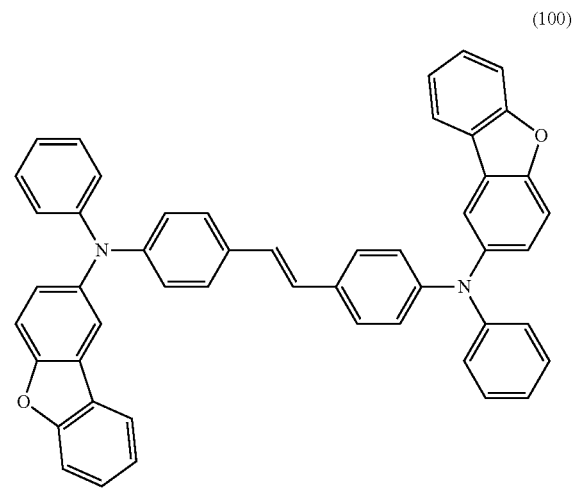 [SMILES: C(=C\c1ccc(N(c2ccccc2)c2ccc3oc4ccccc4c3c2)cc1)/c1ccc(N(c2ccccc2)c2ccc3oc4ccccc4c3c2)cc1]

(100)

Step 1: Method of Synthesizing 2-Iododibenzofuran

In a 500 mL three-neck flask was put a suspension of 8.4 g (50 mmol) of dibenzofuran, 6.2 g (25 mmol) of iodine, 5.7 g (25 mmol) of orthoperiodic acid, 150 mL of glacial acetic acid, 30 mL of water, and 500 μL of sulfuric acid, and the suspension was heated and stirred at 60° C. for 4.5 hours to cause a reaction.

After the reaction, the reaction mixture was further stirred at room temperature for 16 hours. The generated precipitate was collected by filtration, and this obtained residue was dissolved in 150 mL of toluene. Then, the solution was washed with water three times. Magnesium sulfate was added to the toluene solution to adsorb moisture.

This solution was filtered, and the obtained filtrate was concentrated. Then, hexane was added thereto, and the mixture was irradiated with ultrasonic waves. The generated solid was collected by filtration and dried to give 11.3 g of a white powder in 77% yield, which was the object of the synthesis. A reaction scheme of the above synthesis method is illustrated in (B-1) below.

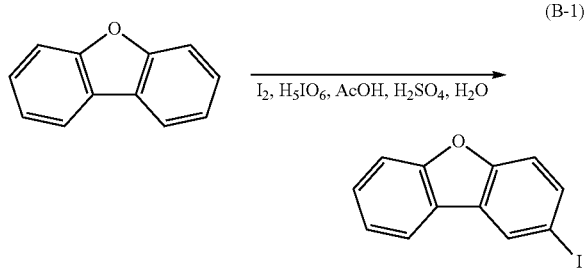

The compound obtained in Step 1 above was subjected to nuclear magnetic resonance (NMR) spectroscopy. The measurement data are shown below.

$^1$H NMR (CDCl$_3$, 300 MHz): δ (ppm)=7.33-7.38 (m, 2H), 7.48 (dt, J=1.5 Hz, 8.4 Hz, 1H), 7.56 (d, J=8.1 Hz, 1H), 7.72 (dd, J=2.1 Hz, 8.4 Hz, 1H), 7.95 (d, J=7.8 Hz, 1H), 8.27 (d, J=1.5 Hz, 1H).

The measurement results confirmed 2-iododibenzofuran, which was the object of the synthesis, was obtained.

Step 2: Method of Synthesizing N-(Dibenzofuran-2-yl)-phenylamine (Abbreviation: FrA)

Into a 100 mL three-neck flask were placed 4.5 g (15 mmol) of 2-iododibenzofuran, 2.0 g (20 mmol) of aniline, 45 mg (0.1 mmol) of bis(dibenzylideneacetone)palladium(0), and 3.0 g (30 mmol) of sodium-tert-butoxide (abbreviation: tert-BuONa), and 30 mL of dehydrated xylene was added. Then, deaeration was performed for 3 minutes until a bubble ceased to appear. To this suspension, 0.5 mL (0.3 mmol) of tri-tert-butylphosphine (a 10 wt % hexane solution) was added, and the mixture was heated and stirred at 120° C. for 5 hours in a nitrogen atmosphere to cause a reaction.

About 200 mL of toluene was added to this reaction suspension, and the mixture was filtered through Florisil (produced by Wako Pure Chemical Industries, Ltd., Catalog No. 540-00135), alumina, and Celite (produced by Wako Pure Chemical Industries, Ltd., Catalog No. 531-16855). The obtained filtrate was washed with water, and magnesium sulfate was added thereto to adsorb moisture.

This suspension was further filtered through Florisil, alumina, and Celite, and the obtained filtrate was concentrated. Then, methanol was added thereto, and the mixture was irradiated with ultrasonic waves. The generated solid was collected by filtration and dried to give 1.6 g of a white powder in 39% yield, which was the object of the synthesis. A reaction scheme of the above synthesis method is illustrated in (B-2) below.

The Rf values of the object of the synthesis, 2-iododibenzofuran, and aniline were respectively 0.28, 0.59, and 0.07, which were found by silica gel thin layer chromatography (TLC) (ethyl acetate:hexane (1:10) as the developing solvent).

The compound obtained in Step 2 above was subjected to nuclear magnetic resonance (NMR) spectroscopy. The measurement data are shown below.

$^1$H NMR (CDCl$_3$, 300 MHz): δ (ppm)=5.80 (s, 1H), 6.94-7.68 (m, 10H), 8.99 (d, J=7.8 Hz, 1H), 8.11 (s, 1H).

The measurement results confirmed that N-(dibenzofuran-2-yl)-phenylamine (abbreviation: FrA), which was the object of the synthesis, was obtained.

Step 3: Method of Synthesizing 4,4'-bis[N-(dibenzofuran-2-yl)-N-phenylamino]stilbene (Abbreviation: FrA2S In a 50 mL three-neck flask, 1.0 g (4.2 mmol) of (dibenzofuran-2-yl)-phenylamine, 680 mg (2.0 mmol) of 4,4'-dibromostilbene, 23 mg (40 μmol) of bis(dibenzylideneacetone)palladium(0), 1.0 g (10 mmol) of sodium-tert-butoxide (abbreviation: tert-BuONa), and 20 mL of dehydrated xylene were subjected to deaeration for 3 minutes until a bubble ceased to appear. To this suspension, 100 μL (50 μmol) of tri-tert-butylphosphine (a 10 wt % hexane solution) was added, and the mixture was heated and stirred at 120° C. for 5.5 hours in a nitrogen atmosphere to cause a reaction.

About 200 mL of toluene was added to this reaction suspension, and the mixture was filtered through Florisil, alumina, and Celite. The obtained filtrate was washed with water, and magnesium sulfate was added thereto to adsorb moisture.

This suspension was further filtered through Florisil, alumina, and Celite, and the obtained filtrate was concentrated. Then, acetone and methanol were added thereto, and the mixture was irradiated with ultrasonic waves. The generated solid was collected by filtration and dried to give 900 mg of a pale yellow powder in 79% yield, which was the object of the synthesis. A reaction scheme of the above synthesis method is illustrated in (B-3) below.

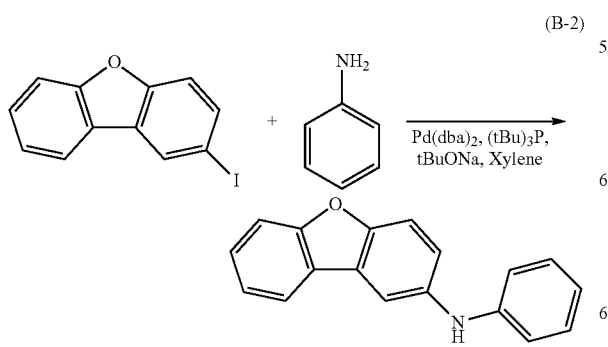

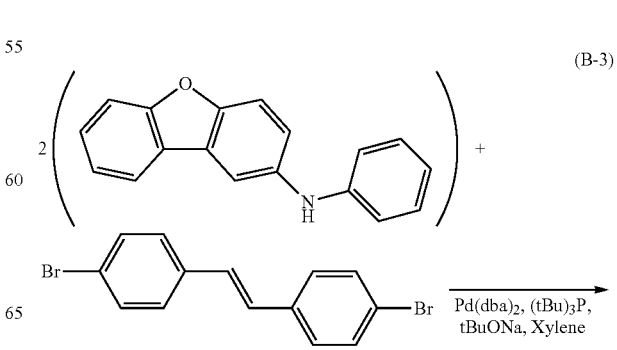

-continued

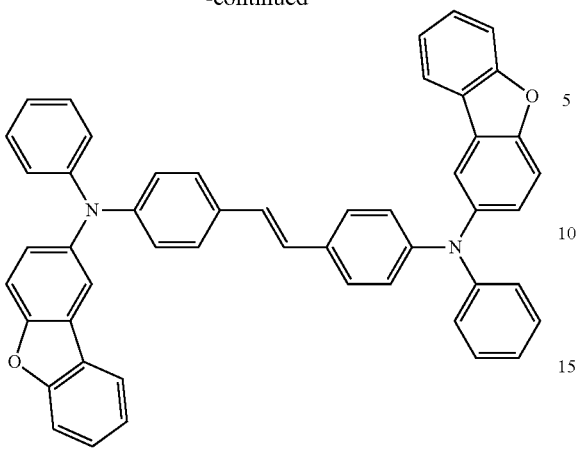

The Rf values of the object of the synthesis, 4,4'-dibromostilbene, and (dibenzofuran-2-yl)-phenylamine were respectively 0.37, 0.62, and 0.31, which were found by silica gel thin layer chromatography (TLC) (ethyl acetate:hexane (1:10) as the developing solvent).

The compound obtained in Step 3 above was subjected to nuclear magnetic resonance (NMR) spectroscopy. The measurement data are shown below.

$^1$H NMR (CDCl$_3$, 300 MHz): δ (ppm)=6.96-7.14 (m, 12H), 7.24-7.57 (m, 18H), 7.74 (d, j=2.1 Hz, 2H), 7.82 (d, j=7.8 Hz, 2H).

The measurement results confirmed that the 4,4'-bis[N-(dibenzofuran-2-yl)-N-phenylamino]stilbene (abbreviation: FrA2S), which was the object of the synthesis, was obtained.

The molecular weight of the above compound was measured with a GC-MS detector (ITQ1100 ion trap GC-MS system, manufactured by Thermo Fisher Scientific K.K.). As a result, a main peak at a molecular weight of 694.14 was detected (in the EI+ mode), and thus it is confirmed that 4,4'-bis[N-(dibenzofuran-2-yl)-N-phenylamino]stilbene (abbreviation: FrA2S), which was the object of the synthesis, was obtained.

Figure 12A:
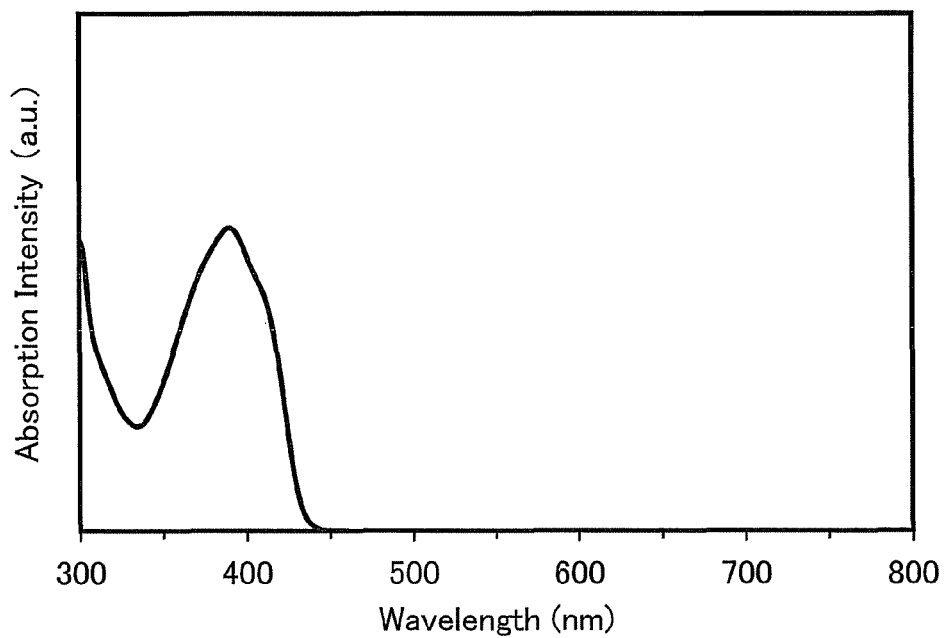
FIGS. 12A and 12B show an absorption and emission spectra of FrA2S in a toluene solution of FrA2S.
Figure 12B:
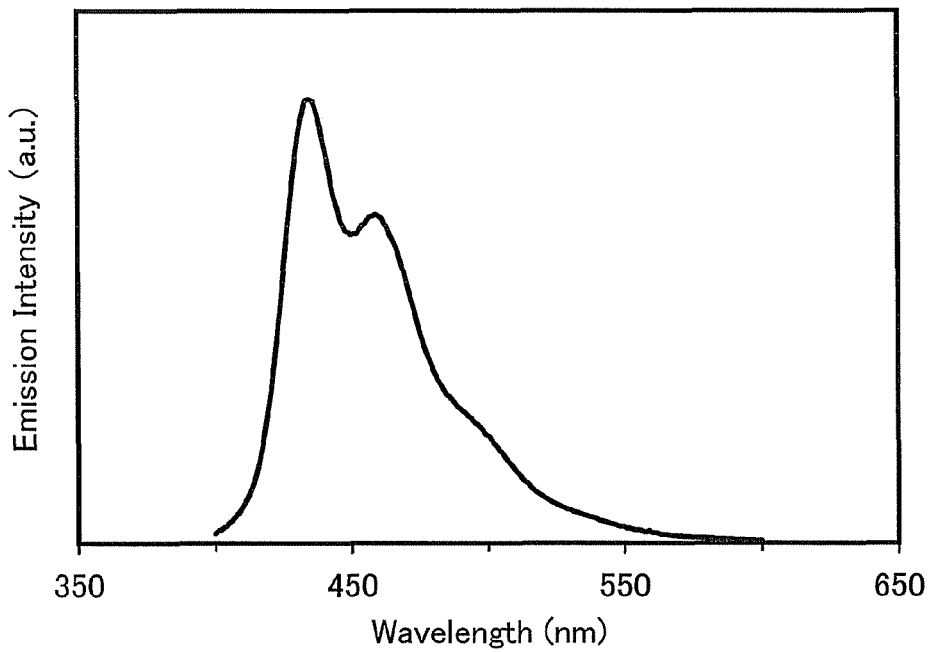
Figure 13A:
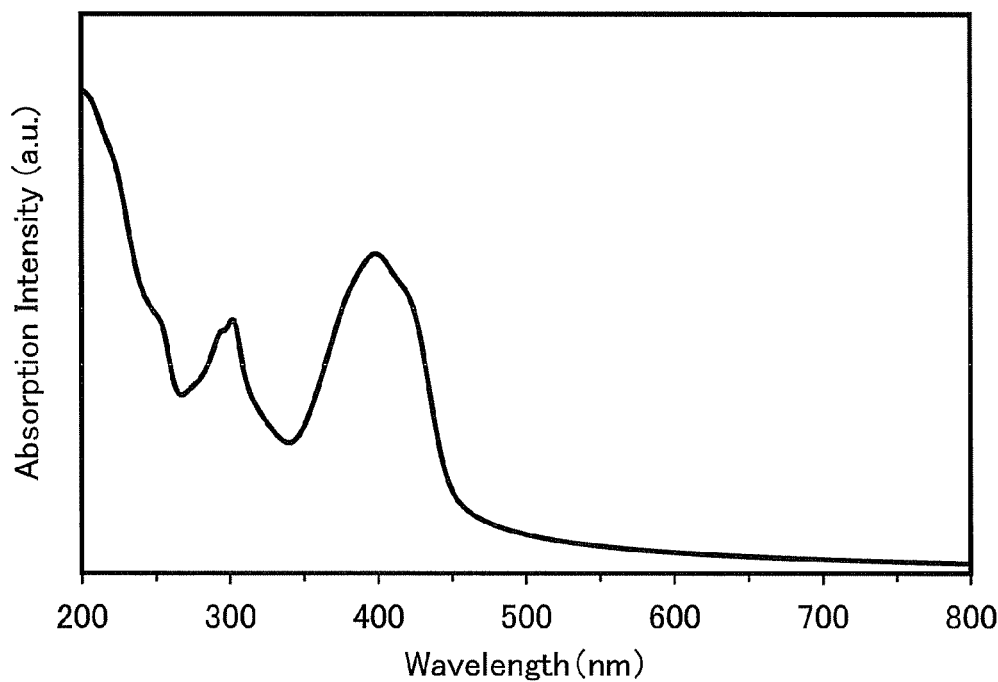
FIGS. 13A and 13B show an absorption and emission spectra of a thin film of FrA2S.
Figure 13B:
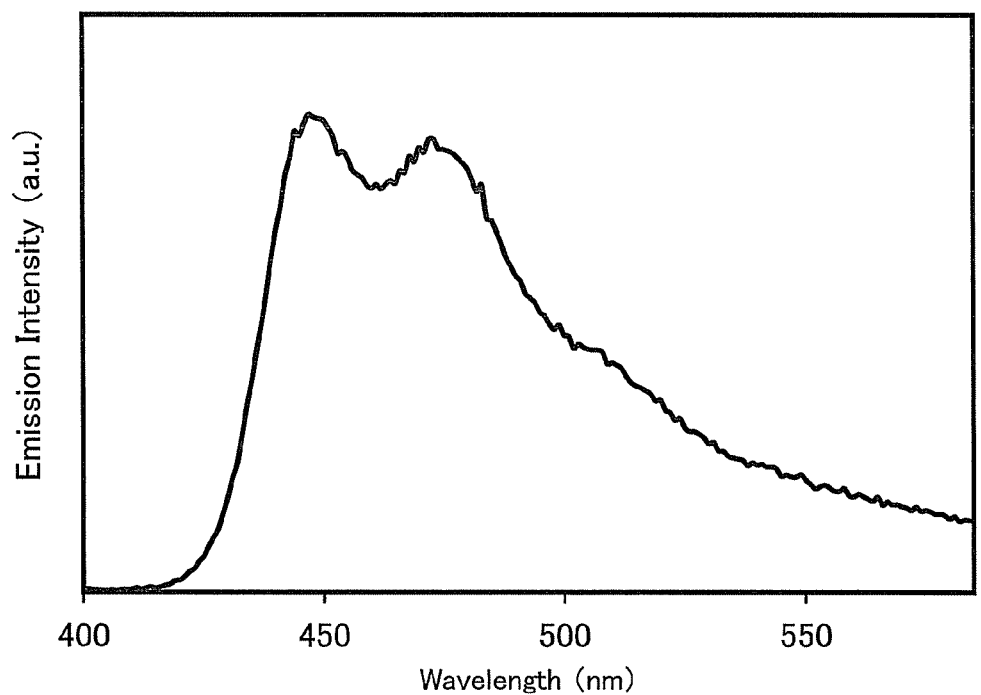

Farther, FIG. 12A shows an absorption spectrum of FrA2S in a toluene solution of FrA2S, and FIG. 12B shows an emission spectrum thereof. Furthermore, FIG. 13A shows an absorption spectrum of a thin film of FrA2S, and FIG. 13B shows an emission spectrum thereof. An ultraviolet-visible spectrophotometer (V-550, manufactured by JASCO Corporation) was used for the measurements of the absorption spectra. A fluorescence spectrophotometer (FS920, produced by Hamamatsu Photonics Corporation) was used for the measurements of the emission spectra. The measurements were performed with samples prepared in such a way that the solution was put in a quartz cell while the thin film was obtained by evaporation onto a quartz substrate. The figures show the absorption spectrum of the solution which was obtained by subtraction of the absorption spectra of quartz and toluene from those of quartz and the solution, and the absorption spectrum of the thin film which was obtained by subtraction of the spectrum of a quartz substrate from those of the quartz substrate and the thin film. In each of FIGS. 12A and 12B and FIGS. 13A and 13B, the horizontal axis represents wavelength (nm) and the vertical axis represents absorption intensity (an arbitrary unit) or emission intensity (arbitrary unit). In the case of the toluene solution, an absorption peak was observed at around 390 nm, and the maximum emission wavelength was 435 nm (at an excitation wavelength of 375 nm). In the case of the thin film, the absorption peaks were observed at around 399 nm and 302 nm, and the maximum emission wavelength was 444 nm (at an excitation wavelength of 302 nm).

The absorption spectra indicate that FrA2S described in this example is a material exhibiting little absorption in the visible region. In addition, the emission spectra indicate that FrA2S emits blue light.

EXAMPLE 2

This example illustrates results of the measurements of the highest occupied molecular orbital (HOMO) level, lowest unoccupied molecular orbital (LUMO) level, and band gap of the stilbene compound according to one embodiment of the invention, which was synthesized in Example 1, in a thin film state.

Note that the measurements in this example were performed as follows. The value of the HOMO level was obtained by conversion of the value of the ionization potential measured with a photoelectron spectrometer (AC-2, manufactured by Riken Keiki Co., Ltd.) in the air into a negative value. The value of the LUMO level was obtained in such a way that the absorption edge was obtained from a Tauc plot with an assumption of direct transition using the data of the absorption spectrum of the thin film which is shown in the above example and the absorption edge was added, as an optical energy gap, to the value of the HOMO level.

The HOMO level, LUMO level, and band gap of FrA2S, which were obtained by the measurements, are shown in Table 1 below.

TABLE 1

| Abbreviation | HOMO level (eV) | LUMO level (eV) | Band gap (eV) |
|---|---|---|---|
| FrA2S | −5.27 | −2.48 | 2.79 |

It is confirmed from Table 1 that FrA2S, which is a stilbene compound according to one embodiment of the present invention, has a relatively deep HOMO level, a shallow LUMO level, and a wide band gap.

Further, the shallow HOMO level indicates that it is easy to oxidize FrA2S, which is a stilbene compound according to one embodiment of the present invention. Therefore, FrA2S is a material suitable for a hole-injection layer and a hole-transport layer.

EXAMPLE 3

This example illustrates the way how a light-emitting element in which the stilbene compound synthesized in Example 1 according to one embodiment of the present invention is used for a light-emitting material was fabricated, and results of the measurements of the element characteristics.

The way how a light-emitting element 1 was fabricated is described hereinbelow with reference to FIG. 14. In addition, structural formulae of organic compounds used in this example are shown below.

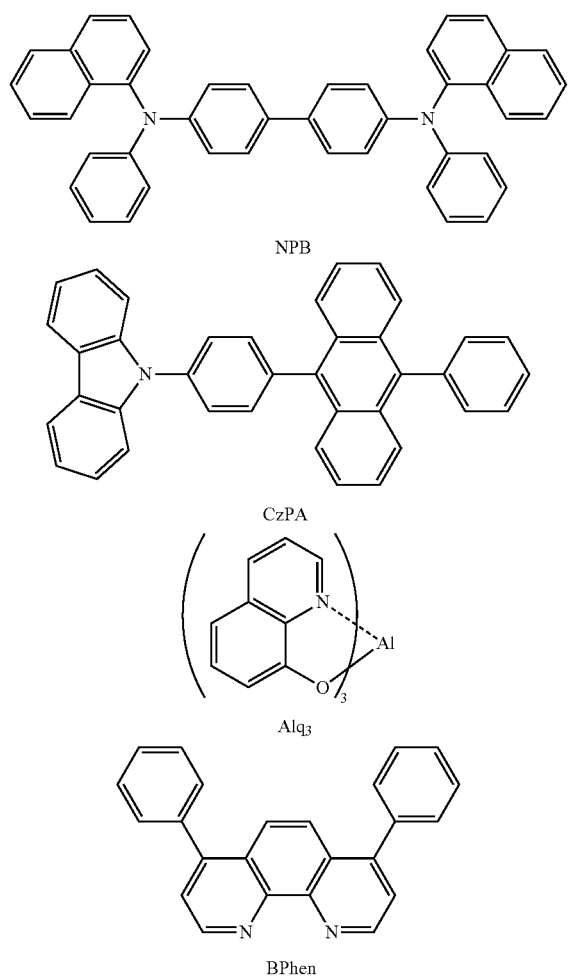

NPB

CzPA

Alq3

BPhen (Light-Emitting Element 1)

Figure 14:
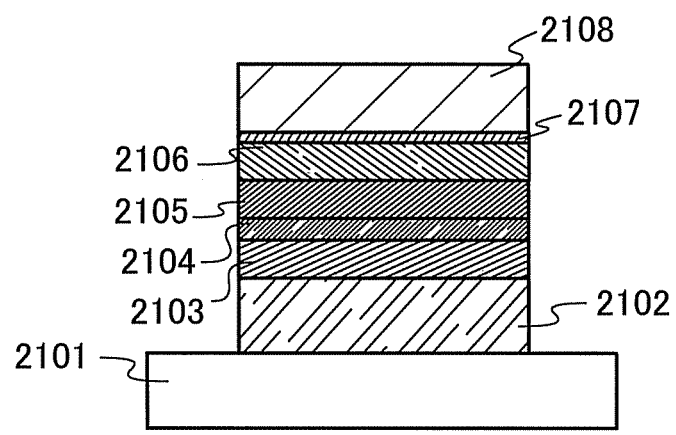
FIG. 14 illustrates a light-emitting element of Example.

First, as illustrated in FIG. 14, over a substrate 2101 which was a glass substrate, a film of indium tin oxide containing silicon (ITSO) was formed using a sputtering method, so that a first electrode 2102 was formed. The thickness thereof was set to 110 nm and the electrode area was set to 2 mm×2 mm. In this example, the first electrode 2102 was used as an anode.

Next, an EL layer in which a plurality of layers was stacked was formed over the first electrode 2102. The light-emitting element 1 has a structure where the EL layer includes a hole-injection layer 2103, a hole-transport layer 2104, a light-emitting layer 2105, an electron-transport layer 2106, and an electron-injection layer 2107, which are stacked in this order.

Next, the substrate 2101 over which the first electrode 2102 was formed was fixed to a substrate holder in a vacuum evaporation apparatus so that a surface on which the first electrode 2102 was provided faced downward. The pressure in the vacuum evaporation apparatus was reduced to about $10^{-4}$ Pa. Then, over the first electrode 2102, 4,4'-bis[N-(1-naphthyl)-N-phenylamino]biphenyl (abbreviation: NPB) and molybdenum(VI) oxide were co-evaporated to form a hole-injection layer 2103. The thickness of the hole-injection layer 2103 was set to 50 nm, and the evaporation rate was adjusted such that the weight ratio of NPB to molybdenum oxide was adjusted to 4:1 (=NPB:molybdenum oxide). Note that the co-evaporation method refers to an evaporation method in which evaporation is carried out from a plurality of evaporation sources at the same time in one treatment chamber.

Next, a film of a hole-transport material was formed to a thickness of 10 nm over the hole-injection layer 2103 by an evaporation method using resistance heating, so that the hole-transport layer 2104 was formed. Note that NPB was used for the hole-transport layer 2104.

Next, the light-emitting layer 2105 was formed over the hole-transport layer 2104 by an evaporation method using resistance heating. The light-emitting layer 2105 was formed in such a way that 9-[4-(10-phenyl-9-anthryl)phenyl]-9H-carbazole (abbreviation: CzPA) and 4,4'-bis[N-(dibenzofuran-2-yl)-N-phenylamino]stilbene (abbreviation: FrA2S) were co-evaporated to a thickness of 30 nm. Here, the evaporation rate was adjusted such that the weight ratio of CzPA to FrA2S was 1:0.05 (=CzPA:FrA2S).

Next, over the light-emitting layer 2105, a film of an electron-transport material was formed to a thickness of 10 nm to form the electron-transport layer 2106. Note that tris(8-quinolinolato)aluminum (abbreviation: Alq$_3$) was used for the electron-transport layer 2106.

Further, over electron-transport layer 2106, the electron-injection layer 2107 was foamed in such a way that tris(8-quinolinolato)aluminum (abbreviation: Alq$_3$) and lithium (Li) were co-evaporated to a thickness of 20 nm. Here, the evaporation rate was adjusted such that the weight ratio of Alq$_3$ to Li was 1:0.01(=Alq$_3$:Li).

Lastly, aluminum was evaporated to a thickness of 200 nm to form a second electrode 2108 functioning as a cathode. Thus, the light-emitting element 1 of this example was fabricated.

An element structure of the light-emitting element 1 fabricated in this example is shown in Table 2. In Table 2, the mixture ratios are all represented in weight ratios.

TABLE 2

| | First electrode 2102 | Hole-injection layer 2103 | Hole-transport layer 2104 | Light-emitting layer 2105 |
|---|---|---|---|---|
| Light-Emitting Element 1 | ITSO 100 nm | NPB:MoOx (=4:1) 50 nm | NPB 100 nm | CzPA:FrA2S (=1:0.05) 30 nm |
| | Electron-transport layer 2106 | Electron-injection layer 2107 | Second electrode 2108 | |
| Light-Emitting Element 1 | Alq$_3$ 10 nm | Alq$_3$:Li (=1:0.01) 20 nm | Al 200 nm | |

*The mixture ratios are all represented in weight ratios.

The mixture ratios are all represented in weight ratios.

The light-emitting element 1 obtained as described above was sealed in a glove box under a nitrogen atmosphere so as not to be exposed to air. After that, the operation characteristics of the light-emitting element were measured. Note that the measurements were carried out at room temperature (in an atmosphere kept at 25° C.).

In Table 3, the voltage (V), current (mA), current density (mA/cm$^2$), CIE chromaticity coordinates (x, y), current efficiency (cd/A), power efficiency (Lm/W), and external quantum efficiency (%) of the light-emitting element 1 are shown which are obtained at a luminance of about 1000 cd/m$^2$.

TABLE 3

| | Voltage (V) | Current (mA) | Current density (mA/cm$^2$) | Chromaticity (x, y) |
|---|---|---|---|---|
| Light-Emitting Element 1 | 5.4 | 0.94 | 23 | (0.17, 0.21) |

| | Current efficiency (cd/A) | Power efficiency (lm/W) | External quantum efficiency (%) |
|---|---|---|---|
| Light-Emitting Element 1 | 3.9 | 2.2 | 2.5 |

Figure 15:
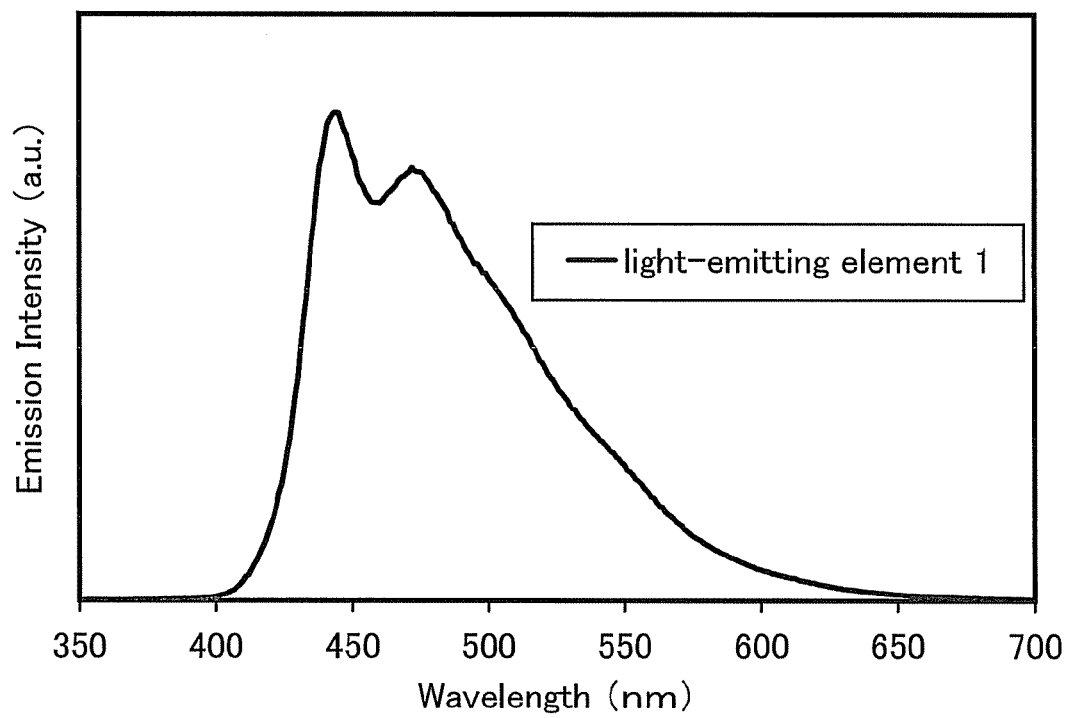
FIG. 15 shows an emission spectrum of a light-emitting element 1.

An emission spectrum of the light-emitting element 1 is shown in FIG. 15. In FIG. 15, the horizontal axis represents wavelength (nm), and the vertical axis represents emission intensity (arbitrary unit).

As seen from FIG. 15, the emission spectrum of the light-emitting element 1 has a peak around 444 nm. Further, the CIE chromaticity coordinates in Table 3 also indicate observation of blue light emission which originates from FrA2S. The light-emitting element 1 is thus found to be a light-emitting material having high color purity.

Figure 16:
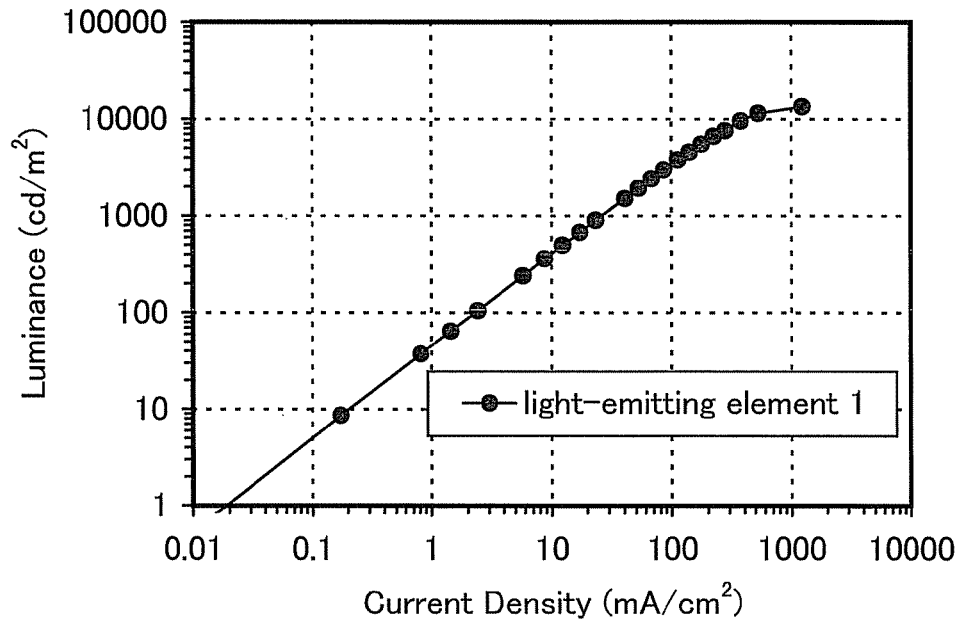
FIG. 16 shows luminance versus current density characteristics of the light-emitting element 1.
Figure 17:
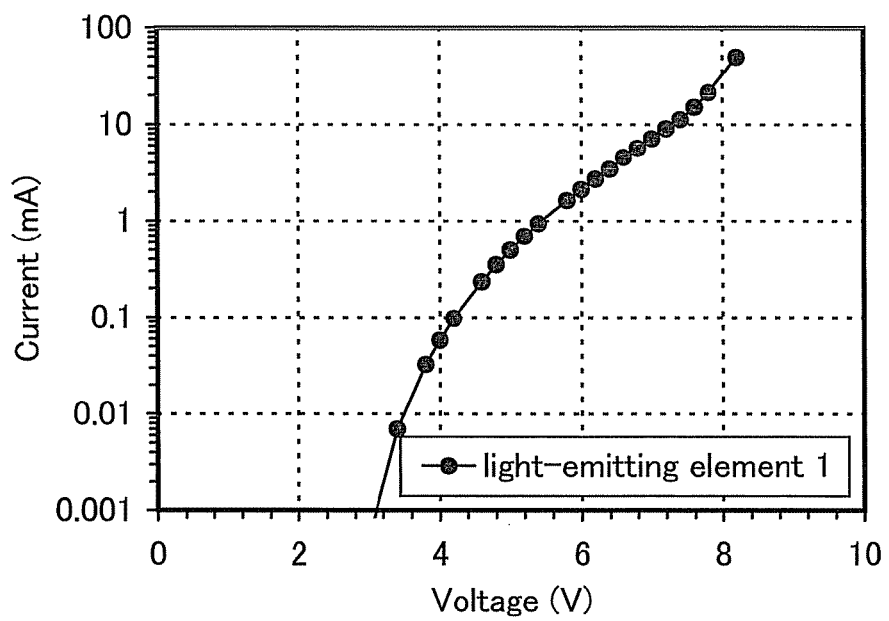
FIG. 17 shows current versus voltage characteristics of the light-emitting element 1.
Figure 18:
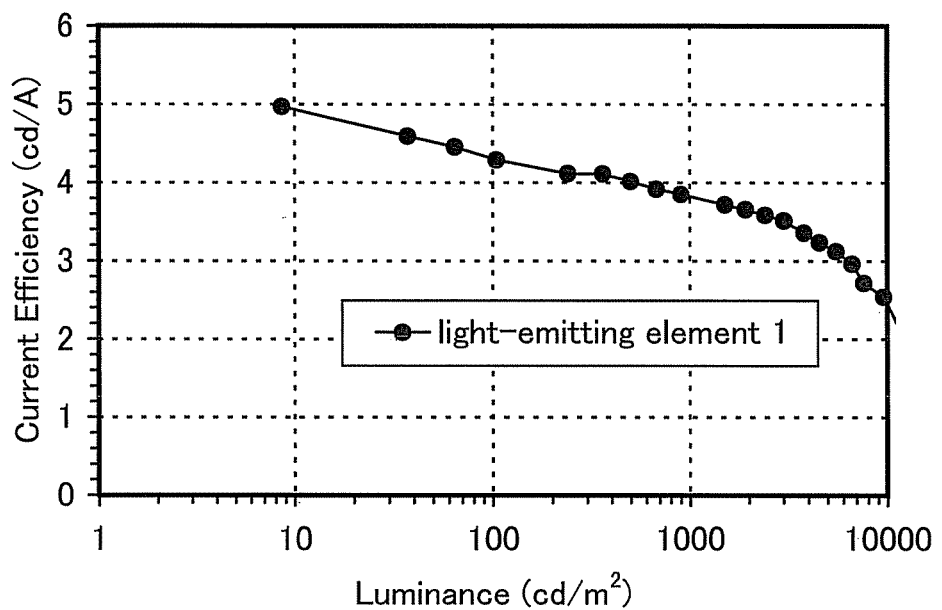
FIG. 18 shows current efficiency versus luminance characteristics of the light-emitting element 1.

Luminance versus current density characteristics of the light-emitting element 1 are shown in FIG. 16. In FIG. 16, the horizontal axis represents current density (mA/cm$^2$) and the vertical axis represents luminance (cd/m$^2$). Further, current versus voltage characteristics of the light-emitting element 1 are shown in FIG. 17. In FIG. 17, the horizontal axis represents voltage (V) and the vertical axis represents current (mA). In addition, current efficiency versus luminance characteristics of the light-emitting element 1 are shown in FIG. 18. In FIG. 18, the horizontal axis represents luminance (cd/m$^2$) and the vertical axis represents current efficiency (cd/A).

It is found from FIG. 16, FIG. 17, FIG. 18, and Table 3 that the light-emitting element 1 has low driving voltage and have high efficiency.

Figure 19:
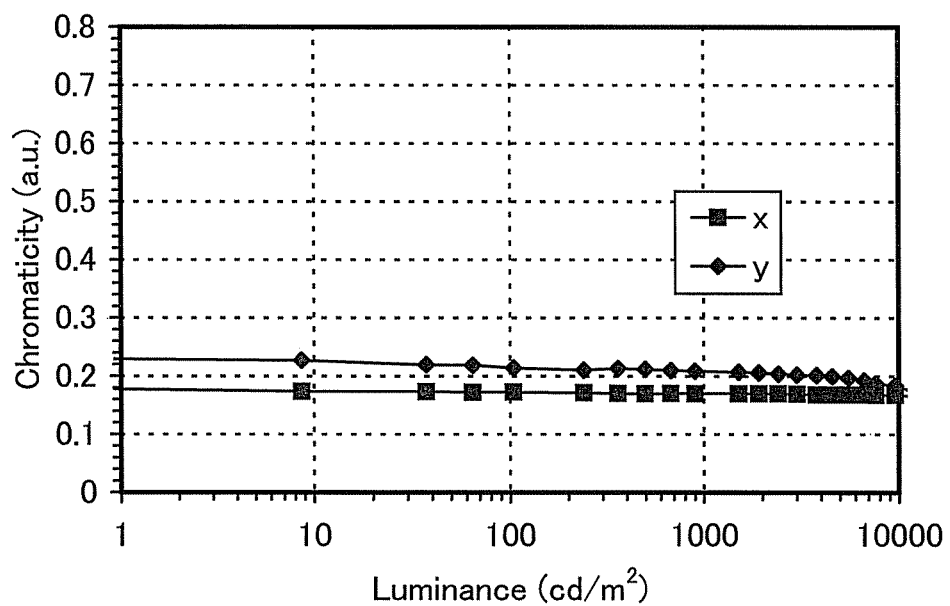
FIG. 19 shows chromaticity versus luminance characteristics of the light-emitting element 1.

In addition, FIG. 19 shows chromaticity versus luminance characteristics of the light-emitting element 1. In FIG. 19, the horizontal axis represents luminance (cd/m$^2$) and the vertical axis represents chromaticity (arbitrary unit).

It is found from FIG. 19 that even a change in luminance does not cause a change in the chromaticity of the blue that originates from FrA2S in the light-emitting element 1. Thus, the light-emitting element 1 is found to have favorable carrier balance, and to be less likely to cause a color shift during light adjustment. Accordingly, the light-emitting element 1 can be favorably used for a full-color display and the like.

Figure 20:
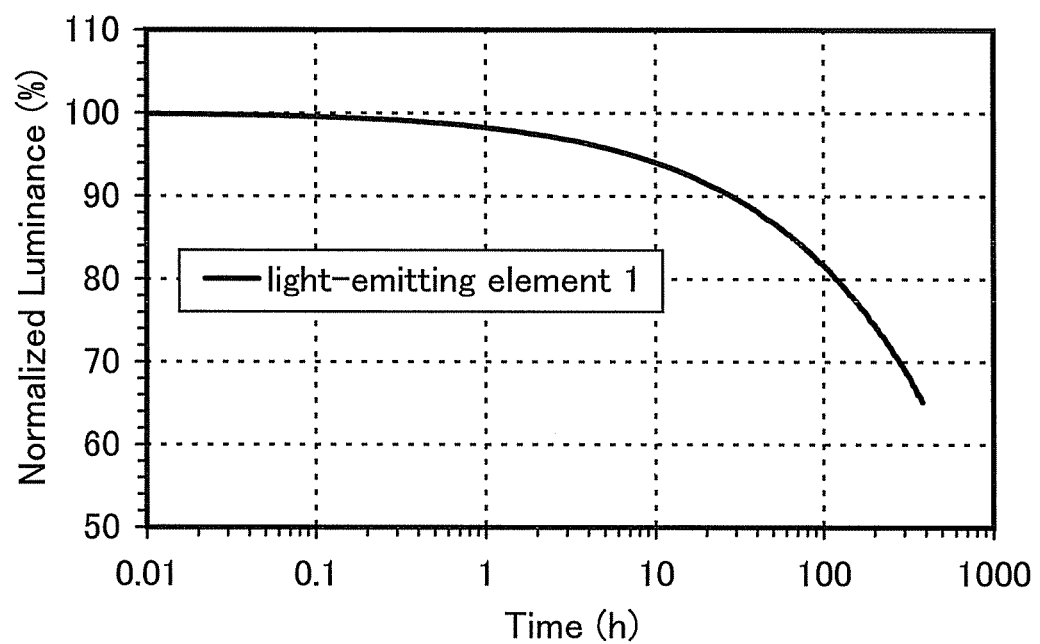
FIG. 20 shows results of a reliability test of the light-emitting element 1.

Further, the fabricated light-emitting element 1 was subjected to a reliability test. In the reliability test, this element was driven under conditions where the current density was constant with the initial luminance set to 1000 cd/m$^2$, and the luminance was measured after every certain period of time passed. Results of the reliability test are shown in FIG. 20. In FIG. 20, the horizontal axis represents current flow time (hour), and the vertical axis represents the proportion of luminance at each time in the initial luminance, i.e., normalized luminance (%).

It is found from FIG. 20 that the luminance of the light-emitting element 1 does not easily decrease with the passage of time, and the light-emitting element 1 has a long lifetime. In addition, the light-emitting element 1 kept about 65% of the initial luminance after driving for 380 hours.

As described above, it is confirmed that the light-emitting element 1 of this example can be a favorable blue light-emitting element and can be a blue light-emitting element with high color purity.

This application is based on Japanese Patent Application Serial No. 2011-005447 filed with the Japan Patent Office on Jan. 14, 2011, the entire contents of which are hereby incorporated by reference.

What is claimed is:

1. A stilbene compound represented by a general formula (G1) below:

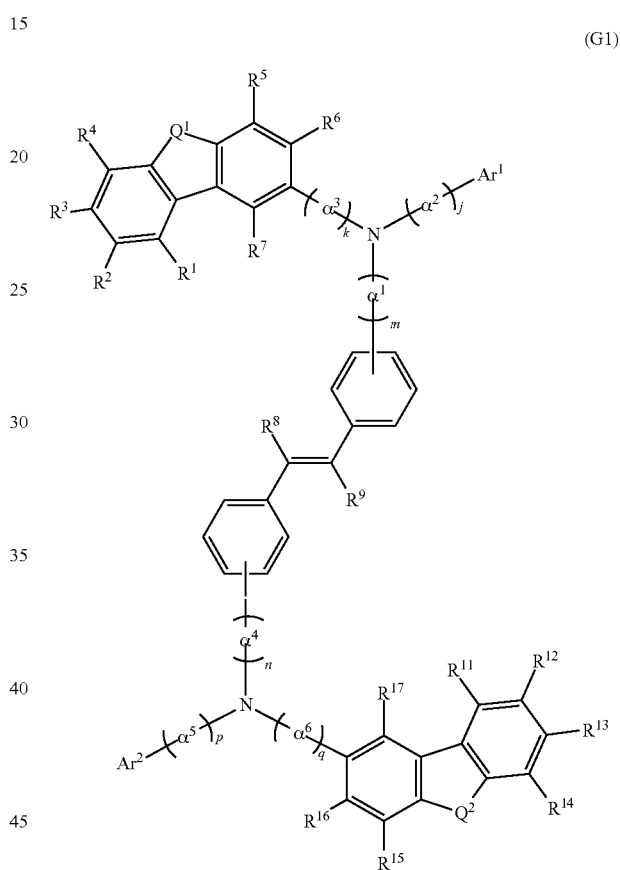

(G1)

wherein, in the general formula (G1):
$Q^1$ and $Q^2$ separately represent an oxygen atom or a sulfur atom;
$R^1$ to $R^9$ and $R^{11}$ to $R^{17}$ separately represent any one of a hydrogen atom, an alkyl group having 1 to 6 carbon atoms, a substituted or unsubstituted phenyl group, and a substituted or unsubstituted biphenyl group;
$\alpha^1$ to $\alpha^6$ separately represent a substituted or unsubstituted phenylene group;
$Ar^1$ and $Ar^2$ separately represent any one of a substituted or unsubstituted aryl group having 6 to 12 carbon atoms forming a ring, a substituted or unsubstituted dibenzothiophen-2-yl group, and a substituted or unsubstituted dibenzofuran-2-yl group; and
j, k, m, n, p, and q separately represent 0, or 1.

2. The stilbene compound according to claim 1, wherein $\alpha^1$ to $\alpha^6$ in the general formula (G1) are separately a structure represented by any one of structural formulae ($\alpha$-1) to ($\alpha$-3) below,

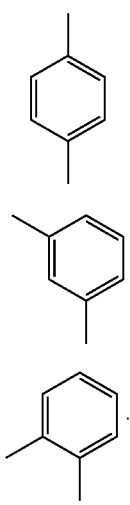 (α-1)

(α-2)

(α-3)

3. The stilbene compound according to claim 1,
wherein Ar$^1$ and Ar$^2$ in the general formula (G1) are separately a structure represented by a structural formula (Ar-1) or a general formula (Ar-2) below, and (Ar-1)

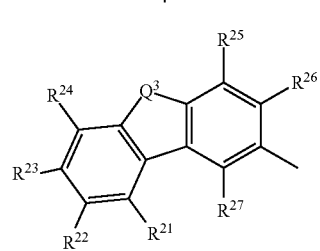 (Ar-2)

wherein, in the general formula (Ar-2), Q$^3$ represents an oxygen atom or a sulfur atom, and R$^{21}$ to R$^{27}$ separately represent any one of a hydrogen atom, an alkyl group having 1 to 6 carbon atoms, a substituted or unsubstituted phenyl group, and a substituted or unsubstituted biphenyl group.

4. The stilbene compound according to claim 1,
wherein R$^1$ to R$^9$, R$^{11}$ to R$^{17}$, and R$^{21}$ to R$^{27}$ are separately a structure represented by any one of structural formulae (R-1) to (R-9) below,

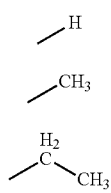 (R-1)

(R-2)

(R-3)

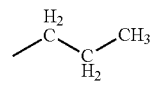 (R-4)

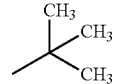 (R-5)

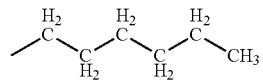 (R-6)

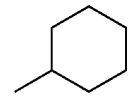 (R-7)

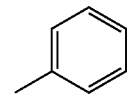 (R-8)

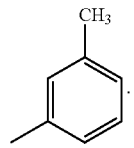 (R-9)

5. A light-emitting element comprising the stilbene compound according to claim 1.

6. A light-emitting device comprising the light-emitting element according to claim 5.

7. A lighting device comprising the light-emitting device according to claim 6.

8. An electronic device comprising the light-emitting device according to claim 6.

9. A stilbene compound represented by a general formula (G2) below:

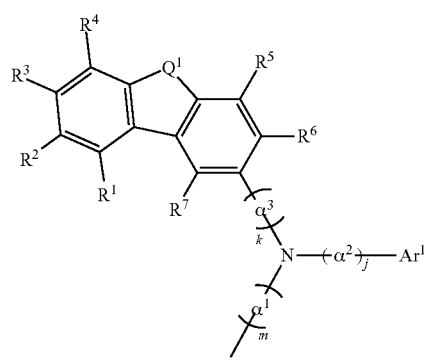 (G2)

-continued

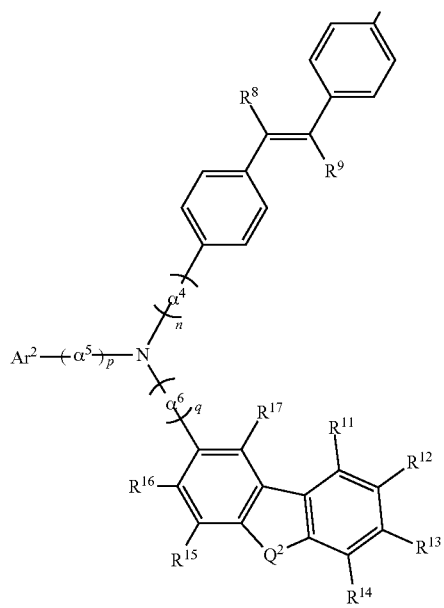

wherein, in the general formula (G2):

Q$^1$ and Q$^2$ separately represent an oxygen atom or a sulfur atom;

R$^1$ to R$^9$ and R$^{11}$ to R$^{17}$ separately represent any one of a hydrogen atom, an alkyl group having 1 to 6 carbon atoms, a substituted or unsubstituted phenyl group, and a substituted or unsubstituted biphenyl group;

α$^1$ to α$^6$ separately represent a substituted or unsubstituted phenylene group;

Ar$^1$ and Ar$^2$ separately represent any one of a substituted or unsubstituted aryl group having 6 to 12 carbon atoms forming a ring, a substituted or unsubstituted dibenzothiophen-2-yl group, and a substituted or unsubstituted dibenzofuran-2-yl group; and j, k, m, n, p, and q separately represent 0 or 1.

10. The stilbene compound according to claim 9, wherein α$^1$ to α$^6$ in the general formula (G2) are separately a structure represented by any one of structural formulae (α-1) to (α-3) below,

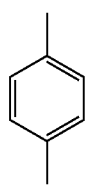 (α-1)

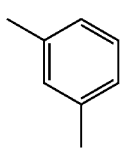 (α-2)

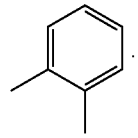 (α-3)

11. The stilbene compound according to claim 9, wherein Ar$^1$ and Ar$^2$ in the general formula (G2) are separately a structure represented by a structural formula (Ar-1) or a general formula (Ar-2) below, and

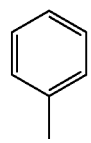 (Ar-1)

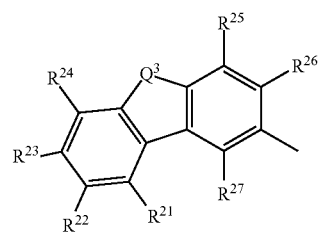 (Ar-2)

wherein, in the general formula (Ar-2), Q$^3$ represents an oxygen atom or a sulfur atom, and R$^{21}$ to R$^{27}$ separately represent any one of a hydrogen atom, an alkyl group having 1 to 6 carbon atoms, a substituted or unsubstituted phenyl group, and a substituted or unsubstituted biphenyl group.

12. The stilbene compound according to claim 9, wherein R$^1$ to R$^9$, R$^{11}$ to R$^{17}$, and R$^{21}$ to R$^{27}$ are separately a structure represented by any one of structural formulae (R-1) to (R-9) below,

 (R-1)

 (R-2)

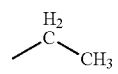 (R-3)

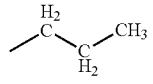 (R-4)

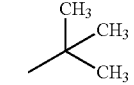 (R-5)

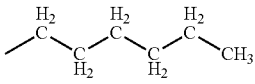 (R-6)

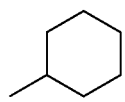 (R-7)

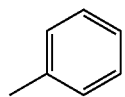 (R-8)

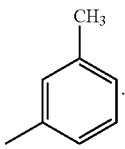 (R-9)

13. A light-emitting element comprising the stilbene compound according to claim 9.

14. A light-emitting device comprising the light-emitting element according to claim 13.

15. A lighting device comprising the light-emitting device according to claim 14.

16. An electronic device comprising the light-emitting device according to claim 14.

17. A stilbene compound represented by a general formula (G3) below:

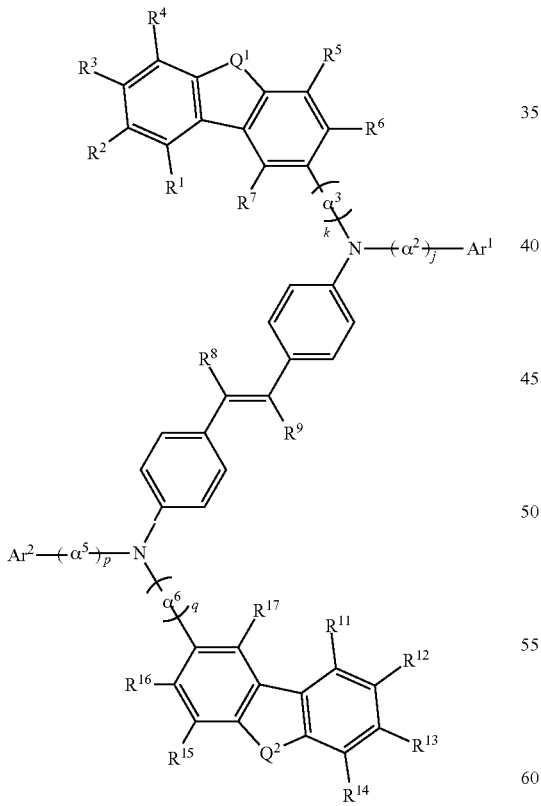 (G3)

wherein, in the general formula (G3):
$Q^1$ and $Q^2$ separately represent an oxygen atom or a sulfur atom;
$R^1$ to $R^9$ and $R^{11}$ to $R^{17}$ separately represent any one of a hydrogen atom, an alkyl group having 1 to 6 carbon atoms, a substituted or unsubstituted phenyl group, and a substituted or unsubstituted biphenyl group;
$\alpha^2$, $\alpha^3$, $\alpha^5$, and $\alpha^6$ separately represent a substituted or unsubstituted phenylene group;
$Ar^1$ and $Ar^2$ separately represent any one of a substituted or unsubstituted aryl group having 6 to 12 carbon atoms forming a ring, a substituted or unsubstituted dibenzothiophen-2-yl group, and a substituted or unsubstituted dibenzofuran-2-yl group; and
j, k, p, and q separately represent 0 or 1.

18. The stilbene compound according to claim 17,
wherein $Ar^1$ and $Ar^2$ in the general formula (G3) are separately a structure represented by a structural formula (Ar-1) or a general formula (Ar-2) below, and

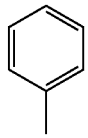 (Ar-1)

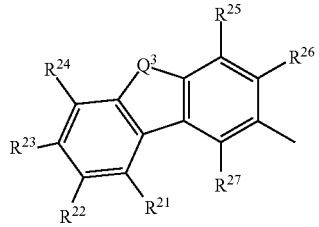 (Ar-2)

wherein, in the general formula (Ar-2), $Q^3$ represents an oxygen atom or a sulfur atom, and $R^{21}$ to $R^{27}$ separately represent any one of a hydrogen atom, an alkyl group having 1 to 6 carbon atoms, a substituted or unsubstituted phenyl group, and a substituted or unsubstituted biphenyl group.

19. The stilbene compound according to claim 17,
wherein $R^1$ to $R^9$, $R^{11}$ to $R^{17}$, and $R^{21}$ to $R^{27}$ are separately a structure represented by any one of structural formulae (R-1) to (R-9) below,

 (R-1)

 (R-2)

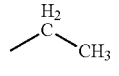 (R-3)

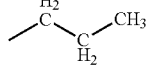 (R-4)

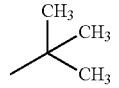 (R-5)

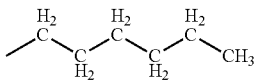 (R-6)

-continued (R-7)

(R-8)

(R-9)

20. A light-emitting element comprising the stilbene compound according to claim 17.
21. A light-emitting device comprising the light-emitting element according to claim 20.
22. A lighting device comprising the light-emitting device according to claim 21.
23. An electronic device comprising the light-emitting device according to claim 21.
24. A stilbene compound represented by a general formula (G4) below:

(G4)

wherein, in the general formula (G4):
$Q^1$ and $Q^2$ separately represent an oxygen atom or a sulfur atom;

$R^1$ to $R^9$ and $R^{11}$ to $R^{17}$ separately represent any one of a hydrogen, atom, an alkyl group having 1 to 6 carbon atoms, a substituted or unsubstituted phenyl group, and a substituted or unsubstituted biphenyl group;

$\alpha^2$ and $\alpha^5$ separately represent a substituted or unsubstituted phenylene group;

$Ar^1$ and $Ar^2$ separately represent any one of a substituted or unsubstituted aryl group having 6 to 12 carbon atoms forming a ring, a substituted or unsubstituted dibenzothiophen-2-yl group, and a substituted or unsubstituted dibenzofuran-2-yl group; and j and p separately represent 0 or 1.

25. The stilbene compound according to claim 24,
wherein $Ar^1$ and $Ar^2$ in the general formula (G4) are separately a structure represented by a structural formula (Ar-1) or a general formula (Ar-2) below, and (Ar-1)

(Ar-2)

wherein, in the general formula (Ar-2), $Q^3$ represents an oxygen atom or a sulfur atom, and $R^{21}$ to $R^{27}$ separately represent any one of a hydrogen atom, an alkyl group having 1 to 6 carbon atoms, a substituted or unsubstituted phenyl group, and a substituted or unsubstituted biphenyl group.

26. The stilbene compound according to claim 24,
wherein $R^1$ to $R^9$, $R^{11}$ to $R^{17}$, and $R^{21}$ to $R^{27}$ are separately a structure represented by any one of structural formulae (R-1) to (R-9) below, (R-1)

(R-2)

(R-3)

(R-4)

(R-5)

-continued
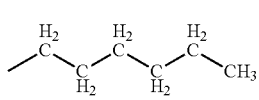 (R-6)
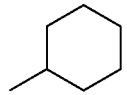 (R-7)
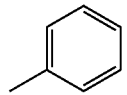 (R-8)
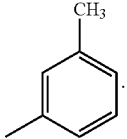 (R-9)
27. A light-emitting element comprising the stilbene compound according to claim 24.
28. A light-emitting device comprising the light-emitting element according to claim 27.
29. A lighting device comprising the light-emitting device according to claim 28.
30. An electronic device comprising the light-emitting device according to claim 28.
* * * * *

UNITED STATES PATENT AND TRADEMARK OFFICE
CERTIFICATE OF CORRECTION

PATENT NO.        : 8,664,263 B2
APPLICATION NO.   : 13/348939
DATED             : March 4, 2014
INVENTOR(S)       : Harue Osaka and Nobuharu Ohsawa Page 1 of 1

It is certified that error appears in the above-identified patent and that said Letters Patent is hereby corrected as shown below:

In the Specification:

Column 9, line 62; Change "faun" to --form--.

Column 25, line 7; Change "Further" to --Furthermore,--.

Column 31, line 32 to 33; Change "7,14-diphenyl-methylphenyl)" to
--7,14-diphenyl-N,N,N',N'-tetrakis(4-methylphenyl)--.

Column 33, line 39; Change "of, the" to --of the--.

Column 34, line 9; Change "forted" to --formed--.

Column 35, line 42; Change "fax" to --far--.

Column 36, line 58; Change "funned" to --formed--.

Column 37, line 15; Change "foamed" to --formed--.

Column 38, line 27; Change "fanned" to --formed--.

Column 43, line 14; Change "crystal, display" to --crystal display--.

Column 47, line 43; Change "Farther," to --Further,--.

Column 50, line 23; Change "foamed" to --formed--.

Column 50, line 65; Change "(Lm/W)," to --(lm/W),--.

In the Claims:

Column 60, line 2, Claim 24; Change "hydrogen, atom," to --hydrogen atom,--.

Signed and Sealed this
First Day of July, 2014

Michelle K. Lee
*Deputy Director of the United States Patent and Trademark Office*